(12) United States Patent
Stamatopoulos et al.

(10) Patent No.: US 11,304,624 B2
(45) Date of Patent: Apr. 19, 2022

(54) METHOD AND APPARATUS FOR PERFORMING DYNAMIC RESPIRATORY CLASSIFICATION AND ANALYSIS FOR DETECTING WHEEZE PARTICLES AND SOURCES

(71) Applicant: BreathResearch, Walnut Creek, CA (US)

(72) Inventors: Charalampos-Christos Stamatopoulos, Athens (GR); Nirinjan Bikko Yee, Walnut Creek, CA (US)

(73) Assignee: AireHealth Inc., Winter Springs, FL (US)

( * ) Notice: Subject to any disclaimer, the term of this patent is extended or adjusted under 35 U.S.C. 154(b) by 494 days.

(21) Appl. No.: 16/196,987

(22) Filed: Nov. 20, 2018

(65) Prior Publication Data

US 2019/0192047 A1    Jun. 27, 2019

Related U.S. Application Data

(63) Continuation-in-part of application No. 15/641,262, filed on Jul. 4, 2017, now Pat. No. 10,426,426, which
(Continued)

(51) Int. Cl.
*A61B 5/08* (2006.01)
*A61B 5/00* (2006.01)
(Continued)

(52) U.S. Cl.
CPC ............ *A61B 5/0823* (2013.01); *A61B 5/024* (2013.01); *A61B 5/0205* (2013.01);
(Continued)

(58) Field of Classification Search
None
See application file for complete search history.

(56) References Cited

U.S. PATENT DOCUMENTS 7,463,922 B1*  12/2008  Snyder ................. A61N 1/3904
                                                              607/5
2004/0127807 A1*   7/2004  Hatlesad ................ A61B 7/003
                                                              600/529
(Continued)

OTHER PUBLICATIONS

Kiyokawa, Hiroshi, et al. "Auditory detection of simulated crackles in breath sounds." Chest 119.6 (2001): 1886-1892. (Year: 2001).*
(Continued)

*Primary Examiner* — Jacqueline Cheng
*Assistant Examiner* — Jairo H Portillo

(57) ABSTRACT

A method for analyzing an audio respiratory signal comprises capturing the audio respiratory signal from a subject using a microphone and partitioning the audio respiratory signal into a plurality of overlapping frames. The method further comprises calculating a fourier transform for each frame and determining a magnitude spectrum using the fourier transform of the plurality of overlapping frames. Additionally, the method comprises extracting a spectrogram using the magnitude spectrum and analyzing the spectrogram to determine characteristics pertaining to wheeze sounds in the audio respiratory signal.

17 Claims, 46 Drawing Sheets

Related U.S. Application Data is a continuation-in-part of application No. 13/920,655, filed on Jun. 18, 2013, now Pat. No. 9,814,438.

(60) Provisional application No. 61/661,267, filed on Jun. 18, 2012.

(51) Int. Cl.
| | | |
|---|---|---|
| *A61B 7/00* | (2006.01) | |
| *A61B 5/024* | (2006.01) | |
| *G06N 3/08* | (2006.01) | |
| *G10L 25/66* | (2013.01) | |
| *A61B 5/0205* | (2006.01) | |
| *A61B 7/04* | (2006.01) | |
| *G10L 25/30* | (2013.01) | |
| *G16H 50/20* | (2018.01) | |
| *G10L 25/18* | (2013.01) | |
| *G10L 25/06* | (2013.01) | |

(52) U.S. Cl.
CPC .......... *A61B 5/0816* (2013.01); *A61B 5/0826* (2013.01); *A61B 5/6823* (2013.01); *A61B 5/725* (2013.01); *A61B 5/7278* (2013.01); *A61B 5/7465* (2013.01); *A61B 7/003* (2013.01); *A61B 7/04* (2013.01); *G06N 3/08* (2013.01); *G10L 25/66* (2013.01); *A61B 5/6819* (2013.01); *A61B 5/6831* (2013.01); *A61B 5/742* (2013.01); *G10L 25/06* (2013.01); *G10L 25/18* (2013.01); *G10L 25/30* (2013.01); *G16H 50/20* (2018.01)

(56) References Cited

U.S. PATENT DOCUMENTS

| | | | | |
|---|---|---|---|---|
| 2005/0123150 | A1* | 6/2005 | Betts | G10L 21/0208 381/94.3 |
| 2007/0282506 | A1* | 12/2007 | Breed | G06K 9/00838 701/45 |
| 2011/0125044 | A1* | 5/2011 | Rhee | A61B 5/113 600/534 |
| 2013/0060100 | A1* | 3/2013 | Wurm | A61B 7/003 600/301 |
| 2013/0178756 | A1* | 7/2013 | Suzuki | A61B 5/7282 600/529 |
| 2013/0190641 | A1* | 7/2013 | Gonnen | A61B 5/087 600/538 |
| 2014/0257126 | A1* | 9/2014 | Vink | A61B 7/003 600/529 |

OTHER PUBLICATIONS

Naves, Raphael, Bruno HG Barbosa, and Danton D. Ferreira. "Classification of lung sounds using higher-order statistics: A divide-and-conquer approach." Computer methods and programs in biomedicine 129 (2016): 12-20. (Year: 2016).*

Lin, Bor-Shing, et al. "Wheeze recognition based on 2D bilateral filtering of spectrogram." Biomedical Engineering: Applications, Basis and Communications 18.03 (2006): 128-137. (Year: 2006).*

\* cited by examiner

METHOD AND APPARATUS FOR PERFORMING DYNAMIC RESPIRATORY CLASSIFICATION AND ANALYSIS FOR DETECTING WHEEZE PARTICLES AND SOURCES

CROSS-REFERENCE TO RELATED APPLICATIONS

The present application is a Continuation-in-Part of, claims the benefit of and priority to U.S. application Ser. No. 15/641,262, Attorney Docket BRTH-0004.USP, filed Jul. 4, 2017, entitled "METHODS AND APPARATUS FOR PERFORMING DYNAMIC RESPIRATORY CLASSIFICATION AND TRACKING," and hereby incorporated by reference in its entirety, which claims priority from U.S. application Ser. No. 13/920,655, Attorney Docket BRTH-0004.US, filed Jun. 18, 2013, now issued as U.S. Pat. No. 9,814,438, entitled "METHODS AND APPARATUS FOR PERFORMING DYNAMIC RESPIRATORY CLASSIFICATION AND TRACKING" and hereby incorporated by reference in its entirety, which claims priority from U.S. Provisional Application No. 61/661,267 Attorney Docket BRTH-0004.B, filed Jun. 18, 2012, entitled "Methods and Apparatus To Determine Ventilatory and Respiratory Compensation Thresholds," assigned to the assignee of the present application and the entire disclosure of which is incorporated herein by reference.

FIELD OF THE INVENTION

Embodiments according to the present invention relate to dynamically analyzing breathing sounds using an electronic device.

BACKGROUND OF THE INVENTION

In conventional respiratory analysis systems, in order determine an athlete's Ventilatory Threshold ("VT") and Respiratory Compensation Threshold ("RCT"), a complex medical device (often referred to as gas or metabolic analyzers) and the personnel to conduct the test are required. This is often cost prohibitive. One additional scientific way to measure VT and RCT is to use a blood lactate analysis. However, this is an invasive medical procedure. Another method to measure VT and RCT is to use the Foster talk test, but, in this case, the athlete has too much room for personal and subjective interpretation and thus the results may not be as reliable as the more scientific methods.

Further, while respiratory analysis has conventionally been used to perform diagnosis for certain disorders, e.g., airway constrictions and pathologies etc., conventional methods of performing respiratory analysis are typically cumbersome to use because they employ intricate apparatuses for capturing and analyzing breathing activity. In addition, conventional methods of performing respiratory analysis do not take into account full breath cycles; they do not analyze the different breath phases in a breathing cycle, namely, inhale, transition, exhale and rest.

BRIEF SUMMARY OF THE INVENTION

Accordingly, there is a need for improved methods and apparatus to determine VT and RCT. Further, there is a need for improved methods and apparatus to detect wheeze and crackle sounds and lung pathologies associated therewith. Using the beneficial aspects of the systems described, without their respective limitations, embodiments of the present invention provide novel solutions to the challenges inherent in determining VT and RCT in a non-invasive and accurate fashion.

Further, there is a need for a method and apparatus for performing respiratory acoustic analysis that uses inexpensive and readily available means for capturing and reporting breathing activity. Further, there is a need for a method and apparatus that takes into account full breath cycles when performing respiratory analysis. In other words, there is a need for a method and apparatus for performing respiratory analysis that is operable to analyze the different breath phases in a breathing cycle, namely, inhale, transition, exhale and rest.

In one embodiment, a method for detecting thresholds in a breathing session is disclosed. The method comprises recording breathing sounds of a subject using a microphone. The method further comprises processing the breathing sounds to generate an audio respiratory signal and recognizing a plurality of breath cycles from the audio respiratory signal. Additionally, the method comprises extracting metrics related to a breath intensity and a breath rate from the plurality of breath cycles and producing a plurality of vectors using the metrics related to the breath intensity and the breath rate. Further, the method comprises calculating a master vector by summing the plurality of vectors and assigning each value in the master vector with a weighting coefficient and determining the thresholds using peak values in said master vector.

In another embodiment, a computer-readable storage medium having stored thereon, computer executable instructions that, if executed by a computer system cause the computer system to perform a method for detecting thresholds in a breathing session is disclosed. The method comprises recording breathing sounds of a subject using a microphone. The method further comprises processing the breathing sounds to generate an audio respiratory signal and recognizing a plurality of breath cycles from the audio respiratory signal. Additionally, the method comprises extracting metrics related to a breath intensity and a breath rate from the plurality of breath cycles and producing a plurality of vectors using the metrics related to the breath intensity and the breath rate. Further, the method comprises calculating a master vector by summing the plurality of vectors and assigning each value in the master vector with a weighting coefficient and determining the thresholds using peak values in said master vector.

In a different embodiment, an apparatus for detecting thresholds in a breathing session is disclosed. The apparatus comprises a microphone for capturing breathing sounds of a subject, a memory comprising an application for determining ventilatory thresholds from a breathing session stored therein and a processor coupled to the memory and the microphone, the processor being configured to operate in accordance with the application to: (a) record breathing sounds of a subject using a microphone; (b) process the breathing sounds to generate an audio respiratory signal; (c) recognize a plurality of breath cycles from the audio respiratory signal; (d) extract metrics related to a breath intensity and a breath rate from the plurality of breath cycles; (e) produce a plurality of vectors using the metrics related to the breath intensity and the breath rate; (f) calculate a master vector by summing the plurality of vectors and assigning each value in the master vector with a weighting coefficient; and (g) determine the thresholds using peak values in the master vector.

In one embodiment, a method for detecting wheeze from an audio respiratory signal is disclosed. The method comprises capturing the audio respiratory signal from a subject using a microphone. Further, the method comprises recognizing a plurality of breath cycles and a plurality of breath phases from the audio respiratory signal and detecting wheezing from the plurality of breath cycles and the plurality of breath phases. The detecting comprises analyzing a block of interest in the audio respiratory signal, wherein the block of interest comprises a plurality of frames. The detecting further comprises calculating an auto-correlation function (ACF) for each frame in the block and determining a maximum value of the ACF calculated for each frame in the block. Finally, the detecting comprises analyzing the maximum value to detect if wheezing is present in the block.

In one embodiment, a method for detecting wheeze from an audio respiratory signal is disclosed. The method comprises capturing the audio respiratory signal generated by a subject using a microphone. The method further comprises recognizing a plurality of breath cycles and a plurality of breath phases from the audio respiratory signal. Further, the method comprises detecting wheezing from the plurality of breath cycles and the plurality of breath phases, wherein the detecting comprises: (a) analyzing a block of interest in the audio respiratory signal, wherein the block of interest comprises a plurality of frames; (b) calculating an auto-correlation function (ACF) for each frame in the block of interest; (c) determining a maximum value of the ACF calculated for each frame in the block of interest; and (d) analyzing the maximum value to detect if wheezing is present in the block of interest.

In one embodiment, a non-transitory computer-readable storage medium having stored thereon, computer executable instructions that, if executed by a computer system cause the computer system to perform a method for detecting wheeze from an audio respiratory signal is disclosed. The method comprises capturing the audio respiratory signal generated by a subject using a microphone. The method further comprises recognizing a plurality of breath cycles and a plurality of breath phases from the audio respiratory signal. Further, the method comprises detecting wheezing from the plurality of breath cycles and the plurality of breath phases, wherein the detecting comprises: (a) analyzing a block of interest in the audio respiratory signal, wherein the block of interest comprises a plurality of frames; (b) calculating an auto-correlation function (ACF) for each frame in the block of interest; (c) determining a maximum value of the ACF calculated for each frame in the block of interest; and (d) analyzing the maximum value to detect if wheezing is present in the block of interest.

In another embodiment, a system for detecting wheeze from an audio respiratory signal is disclosed. The system comprises a spirometer comprising a first microphone, wherein the first microphone is operable to capture the audio respiratory signal from a subject and a memory coupled to the spirometer and operable to store the audio respiratory signal, wherein the memory further comprises an application for detecting wheeze and crackle from a breathing session stored therein. The system also comprises a processor coupled to the memory and the spirometer, the processor configured to operate in accordance with said application to recognize a plurality of breath cycles and a plurality of breath phases from the audio respiratory signal and detect wheezing from the plurality of breath cycles and the plurality of breath phases, wherein the detect wheezing is performed by the process which is configured to: (a) analyze a block of interest in the audio respiratory signal, wherein the block of interest comprises a plurality of frames; (b) calculate an auto-correlation function (ACF) for each frame in the block of interest; (c) determine a maximum value of the ACF calculated for each frame in the block of interest; and (d) analyze the maximum value to detect if wheezing is present in the block of interest.

In one embodiment, a method for analyzing an audio respiratory signal is disclosed. The method comprises capturing the audio respiratory signal from a subject using a microphone and partitioning the audio respiratory signal into a plurality of overlapping frames. Further, the method comprises calculating a fourier transform for each frame and determining a magnitude spectrum using the fourier transform of the plurality of overlapping frames. The method also comprises extracting a spectrogram using the magnitude spectrum and analyzing the spectrogram to determine characteristics pertaining to wheeze sounds in the audio respiratory signal.

In one embodiment, a non-transitory computer-readable storage medium having stored thereon, computer executable instructions that, if executed by a computer system cause the computer system to perform a method for analyzing an audio respiratory signal is disclosed. The method comprises capturing the audio respiratory signal from a subject using a microphone and partitioning the audio respiratory signal into a plurality of overlapping frames. The method also comprises calculating a fourier transform for each frame and extracting a spectrogram using the fourier transform of the plurality of overlapping frames. Finally, the method comprises analyzing the spectrogram to determine characteristics pertaining to wheeze sounds in the audio respiratory signal.

In one embodiment, a system for detecting wheeze and crackle from an audio respiratory signal is disclosed. The system comprises a spirometer comprising a first microphone, wherein the first microphone is operable to capture the audio respiratory signal from a subject and a memory coupled to the spirometer and operable to store the audio respiratory signal, wherein the memory further comprises an application for detecting wheeze and crackle from a breathing session stored therein. The system also comprises a processor coupled to the memory and the spirometer, the processor being configured to operate in accordance with said application to: (a) capture the audio respiratory signal from a subject using a microphone; (b) partition the audio respiratory signal into a plurality of overlapping frames; (c) calculate a fourier transform for each frame; (d) determine a magnitude spectrum using the fourier transform of the plurality of overlapping frames; (e) extract a spectrogram using the magnitude spectrum; and (e) analyze the spectrogram to determine characteristics pertaining to wheeze sounds in the audio respiratory signal.

In another embodiment, a computer-implemented method for determining lung pathology from an audio respiratory signal is disclosed. The method comprises inputting a plurality of audio files comprising a training set into an artificial neural network, wherein the plurality of audio files comprise sessions with patients with known pathologies of known degrees of severity. The method further comprises annotating the plurality of audio files in the training set with metadata relevant to the patients and the known pathologies and analyzing the plurality of audio files, wherein the analyzing comprises extracting spectrograms for each of the plurality of audio files and a plurality of descriptors associated with wheeze and crackle from the plurality of audio files. Further, the method comprises training the artificial neural network using the plurality of audio files, the spectrograms, the metadata and the plurality of descriptors and inputting a recording of a new patient into the artificial neural network. Finally, the method comprises determining a pathology and associated severity for the new patient using the artificial neural network.

In another embodiment, a non-transitory computer-readable storage medium having stored thereon, computer executable instructions that, if executed by a computer system cause the computer system to perform a method for determining lung pathology from an audio respiratory signal is disclosed. The method comprises inputting a plurality of audio files comprising a training set into an artificial neural network, wherein the plurality of audio files comprise sessions with patients with known pathologies of known degrees of severity. Further, the method comprises annotating the plurality of audio files in the training set with metadata relevant to the patients and the known pathologies and analyzing the plurality of audio files, wherein the analyzing comprises extracting spectrograms for each of the plurality of audio files. The method also comprises training the artificial neural network using the plurality of audio files, the spectrograms, the metadata and the plurality of descriptors and inputting a recording of a new patient into the artificial neural network. Finally, the method comprises determining a pathology and associated severity for the new patient using the artificial neural network.

In a different embodiment, a system for determining lung pathology from an audio respiratory signal is presented. The system comprises a memory for storing a plurality of audio files, instructions associated with an artificial neural network and a process for determining lung pathology from an audio respiratory signal and a processor coupled to the memory, the processor being configured to operate in accordance with the instructions to: (a) input a plurality of audio files comprising a training set into an artificial neural network, wherein the plurality of audio files comprise sessions with patients with known pathologies of known degrees of severity; (b) annotate the plurality of audio files in the training set with metadata relevant to the patients and the known pathologies; (c) analyze the plurality of audio files, wherein the analyzing comprises extracting spectrograms for each of the plurality of audio files; (d) train the artificial neural network using the plurality of audio files, the spectrograms, the metadata and the plurality of descriptors; (e) input a recording of a new patient into the artificial neural network; and (e) determine a pathology and associated severity for the new patient using the artificial neural network.

The following detailed description together with the accompanying drawings will provide a better understanding of the nature and advantages of the present invention.

BRIEF DESCRIPTION OF THE DRAWINGS

Embodiments of the present invention are illustrated by way of example, and not by way of limitation, in the figures of the accompanying drawings and in which like reference numerals refer to similar elements.

Figure 1:
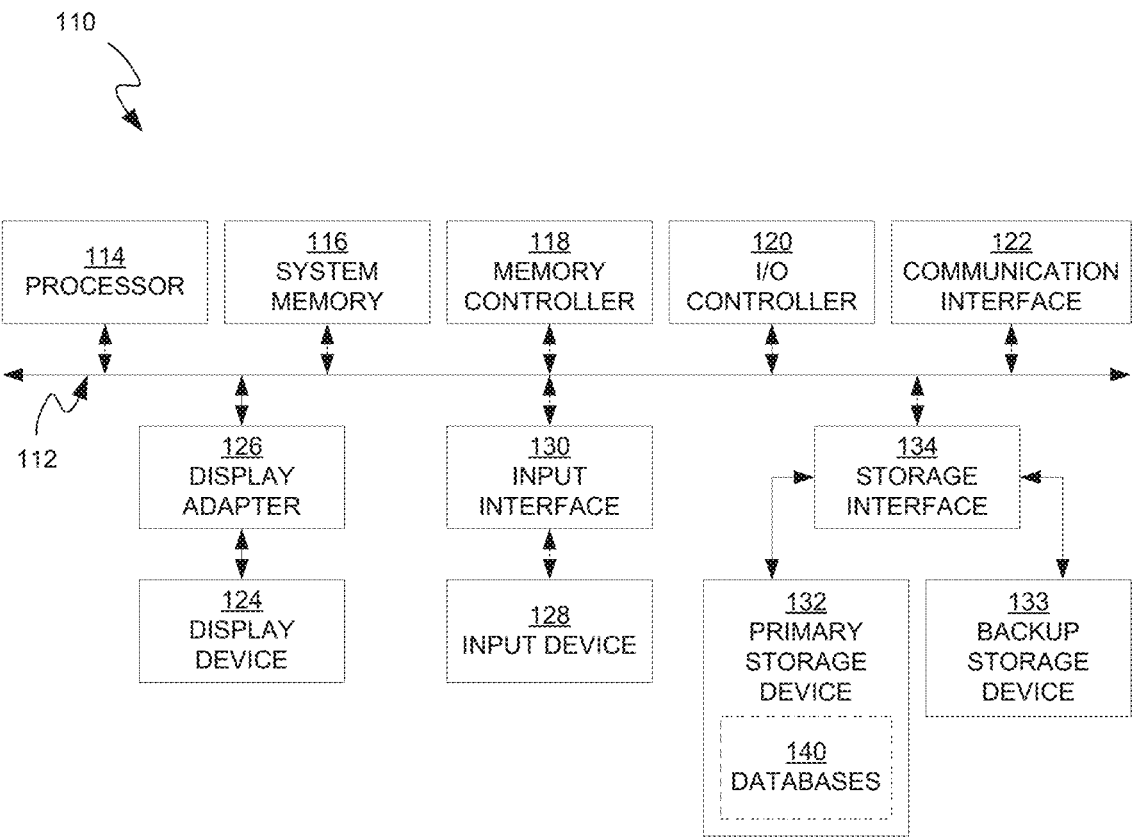
FIG. 1 is an exemplary computer system in accordance with embodiments of the present invention.

In the figures, elements having the same designation have the same or similar function.

DETAILED DESCRIPTION OF THE INVENTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "analyzing," "generating," "classifying," "filtering," "calculating," "performing," "extracting," "recognizing," "capturing," or the like, refer to actions and processes (e.g., flowchart 900 of FIG. 9) of a computer system or similar electronic computing device or processor (e.g., system 110 of FIG. 1). The computer system or similar electronic computing device manipulates and transforms data represented as physical (electronic) quantities within the computer system memories, registers or other such information storage, transmission or display devices.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer-readable storage media and communication media; non-transitory computer-readable media include all computer-readable media except for a transitory, propagating signal. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared, and other wireless media. Combinations of any of the above can also be included within the scope of computer-readable media.

FIG. 1 is a block diagram of an example of a computing system 110 used to perform respiratory acoustic analysis and capable of implementing embodiments of the present disclosure. Computing system 110 broadly represents any single or multi-processor computing device or system capable of executing computer-readable instructions. Examples of computing system 110 include, without limitation, workstations, laptops, client-side terminals, servers, distributed computing systems, handheld devices, or any other computing system or device. In its most basic configuration, computing system 110 may include at least one processor 114 and a system memory 116.

Processor 114 generally represents any type or form of processing unit capable of processing data or interpreting and executing instructions. In certain embodiments, processor 114 may receive instructions from a software application or module. These instructions may cause processor 114 to perform the functions of one or more of the example embodiments described and/or illustrated herein.

System memory 116 generally represents any type or form of volatile or non-volatile storage device or medium capable of storing data and/or other computer-readable instructions. Examples of system memory 116 include, without limitation, RAM, ROM, flash memory, or any other suitable memory device. Although not required, in certain embodiments computing system 110 may include both a volatile memory unit (such as, for example, system memory 116) and a non-volatile storage device (such as, for example, primary storage device 132).

Computing system 110 may also include one or more components or elements in addition to processor 114 and system memory 116. For example, in the embodiment of FIG. 1, computing system 110 includes a memory controller 118, an input/output (I/O) controller 120, and a communication interface 122, each of which may be interconnected via a communication infrastructure 112. Communication infrastructure 112 generally represents any type or form of infrastructure capable of facilitating communication between one or more components of a computing device. Examples of communication infrastructure 112 include, without limitation, a communication bus (such as an Industry Standard Architecture (ISA), Peripheral Component Interconnect (PCI), PCI Express (PCIe), or similar bus) and a network.

Memory controller 118 generally represents any type or form of device capable of handling memory or data or controlling communication between one or more components of computing system 110. For example, memory controller 118 may control communication between processor 114, system memory 116, and I/O controller 120 via communication infrastructure 112.

I/O controller 120 generally represents any type or form of module capable of coordinating and/or controlling the input and output functions of a computing device. For example, I/O controller 120 may control or facilitate transfer of data between one or more elements of computing system 110, such as processor 114, system memory 116, communication interface 122, display adapter 126, input interface 130, and storage interface 134.

Communication interface 122 broadly represents any type or form of communication device or adapter capable of facilitating communication between example computing system 110 and one or more additional devices. For example, communication interface 122 may facilitate communication between computing system 110 and a private or public network including additional computing systems. Examples of communication interface 122 include, without limitation, a wired network interface (such as a network interface card), a wireless network interface (such as a wireless network interface card), a modem, and any other suitable interface. In one embodiment, communication interface 122 provides a direct connection to a remote server via a direct link to a network, such as the Internet. Communication interface 122 may also indirectly provide such a connection through any other suitable connection.

Communication interface 122 may also represent a host adapter configured to facilitate communication between computing system 110 and one or more additional network or storage devices via an external bus or communications channel. Examples of host adapters include, without limitation, Small Computer System Interface (SCSI) host adapters, Universal Serial Bus (USB) host adapters, IEEE (Institute of Electrical and Electronics Engineers) 1394 host adapters, Serial Advanced Technology Attachment (SATA) and External SATA (eSATA) host adapters, Advanced Technology Attachment (ATA) and Parallel ATA (PATA) host adapters, Fibre Channel interface adapters, Ethernet adapters, or the like. Communication interface 122 may also allow computing system 110 to engage in distributed or remote computing. For example, communication interface 122 may receive instructions from a remote device or send instructions to a remote device for execution.

As illustrated in FIG. 1, computing system 110 may also include at least one display device 124 coupled to communication infrastructure 112 via a display adapter 126. Display device 124 generally represents any type or form of device capable of visually displaying information forwarded by display adapter 126. Similarly, display adapter 126 generally represents any type or form of device configured to forward graphics, text, and other data for display on display device 124.

As illustrated in FIG. 1, computing system 110 may also include at least one input device 128 coupled to communication infrastructure 112 via an input interface 130. Input device 128 generally represents any type or form of input device capable of providing input, either computer- or human-generated, to computing system 110. Examples of input device 128 include, without limitation, a keyboard, a pointing device, a speech recognition device, or any other input device.

As illustrated in FIG. 1, computing system 110 may also include a primary storage device 132 and a backup storage device 133 coupled to communication infrastructure 112 via a storage interface 134. Storage devices 132 and 133 generally represent any type or form of storage device or medium capable of storing data and/or other computer-readable instructions. For example, storage devices 132 and 133 may be a magnetic disk drive (e.g., a so-called hard drive), a floppy disk drive, a magnetic tape drive, an optical disk drive, a flash drive, or the like. Storage interface 134 generally represents any type or form of interface or device for transferring data between storage devices 132 and 133 and other components of computing system 110.

In one example, databases 140 may be stored in primary storage device 132. Databases 140 may represent portions of a single database or computing device or it may represent multiple databases or computing devices. For example, databases 140 may represent (be stored on) a portion of computing system 110 and/or portions of example network architecture 200 in FIG. 2 (below). Alternatively, databases 140 may represent (be stored on) one or more physically separate devices capable of being accessed by a computing device, such as computing system 110 and/or portions of network architecture 200.

Continuing with reference to FIG. 1, storage devices 132 and 133 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 132 and 133 may also include other similar structures or devices for allowing computer software, data, or other computer-readable instructions to be loaded into computing system 110. For example, storage devices 132 and 133 may be configured to read and write software, data, or other computer-readable information. Storage devices 132 and 133 may also be a part of computing system 110 or may be separate devices accessed through other interface systems.

Many other devices or subsystems may be connected to computing system 110. Conversely, all of the components and devices illustrated in FIG. 1 need not be present to practice the embodiments described herein. The devices and subsystems referenced above may also be interconnected in different ways from that shown in FIG. 1. Computing system 110 may also employ any number of software, firmware, and/or hardware configurations. For example, the example embodiments disclosed herein may be encoded as a computer program (also referred to as computer software, software applications, computer-readable instructions, or computer control logic) on a computer-readable medium.

The computer-readable medium containing the computer program may be loaded into computing system 110. All or a portion of the computer program stored on the computer-readable medium may then be stored in system memory 116 and/or various portions of storage devices 132 and 133. When executed by processor 114, a computer program loaded into computing system 110 may cause processor 114 to perform and/or be a means for performing the functions of the example embodiments described and/or illustrated herein. Additionally or alternatively, the example embodiments described and/or illustrated herein may be implemented in firmware and/or hardware.

Methods and Apparatus for Performing Dynamic Respiratory Classification and Tracking I. Ventilatory Threshold (VT) and Respiratory Compensation Threshold (RCT) Determination Broadly, one embodiment of the present invention provides a mobile device application that uses a microphone as a means for recording the user's breathing for the purpose of measuring the VT and RCT thresholds. The microphone can periodically listen to breath sounds at the nose and/or the mouth and the software automatically derives estimates of VT and RCT therefrom. The mobile application may include one or more computer implemented procedures that can record breath sounds and receive pulse rate information from the user to generate an estimate of VT and RCT.

An electronic device, such as a portable computer, mobile electronic device, or a smartphone, may be configured with appropriate software and inputs to permit breath sound data recording and recording data from a heart rate monitor simultaneously. The electronic device, in one embodiment, may be implemented using a computing system similar to computing system 110.

Figure 2:
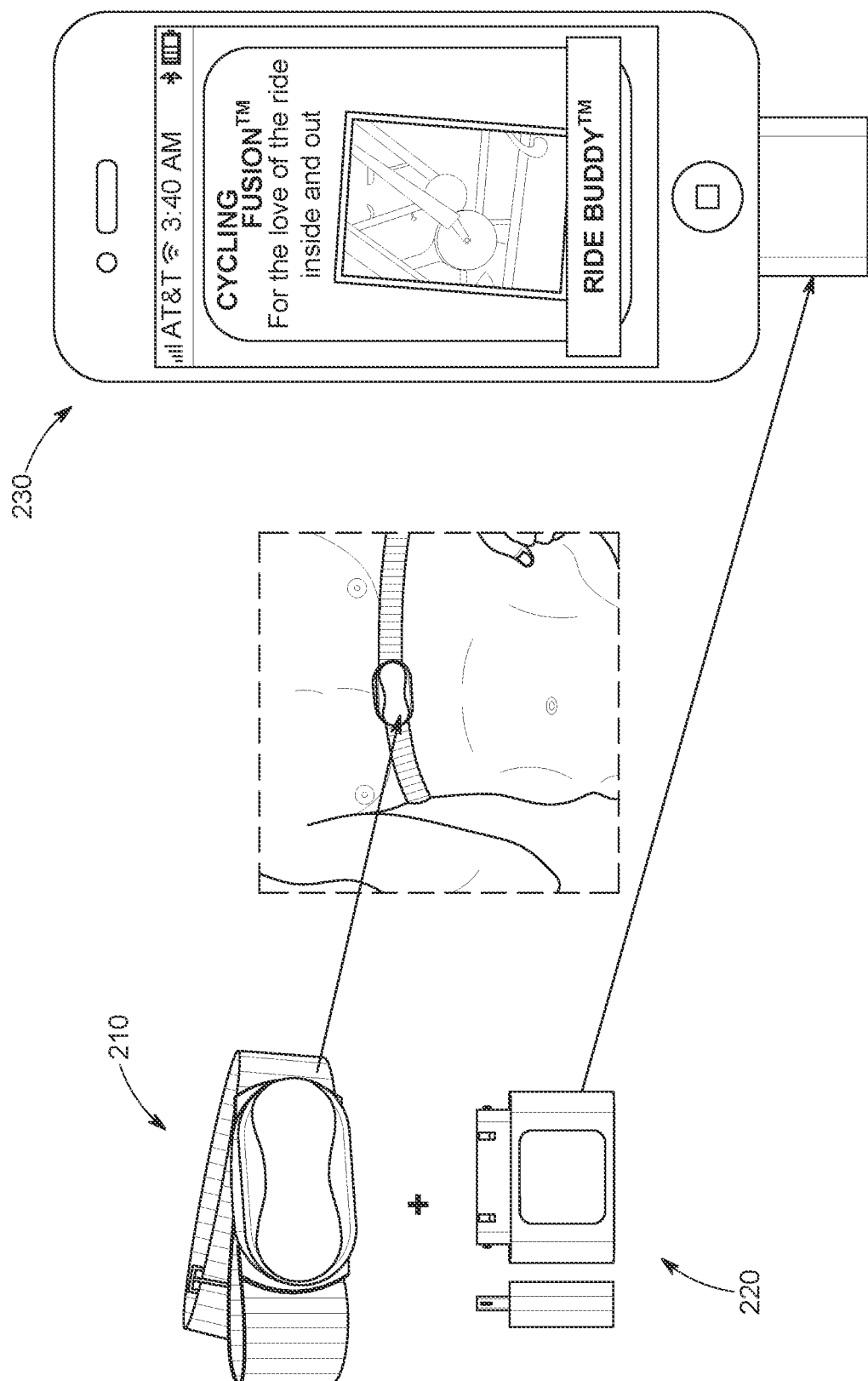
FIG. 2 shows one example of a pulse measuring device for a mobile electronic device according to an exemplary embodiment of the present invention.

FIG. 2 shows one example of a pulse measuring device for a mobile electronic device according to an exemplary embodiment of the present invention. The pulse measuring device shown in the embodiment illustrated in FIG. 2 is a heart monitor transmitter belt 210 that is communicatively coupled with a receiver module 220. The transmitter 210 transmits heart rate information, among other things, to the receiver module 220. In one embodiment, the transmission can take place wirelessly using a near field communication protocol such as Bluetooth. The receiver module 220, in one embodiment, can plug into a portable electronic device 230 such as a smart-phone. The portable electronic device 230, in one embodiment, can use the information from the receiver module 220 to undertake further analysis of the pulse rate. Also it can use the pulse rate in conjunction with the breath sound to generate an estimate of the VT and RCT.

Figure 3:
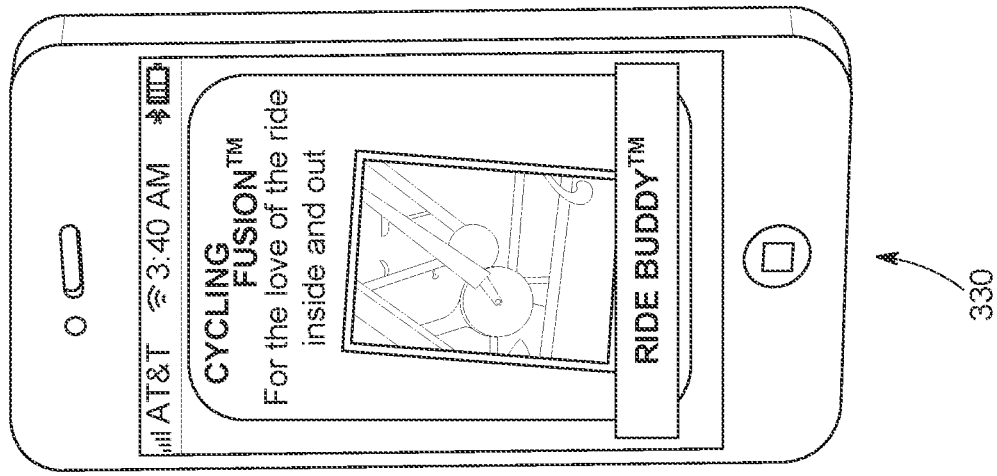
FIG. 3 shows another example of a pulse measuring device for a mobile electronic device according to an exemplary embodiment of the present invention.
Figure 3:
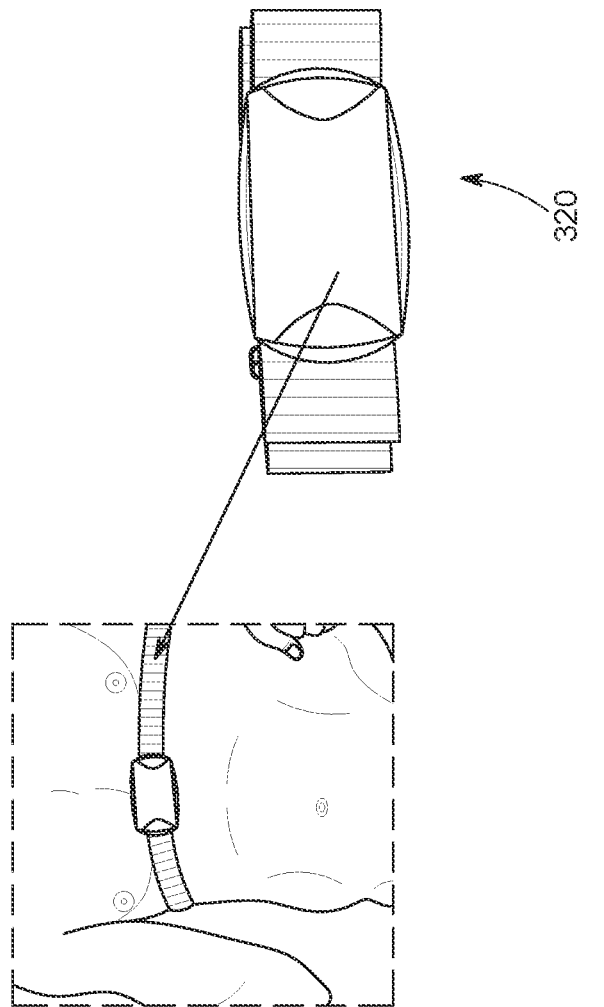

FIG. 3 shows another example of a pulse measuring device for a mobile electronic device according to an exemplary embodiment of the present invention. In the embodiment illustrated in FIG. 3, the heart monitor transmitter belt 320 is configured to transmit signals directly to an electronic device 330, such as a smart-phone. The computer-implemented procedures running on device 330 can decode the transmission to undertake further analysis of the pulse rate. Also they can use the pulse rate correlated to the VT and RCT estimates from the breath sound analysis to create heart training zones for the user. In one embodiment, the transmission can take place wirelessly using a near field communication protocol such as Bluetooth. Alternatively, in one embodiment, electronic device 330 can be at a remote location and receive the transmission through a cellular signal.

A microphone can pick up the breathing patterns of the user at rest and during exercise (or some anabolic activity) and a heart monitor transmitter belt, or some other heart rate monitoring device, can simultaneously pick up the heart beats and send them in a continuous (regular frequency) fashion to a heart monitor receiver. In one embodiment, the microphone is readily available commercially and affordable.

Figure 4:
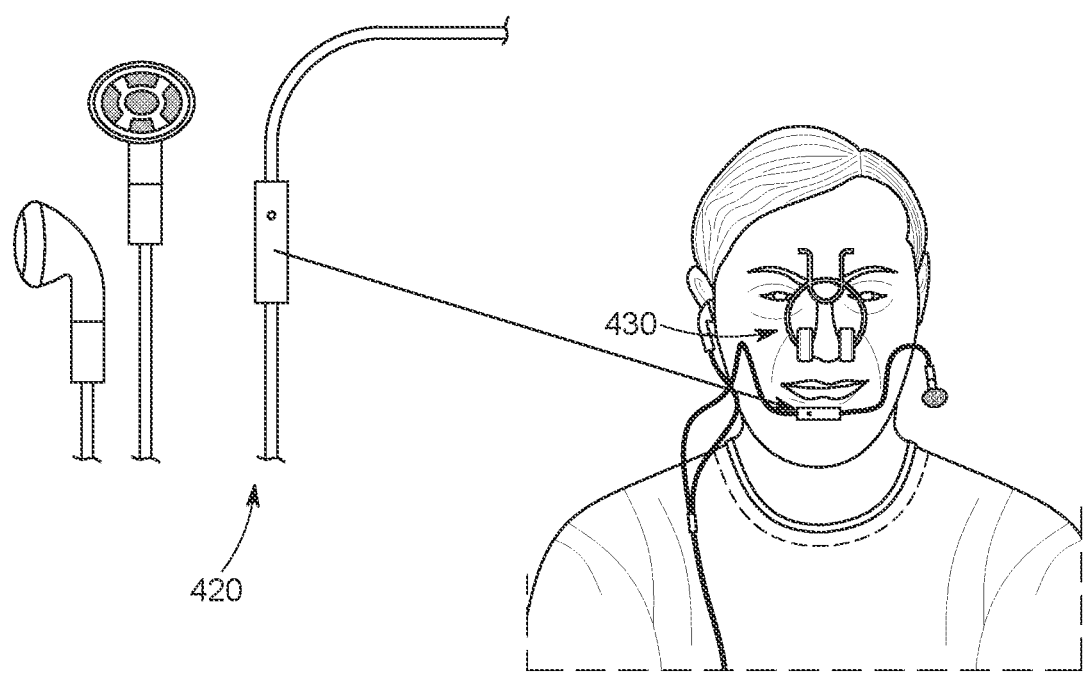
FIG. 4 shows an exemplary breathing microphone set-up used in the methods and apparatus of the present invention.

FIG. 4 shows an exemplary breathing microphone set-up used in the methods and apparatus of the present invention. In one embodiment, a conventional microphone 420, available commercially, can be used to record the breathing patterns of the user. By using only the microphone 420 that comes with many electronic devices (such as an iPad® or iPhone®) and the software as described here within, the present invention can provide VT and RCT data for a fraction of the cost of alternative options. Moreover, the test can be self-administered, not requiring special testing equipment or trained personnel.

Various designs may be used to create an accurate breath sound measurement. In some embodiments, as shown in FIG. 4, the user's nose may be closed to ensure the microphone at the user's mouth captures the entirety of the user's breathing. In a different embodiment, the breathing sound can be captured both at the user's nose and the mouth.

Figure 5:
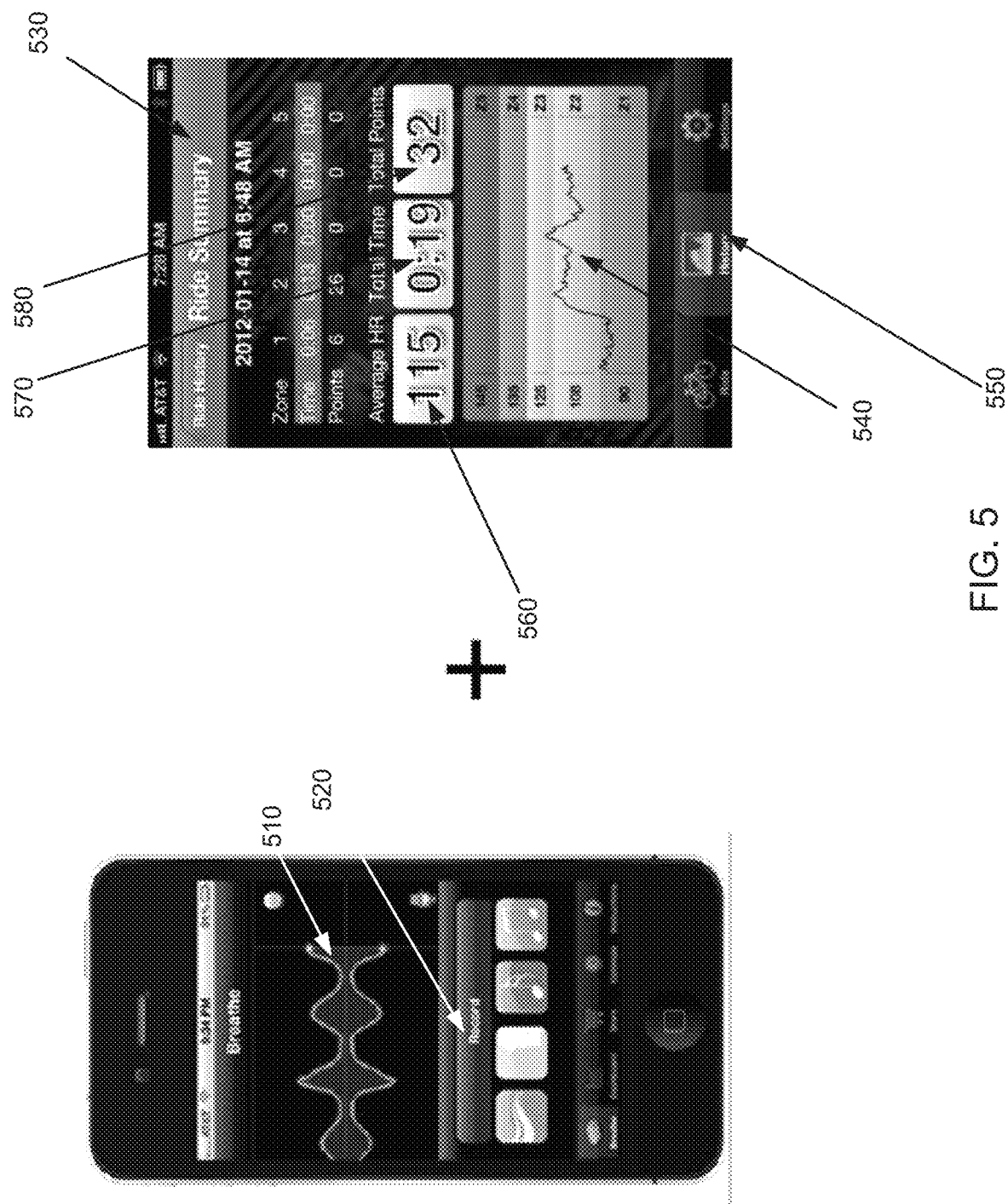
FIG. 5 shows electronic apparatus running software to determine VT and RCT according to an exemplary embodiment of the present invention.

FIG. 5 shows electronic apparatus running software to determine VT and RCT according to an exemplary embodiment of the present invention.

The software can both display the breathing patterns 510 and/or heart rate values 540 on the display screen of the electronic device. It can also save the heart rates, the breathing patterns and all of its related information contained in the users breathing onto the storage medium contained in the electronic device, computer or mobile device. In one embodiment, the user can be provided with an option to start recording the breathing pattern at the click of a push-button 520.

The software can then analyze the information obtained through the breathing sound measurements in order to determine the associated ventilatory (VT) and respiratory compensation (RCT) thresholds and their respective heart rate values from the heart monitor receiver. Research can be conducted to develop a relationship between breathing patterns and VT/RCT ratio. With this information, the software may be programmed with these relationships to provide an accurate estimate of the user's VT and RCT.

The software may be written in one or more computer programming codes and may be stored on a computer readable media. The software may include program code adapted to perform the various method steps as herein described.

The software could be used by itself to analyze any saved audio file that might have been taken from any recording device other than the electronic device having the microphone. If the user had a time line with heart rate values that corresponded to the saved audio file, they could use the software by itself to produce the intended result of the invention.

To use the embodiment of the invention illustrated in FIG. 2, a person would set up the electronic device 230 near the user who is exercising (typically on a stationary bike or a treadmill). They would have the user put a heart monitor 210 on their body, plug the heart monitor receiver 220 into the electronic device, and then begin the recording session by telling the software that the test has begun.

In one embodiment, the software can also collect and save information regarding the user's workout program. As shown in FIG. 5, for example, the software could display the user's ride summary 530 after the user is done exercising on a stationary bike. The user can access the ride summary after the ride by clicking on a "History" tab 550. The display under the "History" tab of the software can be programmed to show the user's average heart rate 560, the total time of the workout 570 and total points 580 accumulated by the user. The display can also be configured to show a graphical display 540 of the user's heart rate.

Once the user confirms that the test is complete, the software can perform the required analysis to determine ventilatory (VT) and respiratory compensation (RCT) thresholds and their related heart rates in Beats Per Minute (BPM).

Embodiments of the present invention could be used in the medical field or any field where ventilatory (VT) and respiratory compensation (RCT) thresholds are used to train athletes or diagnose medical conditions.

II. Dynamic Respiratory Classifier and Tracker (DRCT)

Embodiments of the present invention also provide a method and apparatus for performing respiratory acoustic analysis that uses inexpensive and readily available means for recording breathing sounds e.g. commercially available low-cost microphones. By comparison, conventional approaches require specialized sensors, tracheal or contact microphones, piezoelectric sensors etc.

Further, embodiments of the present invention provide a method and apparatus that takes into account full breath cycles. For example, the present invention can, in one embodiment, detect and separate the phases of the breath with exact timing, limits, etc.

In one embodiment, the present invention is a method and apparatus for dynamically classifying, analyzing, and tracking respiratory activity or human breathing. The present invention, in this embodiment, is aimed at the dynamic classification of a breathing session that includes breath phase and breath cycle analysis with the calculation of a set of metrics that help to characterize an individual's breathing pattern at rest. The analysis is based on audio processing of the breath signal. The audio serves as the main input source and all the extracted results, including the individual breath phase detection and analysis, are based on a series of procedures and calculations that are applied to the source audio input.

In one embodiment, the present invention detects and analyzes audio-extracted breath sounds from a full breath cycle, recognizing the different breath phases (inhale, transition, exhale, rest), detecting characteristics about the breath phases and the breath cycle such as inhale, pause, exhale, rest duration, the wheeze source and type (source of the constriction causing the wheeze can be either nasal or tracheal and the type of the constrictions can be either tension or wheezing) and cough type and source, choppiness and smoothness, attack and decay, etc. These breath cycle characteristics are obtained from the extraction of different audio descriptors from a respiratory audio signal and the performance of audio signal analysis on the descriptors.

In one embodiment, the present invention performs breath pattern statistical analysis on how the characteristics of the breath cycles of a recorded breath session fluctuate over time. For example, applying the mean and variance to breath phase and breath cycle durations, intensity, wheeze source and type, etc. to derive for example, the average respiratory rate, intensity, airway tension level, etc. and also to note when changes occur.

In one embodiment, the present invention provides metrics that are meaningful to user about breath pattern quality including respiratory rate, depth, tension, nasal and tracheal wheeze, pre-apnea and apnea, ramp (acceleration and deceleration), flow (choppiness or smoothness), variability, inhale/exhale ratios, time stamps for reach breath phase with other ratios, etc. by transforming and/or combining breath cycle characteristics and statistics. Metrics can come directly from breath cycle characteristics and statistics transformation and new metrics can be constructed by the combination of more than one characteristic (e.g., where breath phase duration, respiratory rate and breath intensity are used to obtain respiratory depth). Metrics can be provided for one breath cycle or for a number of breath cycles.

The overall procedure responsible for performing the detection and analysis of the audio-extracted breath sounds will be referred to hereinafter as the Dynamic Respiratory Classifier and Tracker ("DRCT").

II.A. Sound Capturing

Figure 6A:
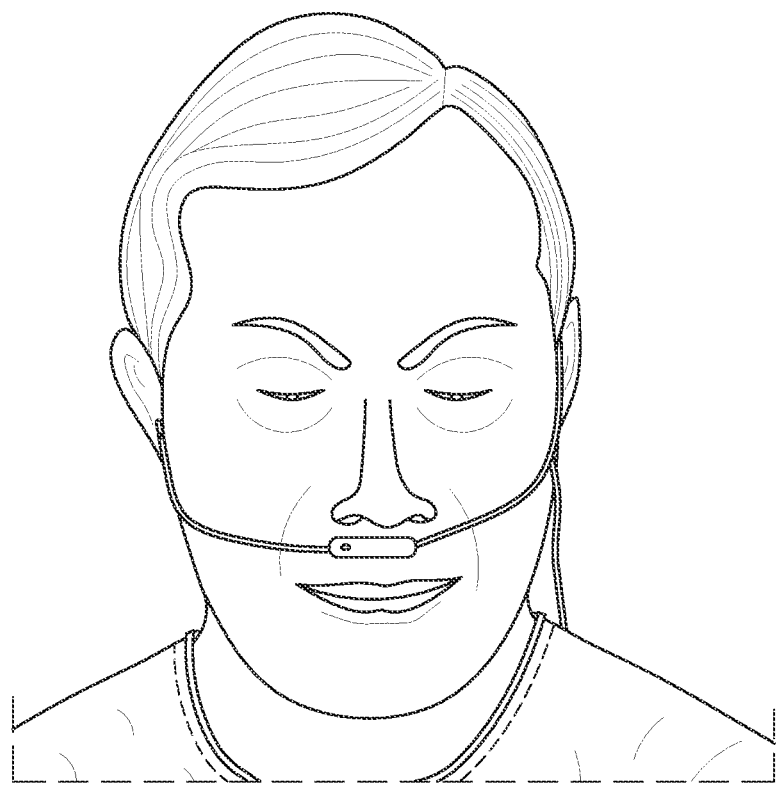
FIG. 6A illustrates an exemplary apparatus comprising a microphone for capturing breathing sounds in accordance with one embodiment of the present invention.

In one embodiment of the present invention, breath sounds are captured by a microphone. FIG. 6A illustrates an exemplary apparatus comprising a microphone for capturing breathing sounds in accordance with an embodiment of the present invention. These breath sounds can be captured at the nose or the mouth or both using an apparatus similar to the one illustrated in FIG. 6A. Further, in one embodiment, the sample rate used is 16 kHz, which is considered to be adequate both for breath phase detection and breath acoustic analysis. However, any sample rate higher than 16 kHz can also adequately be used.

Figure 6B:
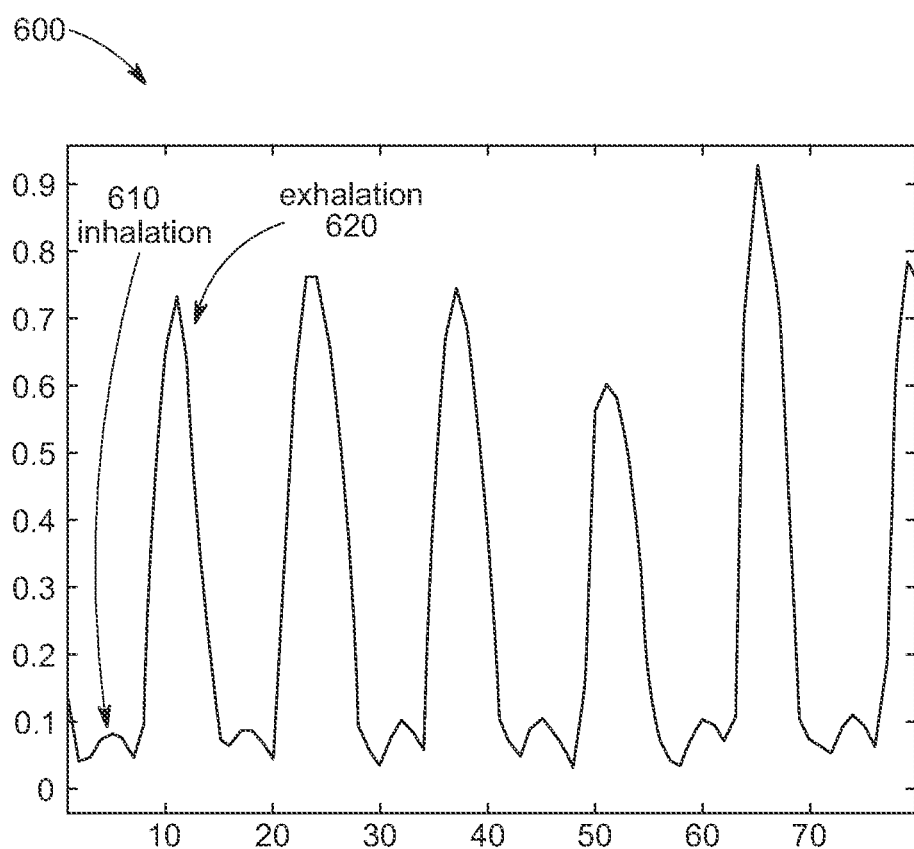
FIG. 6B illustrates an exemplary audio envelope extracted by filtering an input respiratory audio signal through a low-pass filter using an embodiment of the present invention.

The underlying principle that the DRCT procedure is based on is that airflow produces more pressure on the microphone membrane, and thus low frequencies are more apparent during this phase of exhalation. By contrast, higher frequency content is more apparent at the phase of inhalation, since there is no direct air pressure on the membrane. Accordingly, filtering the signal with a low-pass filter will attenuate the inhalation part while leaving the energy of exhalations almost unaffected. The goal of the filtering is typically to create an audio envelope that follows a specified pattern as illustrated in FIG. 6. FIG. 6 illustrates an exemplary audio envelope extracted by filtering an input respiratory audio signal through a low-pass filter using an embodiment of the present invention. Inhalation lobes 610 should be more attenuated than the exhalation lobes 620 in the envelope.

The DRCT procedure then classifies the lobes into two different classes that correspond to inhalation and exhalation. This classification can provide timestamps for each inhalation and exhalation event and for rest periods to be able to define a full breath cycle with four phases: inhalation, pause or transition, exhalation, and rest. These timestamps can be collected over several breath cycles.

II.B. The DRCT Low Layer Structure

Figure 7:
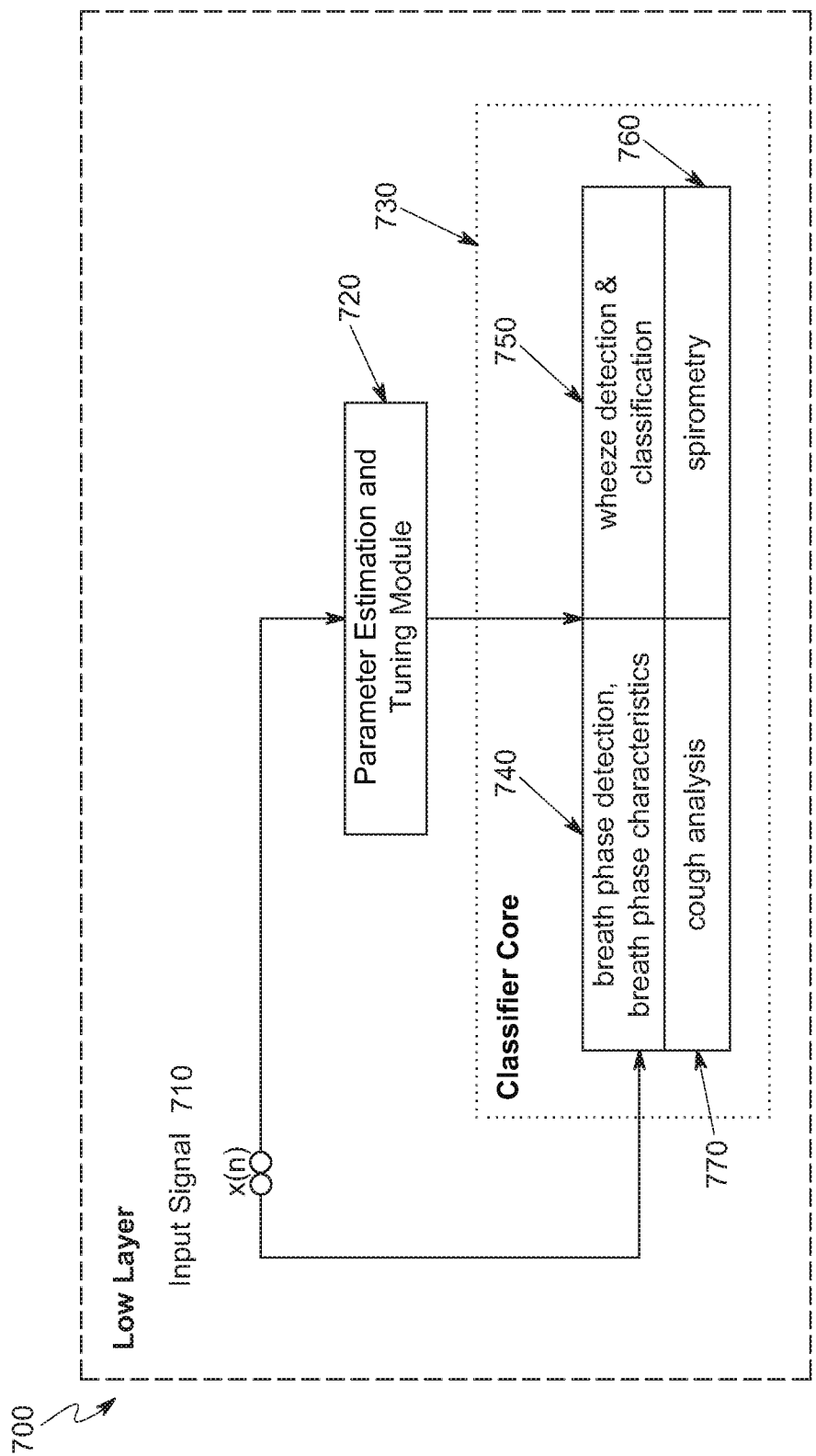
FIG. 7 illustrates a flowchart illustrating the overall structure of the lower layer of the DRCT procedure in accordance with one embodiment of the present invention.

FIG. 7 illustrates a flowchart illustrating the overall structure of the lower layer of the DRCT procedure in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 700 should not be construed as limiting the scope of the invention. Rather, it will be apparent to persons skilled in the relevant art(s) from the teachings provided herein that other functional flows are within the scope and spirit of the present invention. Flowchart 700 may be described with continued reference to exemplary embodiments described above, though the method is not limited to those embodiments.

The DRCT procedure comprises a low layer 700 and a high layer 1500. High layer 1500 will be discussed in connection with FIG. 15.

The low layer comprises a parameter estimation and tuning module 720. Parameter estimation and tuning (PET) module 720 comprises several sub-modules, which collectively shape the signal and its envelope accordingly and extract useful information and statistics that can be used by the sub-modules of the Classifier Core (CC) module 730. Both the PET module 720 and the CC module 730 operate on the input audio respiratory signal 710.

The CC module 730 comprises sub-modules that perform the annotation procedure responsible for classifying the breathing events e.g. wheeze detection etc. In one embodiment, the CC module 730 comprises a breath phase detection and breath phase characteristics module 740, a wheeze detection and classification module 750, a cough analysis module 770 and a spirometry module 760. The CC module 730 and each of its sub-modules will be described in further detailed below.

Figure 8:
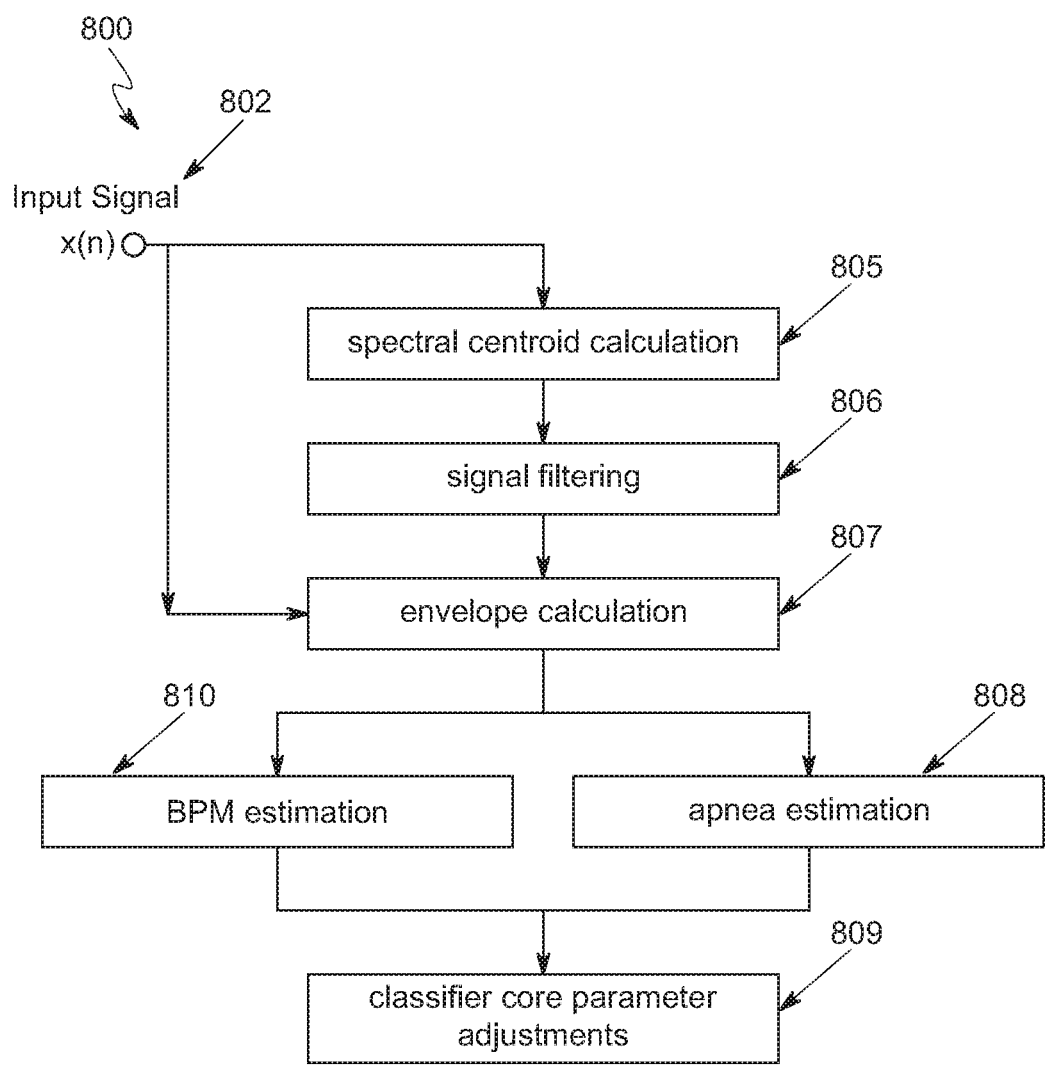
FIG. 8 depicts a flowchart illustrating an exemplary computer-implemented process for implementing the parameter estimation and tuning module shown in FIG. 7 in accordance with one embodiment of the present invention.

FIG. 8 depicts a flowchart 800 illustrating an exemplary computer-implemented process for implementing the parameter estimation and tuning module 720 from FIG. 7 in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 800 should not be construed as limiting the scope of the invention. Rather, it will be apparent to persons skilled in the relevant art(s) from the teachings provided herein that other functional flows are within the scope and spirit of the present invention. Flowchart 800 may be described with continued reference to exemplary embodiments described above, though the method is not limited to those embodiments.

In order to obtain the envelope shape as depicted in FIG. 6, power needs to be subtracted from the higher frequencies that correspond to inhalation sounds. In order to do this, the spectral centroid of each block of the audio input signal 802 needs to be calculated at step 805. The spectral centroid comprises information about the center of gravity of the audio spectrum.

By filtering the signal with a low pass filter tuned to the minimum value of the spectral centroid at step 806, frequencies above the tuning frequency, which usually corresponds to the threshold for inhalation sounds, can be attenuated and, as a result, the desirable envelope shape can be obtained.

At step 807, the envelope calculation is performed. The initial envelope calculation may be performed by using a relatively small window e.g. approximately 60 msec with a 50% overlap. By doing this, all the events that may happen during a breathing cycle e.g. a cough, can be captured and projected in detail. The signals fed into the envelope calculation stage 807 are the input signal and the low passed filtered signal from step 806.

The Breaths Per Minute ("BPM") estimation module 810 (or "respiratory rate" estimation module) analyzes the audio envelope from step 807 and estimates the breaths per minute by employing a sophisticated procedure that analyzes the autocorrelation function of the envelope. BPM estimation is used to adapt the window size that will later be used by the CC module 730. The larger the BPM value, the smaller the window size will likely be, in order to separate events that are close in time.

When the audio envelope is extracted in step 807, the periodicities of its pattern need to be determined in order to estimate the BPM value. To achieve this, the autocorrelation function (ACF) of the envelope is first calculated. The peak of the ACF indicates the period of the pattern repetition. Accordingly, the ACF can provide an estimation of the respiratory rate or BPM.

However, occasionally, environmental noises (usually sudden and unexpected audio events such as a cough) may distort the desirable shape of the ACF. As a result, choosing the highest peak value as a reference for BPM may provide a wrong estimation. Treating the ACF as a dataset, and finding the periodicity from this dataset can address this. In one embodiment, this is done by performing a FFT (Fast Fourier Transform) procedure of an oversampled by 8× and linearly interpolated ACF dataset. Oversampling increases the accuracy since the ACF data can be short. The estimated BPM is given by the location of the highest peak of the magnitude spectrum of the FFT of the oversampled ACF vector.

At step 808, apnea estimation is performed. Long pauses after exhalation are typically characteristic of a breath pattern commonly referred to as apnea. The overall BPM value is smaller in magnitude, thereby, indicating a large window size. The inhalations and exhalations are spaced differently in relation to the overall breath cycle duration and can affect the envelope calculation. Inhalations are very close to exhalations and in order to separate them, a smaller window size is needed in order to attain more precision in the temporal analysis of each breath phase. In particular, the apnea estimation module uses a threshold to detect the duration of silence in a breath signal. For example, if the duration of total silence is larger than the 30% threshold of the total signal duration, then the breath sample being examined may be classified as apnea or pre-apnea.

Finally, at step 809, the classifier code parameter adjustments module initializes and tunes the breath CC module 730 according to the parameters calculated by the PET module 720.

The parameters from the PET module 720 are inputted into the CC module 730 as shown in FIG. 7. The CC module 730 comprises, among other things, the breath phase detection and breath phase characteristics (hereinafter referred to as "BPD") module 740. The BPD module performs signal annotation and classification of the different breath phases and will be explained in further detail in connection with FIG. 9 below. An efficient procedure is employed in the BPD module to distinguish between signal presence and silence (breath rest or pause). Further, the BPD module can also efficiently discriminate between inhalation and exhalation.

The wheeze detection and classification (WDC) module 750 analyzes the input signal and detects wheezing. Wheezing typically comprises harmonic content. The WDC module 750 can be typically configured to be more robust and insensitive to environmental sounds that are harmonic with the exception of sounds that match several qualities of a wheezing sound e.g. alarm clocks, cell phones ringing etc.

The cough analysis module 770 employs procedures to successfully classify a given cough sample into different cough categories, and to detect possible lung or throat pathology, utilizing the analysis and qualities of the entire breath cycle and breath phases.

Spirometry is the most common of the pulmonary function tests, measuring lung function, specifically the amount (volume) and/or speed (flow) of air that can be inhaled or exhaled. The spirometry module 760 performs a spirometry analysis that can be performed on a single forced breath sample by using a set of extracted descriptors such as attack time, decay time, temporal centroid, and overall intensity.

Figure 9:
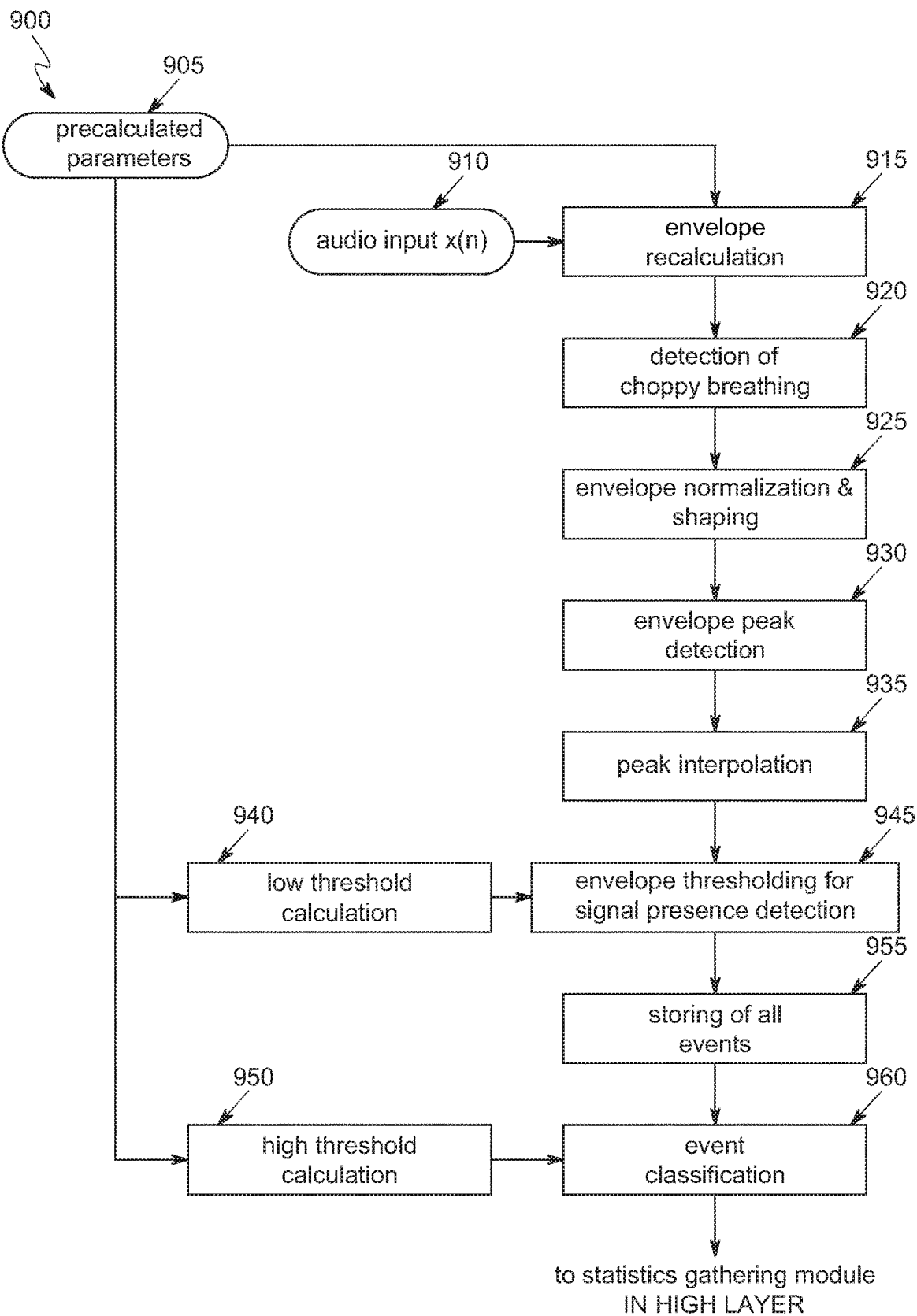
FIG. 9 depicts a flowchart illustrating an exemplary computer-implemented process for the breath phase detection and breath phase characteristics module (the BPD module) shown in FIG. 7 in accordance with one embodiment of the present invention.

FIG. 9 depicts a flowchart 900 illustrating an exemplary computer-implemented process for the breath phase detection and breath phase characteristics module (the BPD module 740) shown in FIG. 7 in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 900 should not be construed as limiting the scope of the invention. Rather, it will be apparent to persons skilled in the relevant art(s) from the teachings provided herein that other functional flows are within the scope and spirit of the present invention. Flowchart 900 may be described with continued reference to exemplary embodiments described above, though the method is not limited to those embodiments.

The BPD module uses several different submodules that are tuned according to the pre-gathered estimated statistics of the PET module 720. These precalculated parameters 905 along with the input audio signal 910 are used to perform an envelope recalculation at step 915. The envelope recalculation module at step 915 recalculates the envelope using a window which has a size set according to the previously estimated BPM and taking into account the existence of possible apnea. The BPM value provides an indication of how close one breath phase is to another and how accurate the timing needs to be. Typically, a suitable window size will eliminate changes in envelope that do not come from choppy breathing, but rather from sudden and slight microphone placement changes. The placement changes may happen throughout a recording and, consequently, determining an appropriate window setting is important.

At step 920, the BPD module performs a detection for choppy breathing. The slopes of the envelope during a segment corresponding to the current breath phase is examined. The BPD module attempts to determine if more than one convex or concave peak exists during a breath phase. For example, if the inhalation or exhalation has a choppy rather than smooth quality, consecutive inhalations or exhalations are very close to one another. In such a case, the BPD module will merge them under a unique envelope lobe so that they are separated and treated as more than one consecutive breath phase of the same kind. The ability to detect, count, and measure choppy breathing events results in better BPM analysis as well as provides important information about the characteristic and quality of breathing.

At step 925, the BPD module performs envelope normalization and shaping. Further, DC offset removal takes place also. DC typically corresponds to environmental hum noise, thus a type of noise filtering is effectuated.

At step 930, envelope peak detection is performed by the BPD module. The peaks of the envelope, both concave and convex, in order to determine the start and end timestamps of each breath cycle, and to gather the peak values that will be fed into the high threshold calculation module at step 950.

At step 935, a peak interpolation is performed. A new interpolated envelope is created. This new envelope is a filtered envelope version that does not have false peaks created as a result of environmental noise.

A low threshold is then calculated at step 940 and a high threshold is calculated at step 950. The low threshold calculated at step 940 is responsible for detecting signal presence. Accordingly, it detects all events, both inhalations and exhalations. The higher threshold calculated at step 950 is used to discriminate between inhalation and exhalation events. The two thresholds are calculated by using moving average filters on the interpolated envelope. The functional difference between these two filters, in one embodiment, is that for the high threshold determination, the moving average filter uses a variable sample rate since it typically uses envelope peaks as input, whereas for the low threshold determination, the moving average filter uses all the envelope samples.

At step 945, envelope thresholding is performed for signal presence detection. As discussed above, the low threshold is used to detect all the events, while the high threshold is used to discriminate between inhalation and exhalation events.

At step 955, a storing of all detected events takes place and at step 960 the stored events are classified. The information regarding the events is then transmitted for statistics gathering in high layer 1500.

In one embodiment, the CC module 730 also comprises the WDC module 750. In contrast to conventional approaches that use expensive equipment for breath sound capturing and computationally expensive image analysis procedure that detect heavy wheezing, the present invention is advantageously able to not only detect wheezing events, but also able to classify them according to their nature as tension or wheezing of different magnitude (from light to heavy), by using a relatively less computationally intensive approach that also performs the analysis in real-time.

The framework for the WDC module 750 is based on a time frequency analysis of the auditory signal. The analysis performed by the WDC module 750 is able to detect periodic patterns in the signal and to classify them according to their spectrum. The premise underlying the analysis that makes wheeze detection possible is that when constrictions occur in several areas of the respiratory system, different kinds of lobes rise in the frequency spectrum as a result of air resonating in the constrictions and cavities that may exist. These lobes are characterized according to their magnitude, location and width by the WDC module 750. Furthermore, the relationship between consecutive spectrums can be useful for constriction classification.

In one embodiment, an important descriptor that helps to determine the nature of the wheezing sound is the amount of change between consecutive spectrums or blocks also called a similarity descriptor. The similarity descriptor is used by the WDC module 750 to determine if an event should be considered. For example, a sudden event that features harmonic content and does not last as long as a wheeze event is ignored. Even if the harmonic pattern comes from the lungs or the vocal tract of the subject, it is not identified as a pathology if it is that short, e.g., less than 2 consecutive blocks that sum up to 200 msec of duration. Also, important to note for purposes of tension classification is that tension tends to produce frequency spectrums richer in high frequencies with wider lobes as the constrictions do not form cavities that would result in distinct frequencies.

Figure 10:
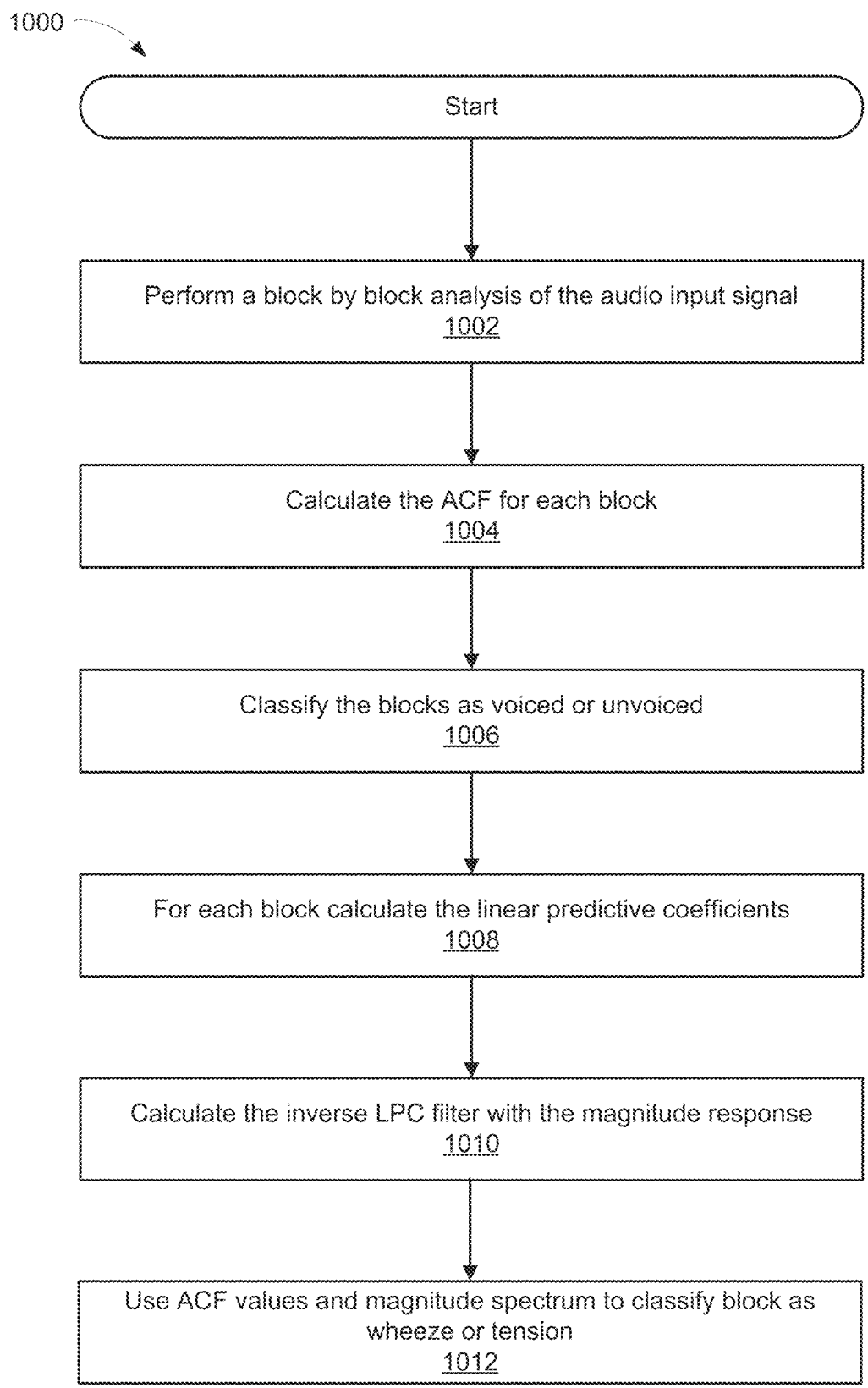
FIG. 10 depicts a flowchart illustrating an exemplary computer-implemented process for the wheeze detection and classification module (WDC module) from FIG. 7 in accordance with one embodiment of the present invention.

FIG. 10 depicts a flowchart 1000 illustrating an exemplary computer-implemented process for the wheeze detection and classification module (WDC module 750) from FIG. 7 in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 1000 should not be construed as limiting the scope of the invention. Rather, it will be apparent to persons skilled in the relevant art(s) from the teachings provided herein that other functional flows are within the scope and spirit of the present invention. Flowchart 1000 may be described with continued reference to exemplary embodiments described above, though the method is not limited to those embodiments.

In one embodiment, at step 1002, the WDC module 750 performs a block by block analysis of the audio signal 710 with a window which is 2048 samples long (approximately 12 msec for the operating sample rate of 16 Khz) and a 50% overlap factor.

At step 1004, for each block, the ACF is calculated. If the maximum of the normalized ACF of the block under analysis (excluding the first value that corresponds to zero time-lag) is above 0.5, then the block is considered to be "voiced."

By using this information, at step 1006, the WDC module 750 is able to classify the blocks as voiced and unvoiced. By further extension of this procedure, in one embodiment, the WDC module 750 is able to classify even more incoming blocks as clearly voiced, possibly voiced and unvoiced. Typically, a clean breath sound that does not feature any possible harmonic component (and therefore comprises no wheezing at all) should show near noise characteristics, which means that the ACF values will be really low.

Tension in breathing is typically not able to produce clear harmonic patterns. Blocks wherein the maximum value of the normalized ACF is between 0.15-3 will typically be classified as "tension" blocks.

Incoming blocks wherein the maximum value of the normalized ACF is above 0.3 are considered to typically be "voiced" or "wheeze" blocks.

Following this process, in one embodiment, all blocks are processed again for further evaluation. At step 1008, for each block, the linear predictive coding (LPC) coefficients are calculated using the Levinson-Durbin process. Subsequently, at step 1010, the inverse LPC filter is calculated with its magnitude response. The magnitude response is then inspected.

Tension typically produces high frequency content with wide lobes in the magnitude spectrum since the pattern is not clearly harmonic. On the other hand, lobes resulting from wheezing are more narrow and usually occur in lower frequencies in the spectrum.

Figure 11A:
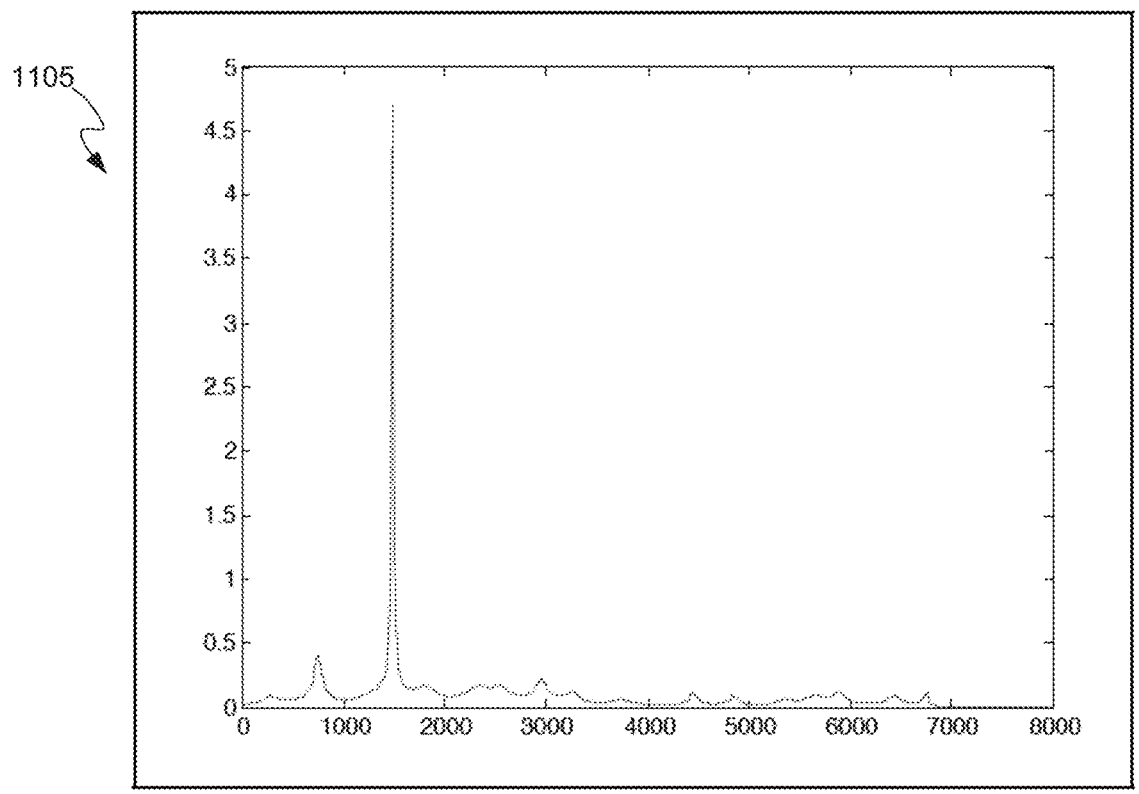
FIG. 11A illustrates a spectral pattern showing pure wheezing.

FIG. 11A illustrates a spectral pattern showing pure wheezing. The WDC module 750 would likely identify spectral pattern 1105 to be associated with wheezing resulting from a single constriction in the trachea because of the single narrow lobe and the lower frequency at which the lobe occurs.

Figure 11B:
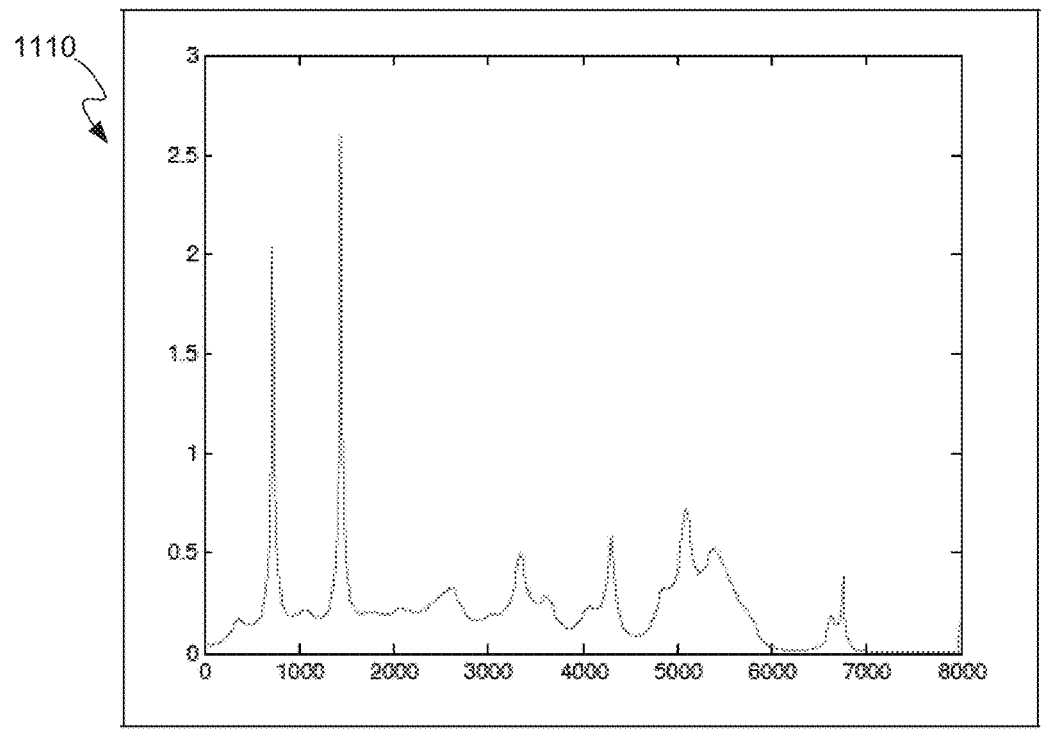
FIG. 11B illustrates a spectral pattern showing wheezing in which more than one constriction is apparent.

FIG. 11B illustrates a spectral pattern showing wheezing in which more than one constriction is apparent. Spectral pattern 1110 illustrates multiple narrow lobes in the lower frequencies that the WDC module 750 will likely identify as wheezing resulting from multiple constrictions in the trachea. The higher frequency content above 3000 Hz in spectral pattern 1110 may also be associated with tension.

Figure 12A:
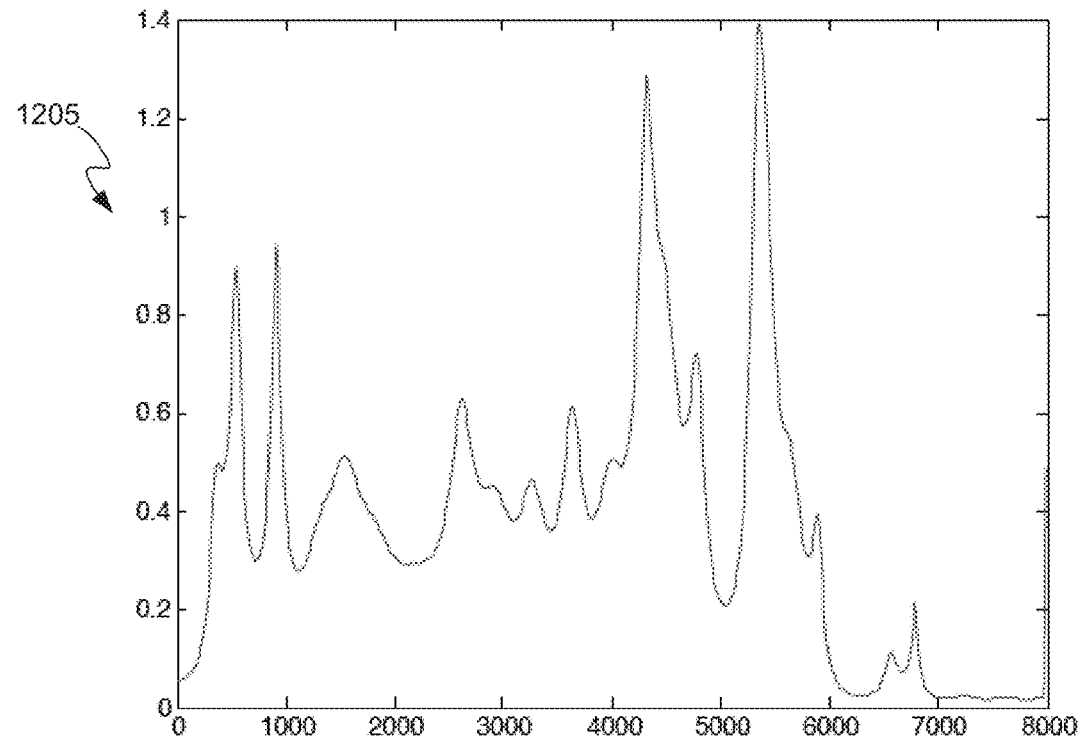
FIG. 12A illustrates a first spectral pattern showing tension created by tracheal constrictions.

FIG. 12A illustrates a first spectral pattern showing tension created by tracheal constrictions. Spectral pattern 1205 illustrates rich frequency content and wide lobes above 3000 Hz, which will likely be identified as tension resulting from multiple tracheal constrictions by the WDC module 750.

Figure 12B:
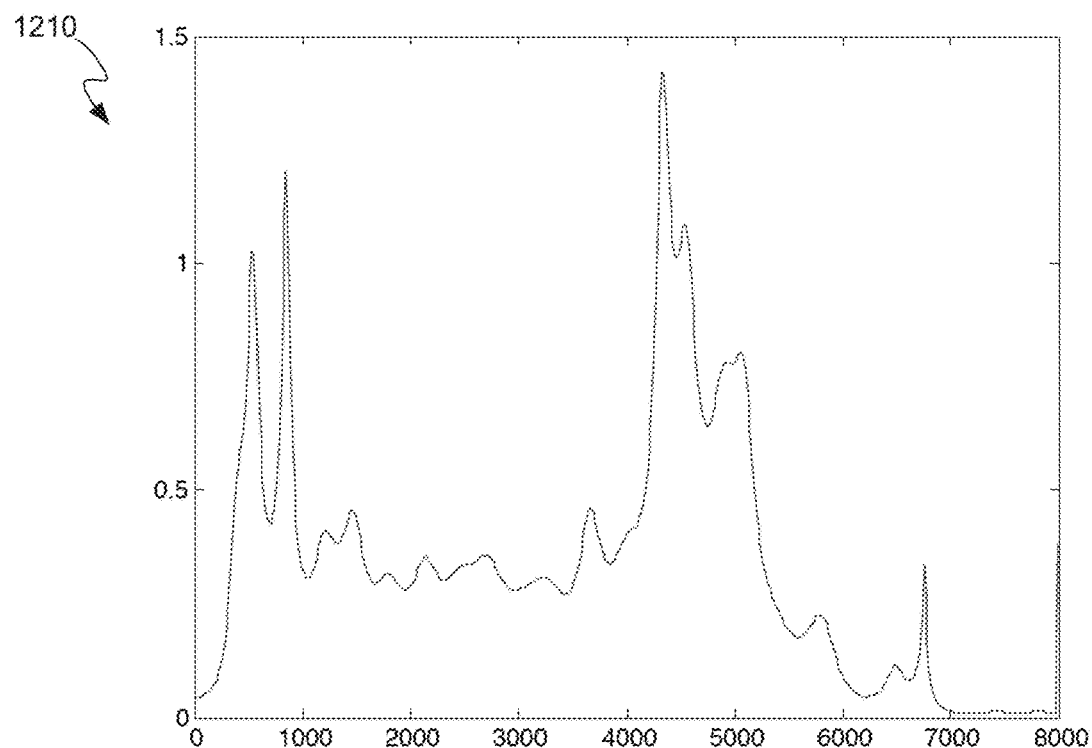
FIG. 12B illustrates a second spectral pattern showing tension created by tracheal constrictions.

FIG. 12B illustrates a second spectral pattern showing tension created by tracheal constrictions. Similar to spectral pattern 1205, spectral pattern 1210 illustrates wide lobes and rich frequency content above 3000 Hz, which will likely be identified as tension resulting from multiple tracheal constrictions by the WDC module 750.

Finally, at step 1012 in FIG. 10, a decision procedure that takes into account maximum ACF values and LPC magnitude spectrum lobe location and width will typically be employed by the WDC module 750 to determine whether the block should be classified as wheeze or tension.

The spectral centroid descriptor may, in one embodiment, be employed as a meter of spectrum gravity towards lower or higher frequencies. In one embodiment, the ratio of the high and low band of the magnitude spectrum may also be examined. A formula that may be used to decide whether to classify a block as wheeze or tension may be the following:

$$n.a.l.w \cdot \left( \alpha \cdot m_{ACF} + (1-\alpha) \frac{B_h}{B_l} \right) \underset{H_1}{\overset{H_0}{\gtrless}} \lambda$$

where $H_0$ corresponds to wheeze, $H_1$ corresponds to tension, n.a.l.w corresponds to normalized average lobe width, $B_h$ corresponds to high band energy, $B_l$ corresponds to low band energy, $\alpha$ is a weight factor, and $\lambda$ is a suitably chosen threshold based on the training set.

In most cases constrictions in the trachea can be complicated. Accordingly, constrictions in the trachea will result in a richer spectrum with more harmonics and fundamental frequencies, each one corresponding a different constriction. By comparison, nasal constrictions produce less frequencies with fewer harmonics. The WDC module 750, in one embodiment, can determine whether the wheeze is nasal or tracheal by counting the number of produced harmonics.

Figure 13A:
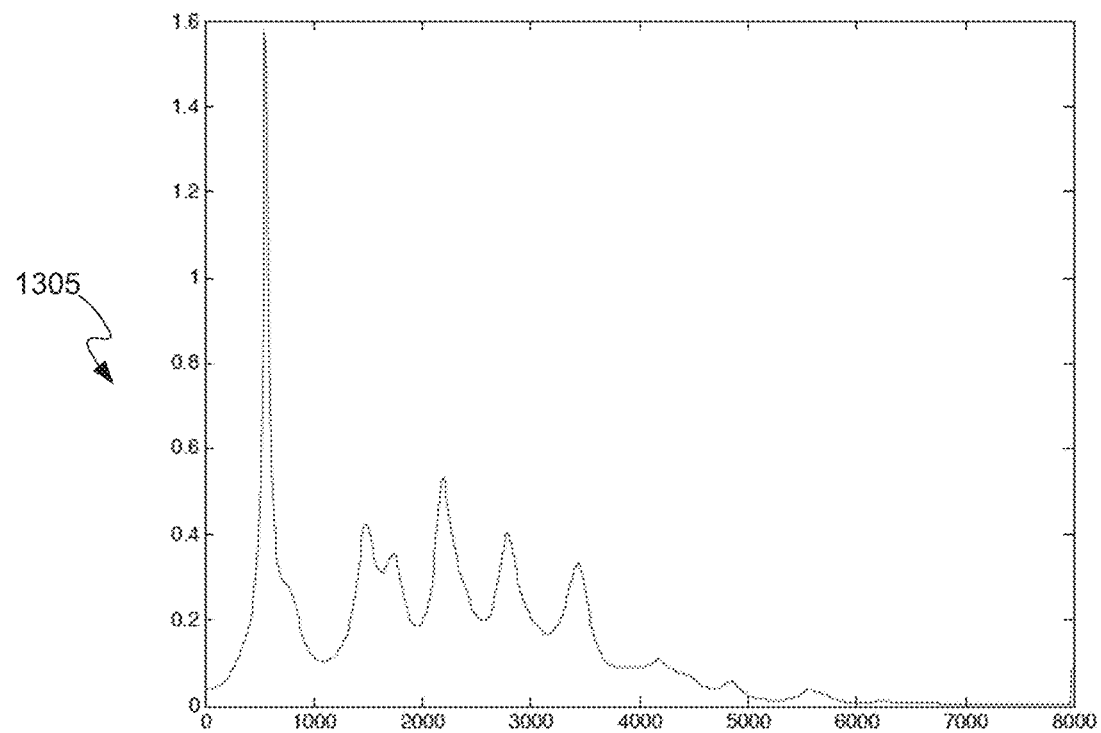
FIG. 13A illustrates a spectral pattern showing wheezing created as a result of nasal constrictions.

FIG. 13A illustrates a spectral pattern showing wheezing created as a result of nasal constrictions. As seen in FIG. 13A, spectral pattern 1305 is characterized by a narrow lobe occurring at a lower frequency value and overall fewer harmonics as compared against FIGS. 11A and 11B. Accordingly, WDC module 750 can identify it as resulting from a wheeze produced due to one or more nasal constrictions.

Figure 13B:
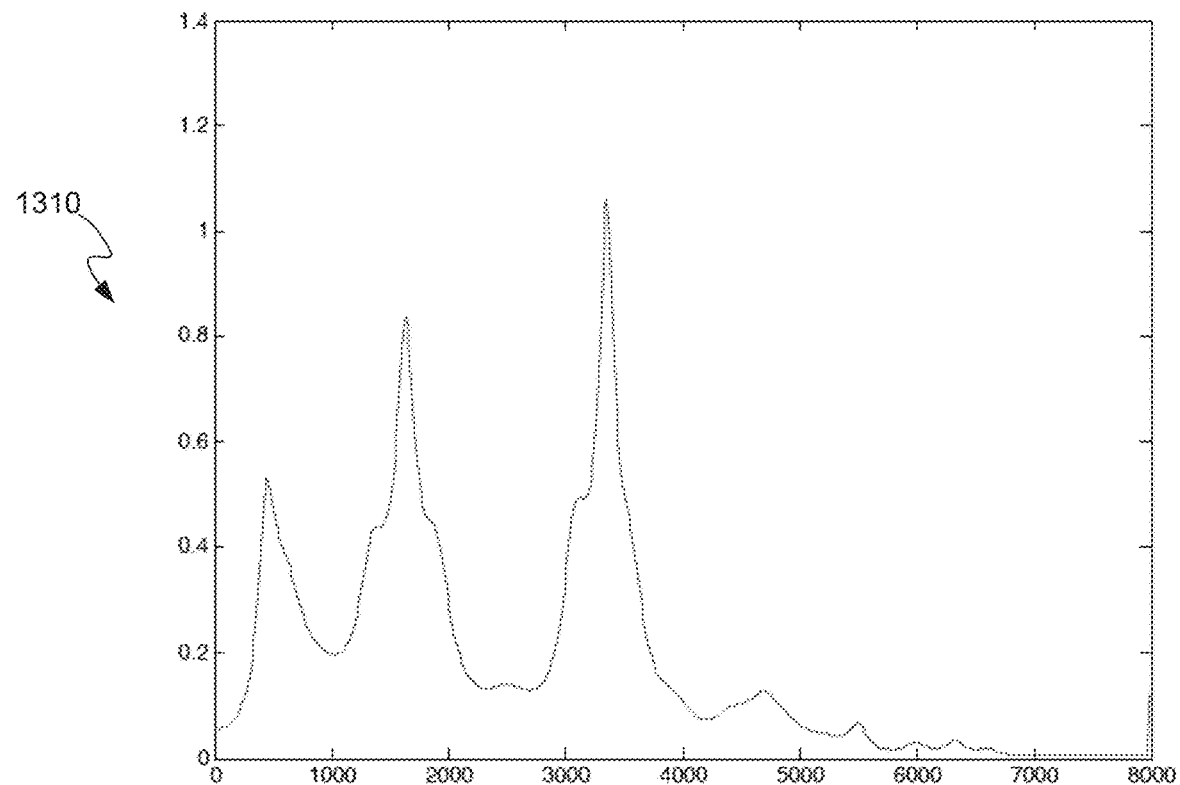
FIG. 13B illustrates a spectral pattern showing tension created as a result of nasal constrictions.

FIG. 13B illustrates a spectral pattern showing tension created as a result of nasal constrictions. As seen in FIG. 13B, spectral pattern 1310 is characterized by wider lobes in the higher frequencies and overall fewer harmonics as compared with FIGS. 12A and 12B. Accordingly, WDC module 750 can identify it as resulting from tension produced due to one or more nasal constrictions.

In one embodiment, the CC module 730 also comprises the cough analysis module 770, which provides a procedure for performing cough analysis. The cough analysis module 770 employs methods in order to successfully classify a given cough sample into different cough categories, and to detect possible lung or throat pathology by utilizing the analysis and qualities of the entire breath cycle and the breath phases.

Coughs can be classified into several different categories. These categories can further be separated into subcategories regarding the cough pattern and the cough's sound properties. Categories based on the cough sound properties include the following: dry cough, wet cough, slow rising, fast rising, slow decay, fast decay. Categories based on the cough pattern can be separate into the following: one shot or repetitive, e.g., barking cough.

Other important properties that can provide important information about the lung and throat health comprise the retrigger time and inhalation quality. Retrigger time is the time it takes for a subject to inhale in order to trigger the next cough in a repetitive pattern. Retrigger time typically indicates how well the respiratory muscles function.

The inhalation quality can be determined by performing a wheeze analysis on the portion of the auditory signal that provides information to indicate if there is respiratory tension or damage. For example, a wheezing analysis on the inhalation before the cough takes place, combined with the analysis of the cough's tail, will generate descriptors that can be used to decide if the cough is a whooping cough. Furthermore, the cough's sound can be separated into two components: a harmonic one and a noisy one. In whooping cough, subjects find it difficult to inhale and, accordingly, the harmonic part of the sound will rise up faster than the noisy part, which is usually predominant in healthy subjects. The ratio of the harmonic and noisy slopes can be used to determine if a cough is a whooping cough.

Figure 14:
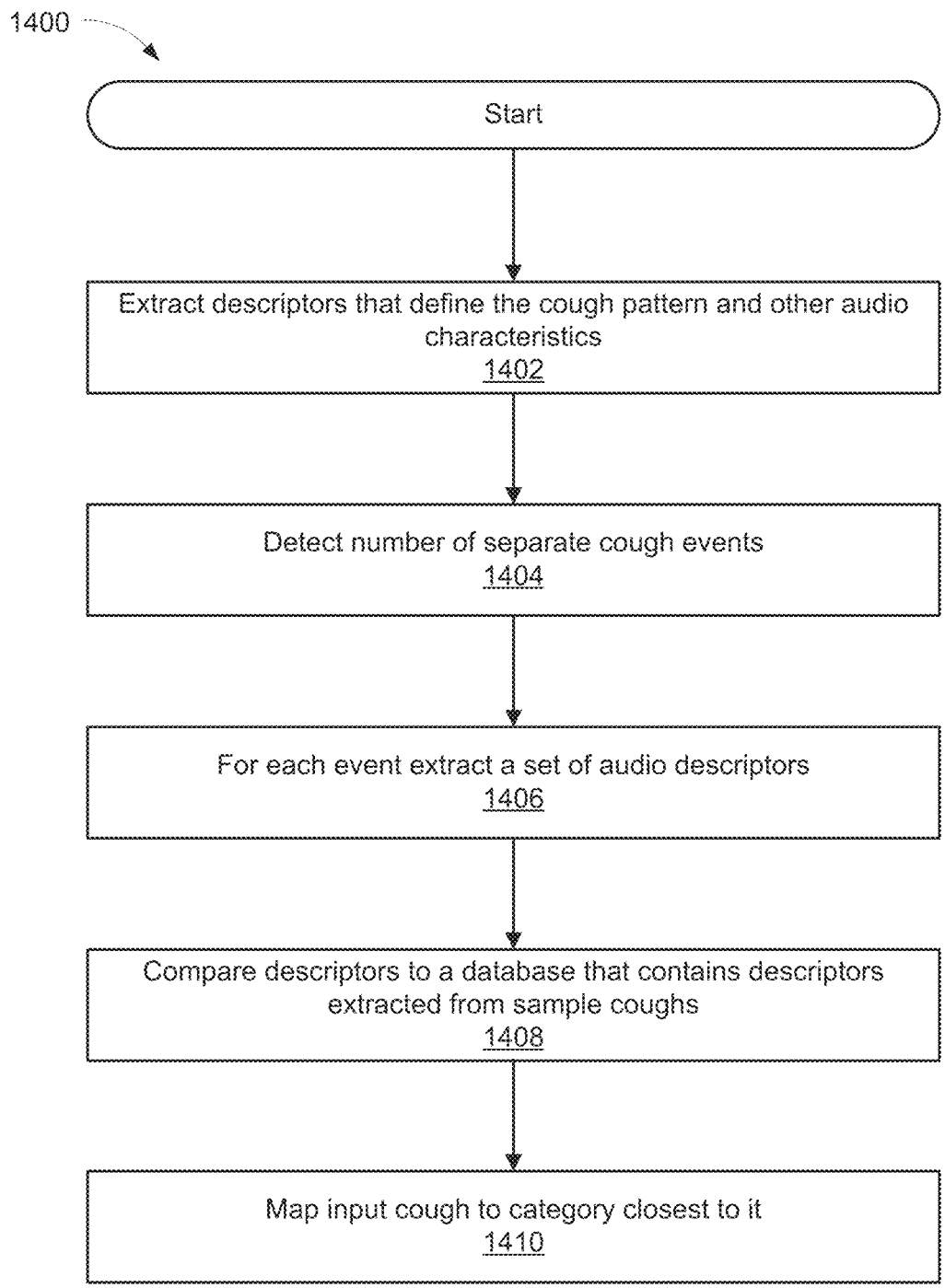
FIG. 14 depicts a flowchart illustrating an exemplary computer-implemented process for the cough analysis module 770 shown in FIG. 7 in accordance with one embodiment of the present invention.

FIG. 14 depicts a flowchart 1400 illustrating an exemplary computer-implemented process for the cough analysis module 770 shown in FIG. 7 in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 1400 should not be construed as limiting the scope of the invention. Rather, it will be apparent to persons skilled in the relevant art(s) from the teachings provided herein that other functional flows are within the scope and spirit of the present invention. Flowchart 1400 may be described with continued reference to exemplary embodiments described above, though the method is not limited to those embodiments.

In order to perform cough analysis, at step 1402, the cough analysis module 770 first uses the audio input signal 710 to extract a set of descriptors that will both define the cough's pattern plus other audio characteristics and properties.

At step 1404, the number of separate cough events is detected. If more than one event is detected, for example, then the analysis module 770 must determine if there is a repetitive cough pattern. For each one of the events, at step 1406, a set of audio descriptors is extracted such as attack time, decay time, envelope intensity, spectral centroid, spectral spread, spectral kyrtosis, harmonicity, etc.

At step 1408, these audio descriptors are compared to a database that contains descriptors extracted from sample coughs of the subject. Finally, at step 1410, the input cough is mapped to the category closest to it. In this way the present invention advantageously customizes the cough analysis using the subject's own cough.

A cough can typically be separated into two parts. The attack time part, which is the percussive sound of the cough, and the tail (decay time part). Both of these two parts can be analyzed separately. In one embodiment, a full wheeze analysis can be carried out on the tail to determine pathology related to asthma. Further, the analysis on the percussive part of the cough can be indicative of the condition of the lung tissue and respiratory muscles.

Finally, in one embodiment, the CC module 730 also comprises the spirometry module 760. Spirometry is the most common of the pulmonary function tests, measuring lung function, specifically the amount (volume) and/or speed (flow) of air that can be inhaled or exhaled. Descriptors such as intensity, attack and decay time, combined with wheeze analysis can be used as well for spirometry with an appropriate setting for a microphone installation and a standardized sample database. The analysis is performed on a single forced breath sample typically. The procedure initially extracts a set of descriptors such as attack time, decay time, temporal centroid, and overall intensity. Then the sample is classified into one of the designated categories, which have been pre-defined in terms of their descriptors, using the minimum distance.

II.C. The DRCT High Layer Structure

As discussed above, the DRCT procedure comprises a low layer 700 and a high layer 1500. Once the low-level analysis of the CC module 370 is complete, a set of vectors and arrays containing the results from the direct signal processing is passed on to the high layer 1500 also known as the post-parsing and data write-out layer of the design. This layer performs a number of post-processing operations on the raw data and extracts the final statistics and scores. Further, in one embodiment, it publishes the extracted statistics and scores by performing an XML write-out. The techniques used in post-processing will typically depend on the results from low level 700. Stated differently, the vectors of low-level analysis data from low layer 700 are processed by high layer 1500, mapped to their corresponding detected breath cycles, and statistics are extracted.

Figure 15:
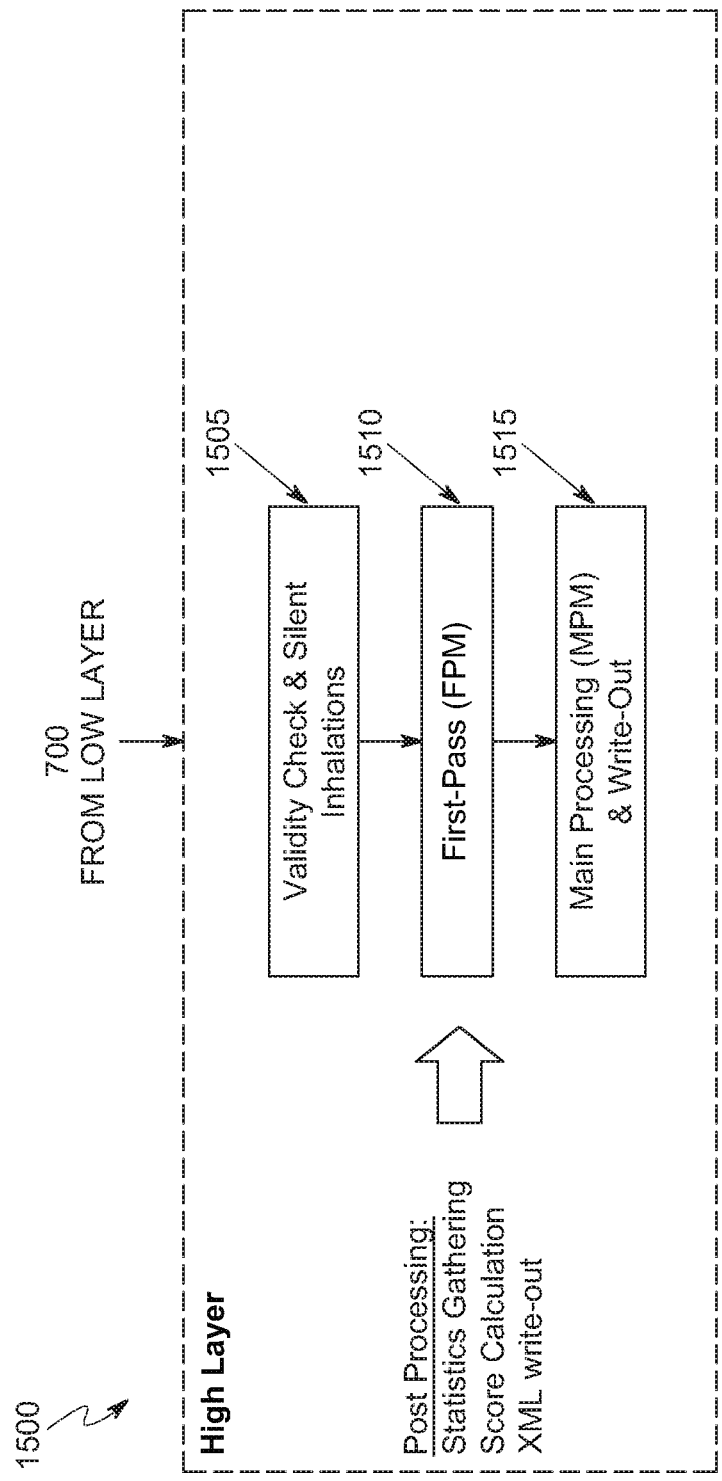
FIG. 15 illustrates a flowchart illustrating an exemplary structure of the high layer of the computer-implemented DRCT procedure in accordance with one embodiment of the present invention.

FIG. 15 illustrates a flowchart 1500 illustrating an exemplary structure of the high layer of the computer-implemented DRCT procedure in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 1500 should not be construed as limiting the scope of the invention. Rather, it will be apparent to persons skilled in the relevant art(s) from the teachings provided herein that other functional flows are within the scope and spirit of the present invention. Flowchart 1500 may be described with continued reference to exemplary embodiments described above, though the method is not limited to those embodiments.

At step 1505, a validity check is performed. The arrays from low layer 700 are checked for validity in terms of size and value range.

Further, depending on the silent inhalation flag and the compensation module activation, a pre-parsing of the detected breath cycle takes place. This includes checking for consecutive similar events, and focusing on the exhalation detection. The DRCT high layer procedure 1500, in one embodiment, tries to recreate a temporal plan of the distribution of the inhalations and to create an estimated full cycle vector (all breath events) to be used for the analysis. It should be noted that this procedure is only enabled when the information regarding the inhalations is so minimal or weak that full analysis would be impossible.

The first-pass module (FPM) at step 1510 comprises a stripped down version of the whole high-level module containing only the breath cycle event-based BPM (or RR) estimation. A FPM respiratory threshold is extracted and used in the second pass for threshold adjustments. This module enables the system to adjust and perform for sessions with a wide range of BPMs in a dynamic, session-specific manner.

The main process module (MPM) at step 1515 performs breath cycle separation which is done by event grouping. The MPM module processes a sequence vector with the event types, and outputs a breath cycle vector containing the map of all the events. Based on this separation, the MPM module performs a calculation of the full set of metrics by integrating auxiliary vectors related to the breath intensity, the wheeze, etc. into the breath cycle mapping. The following metrics are calculated per breath cycle and as a session average in the end for overall session analysis:

A) Average Respiratory Rate: The respiratory rate shows how fast or slow is the breathing in the session.

B) Respiratory Rate Variance: The variance refers to the deviation of each breath cycle from the session average. This is an indicator of the overall stability of the breathing patterns.

C) Deep/Shallow Metric: The depth of the breath is extracted mainly using the calculated duration and power intensity of each breath cycle.

D) Wheeze and Tension: Respiratory tension indicates the level of openness or constriction of the upper airways and throat. Nasal wheezing can indicate restriction or obstruction in the nasal passageways. Tracheal wheezing can indicate restriction or obstruction in the lungs. These are distinguished by a combination of intensity, duration and frequency content of the detected wheeze blocks.

E) Apnea refers to pauses of 10 seconds or more in between breaths following exhalation.

F) Pre-Apnea: Pre-Apnea refers to a pause of 2.5 seconds to 9.5 seconds and can be seen during waking hours, as well as be a precursor for clinical apnea.

G) Inhalation/Exhalation Ratio (IER): This is the ratio of the duration of the inhalation versus exhalation. These durations and their connection can help to extract conclusions about the breath patterns, specially concerning the physical state of the user. Other ratios can also be extracted such as the time of any one phase over the time of the total breath cycle. For example, the time of inhalation in relation to the time of the total breath cycle (Ti/Ttotal). These durations can indicate the physiological state of the user and can be correlated with physical and psychological indications and diagnosis.

H) Respiratory Flow: This metric indicates how choppy or smooth the breathing is. Choppy and smooth breathing patterns can have physical and physiological implications. For example, choppy breathing can indicate a disturbance in the respiratory movement musculature, the brain and nervous system, or the emotional state of the individual.

I) Number of Breaths: This metric is used to evaluate the validity of the session's results. Since analysis is displayed per breath cycle and as an average, the larger the number of cycles detected, the more statistically accurate the results will be.

The high layer 1500 will store all the statistics along with the breath phase durations for each breath cycle in an XML file that will be used to display the information to a user of the system.

II.D. Ventilatory Threshold and Respiratory Compensation Threshold Detection within the DRCT Framework The conventional protocol for metabolic testing is to measure gas exchange values at rest for a specific duration and as the patient begins exercising with incremental power and intensity increases for specific time durations. The metabolic chart tracks how the gas exchange values change. In order to accomplish this with the respiratory acoustic analysis system of the present invention, first the breath phases, the breath cycle, and all the descriptors that characterize breathing at rest need to be determined using the DRCT framework described above. Then the change in the relevant descriptors can be tracked as the patient begins to exercise and increases exercise intensity.

The respiratory acoustic analysis system of the present invention is an alternative to the gas exchange methods which require a high level of precision, attention to detail and equipment that is quite expensive, all of which can be outside the range and skill set of the ordinary health fitness and clinical exercise physiology community. Alternatively, the present invention uses sounds created by the air moving into and out of the respiratory system. By analyzing breath sounds to detect breath cycle phases and frequency, volume, flow, and other characteristics, it is possible to characterize breathing at rest and during different exercise intensities to determine ventilatory thresholds.

The measurement of the ventilatory thresholds including but not limited to VT-aerobic (T1) and respiratory compensation (RCT-lactate or anaerobic, T2) thresholds and $VO_2$ Max using respiratory gas exchange is a standard diagnostic tool in exercise laboratories and is capable of defining important markers of sustainable exercise capacity, which may then be linked to the power output (PO) or heart rate (HR) response for training prescription. Measurement of respiratory gas exchange is cumbersome and expensive. Other important measurements that can be derived from respiratory gas exchange analysis include the amount of $O_2$ absorption in the blood and tissues, $VO_2$ max, the amount of fats and glucose utilized in metabolism.

Since the calculation of these metabolic thresholds is grounded in the volume, rate and pattern of breathing, as discussed in Section I. above, it is possible to use microphones to detect the breath sounds and acoustic analysis to derive estimates of ventilatory thresholds such as, but not limited to VT (T1) and RCT (T2), $O_2$ absorption, $VO_2$ MAX, the amount of fats and/or glucose utilized in metabolism at rest during incremental exercise and during all exercise intensities.

In one embodiment of the present invention, different subsets of the extracted metrics are used in the high layer 1500 to analyze and classify breathing patterns during different exercise intensities and during pulmonary testing. The high layer 1500 can be used, in one embodiment, to process the descriptor sequences from the low layer 700 by employing custom detection procedures in order to decide when the ventilatory thresholds occur. As discussed above, one embodiment of the present invention can be used to determine VT (T1) and RCT (T2). In a different embodiment, VT and RCT calculations can be made within the classifier core module 730 itself. Processes such as respiratory rate tracking and breath phase tracking and detection are important in the analysis as the final result is not only based on the overall breath sound statistics, but also on statistics that come from the analysis of each breath cycle as the breathing session progresses over time (e.g. inhalation intensity tracking).

Figure 16:
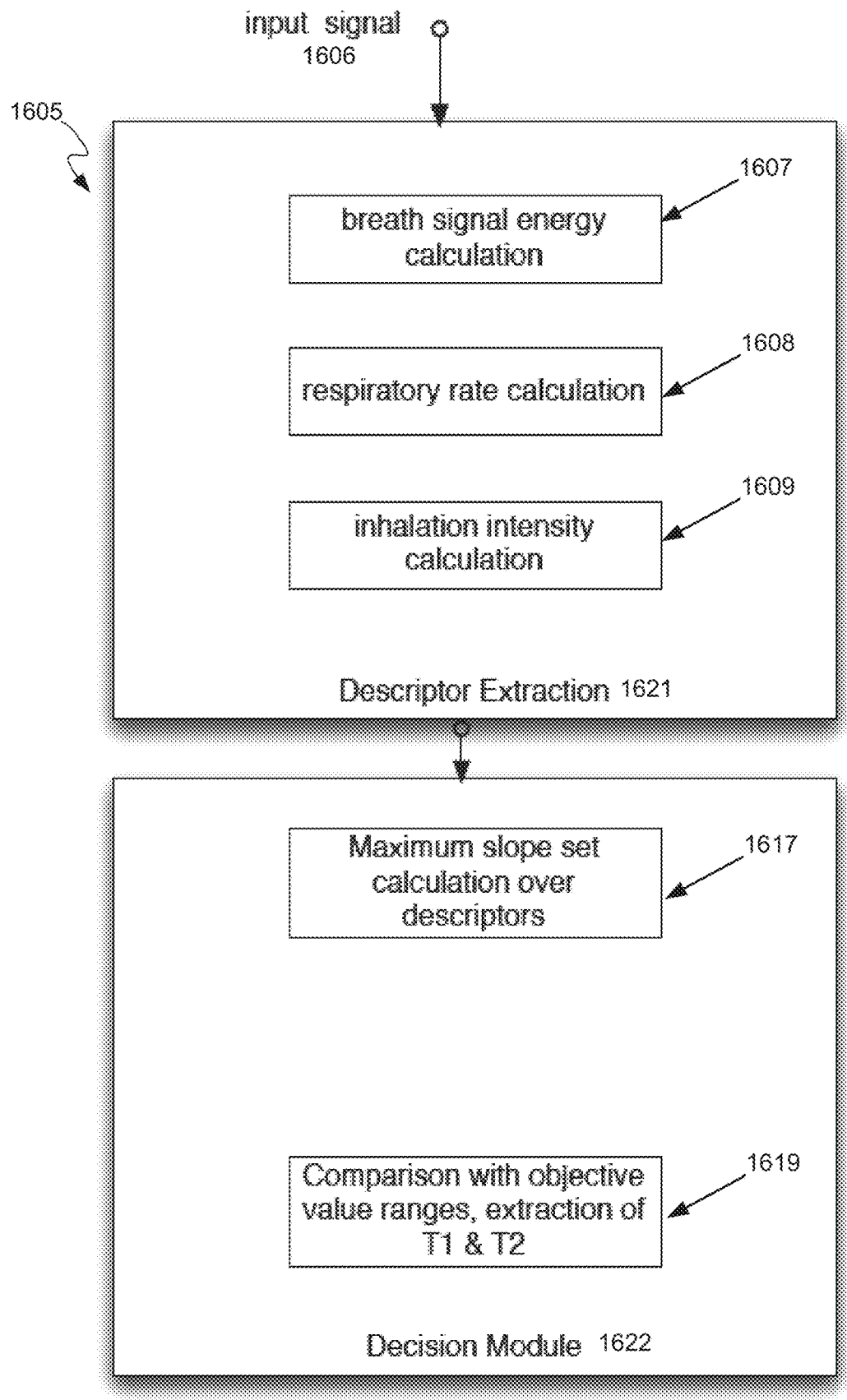
FIG. 16 depicts a framework for the ventilatory threshold calculation module in accordance with one embodiment of the present invention.

FIG. 16 depicts a framework 1605 for the ventilatory threshold calculation module in accordance with one embodiment of the present invention. The descriptor extraction module 1621, in one embodiment, extracts the descriptors needed from the input signal 1606 such as the breath signal energy 1607, the respiratory rate 1608 and the inhalation intensity 1609.

The VT and RCT usually coincide with the greatest changes in the respiratory rate. Accordingly, the decision module 1622 determines the maximum slope set 1617 over the descriptor set. Inhalation intensity is a useful descriptor because its values start going up when the subject expends the most effort in exercise. Hence, inhalation intensity is indicative of the RCT.

A comparison 1619 is then performed with objective value ranges before the final values of VT and RCT are extracted. The validation process comprises comparing the time stamps of the VT and RCT calculated by the framework 1605 with the VT (T1) and RCT (T2) as calculated using gas exchange measurements.

Figure 17:
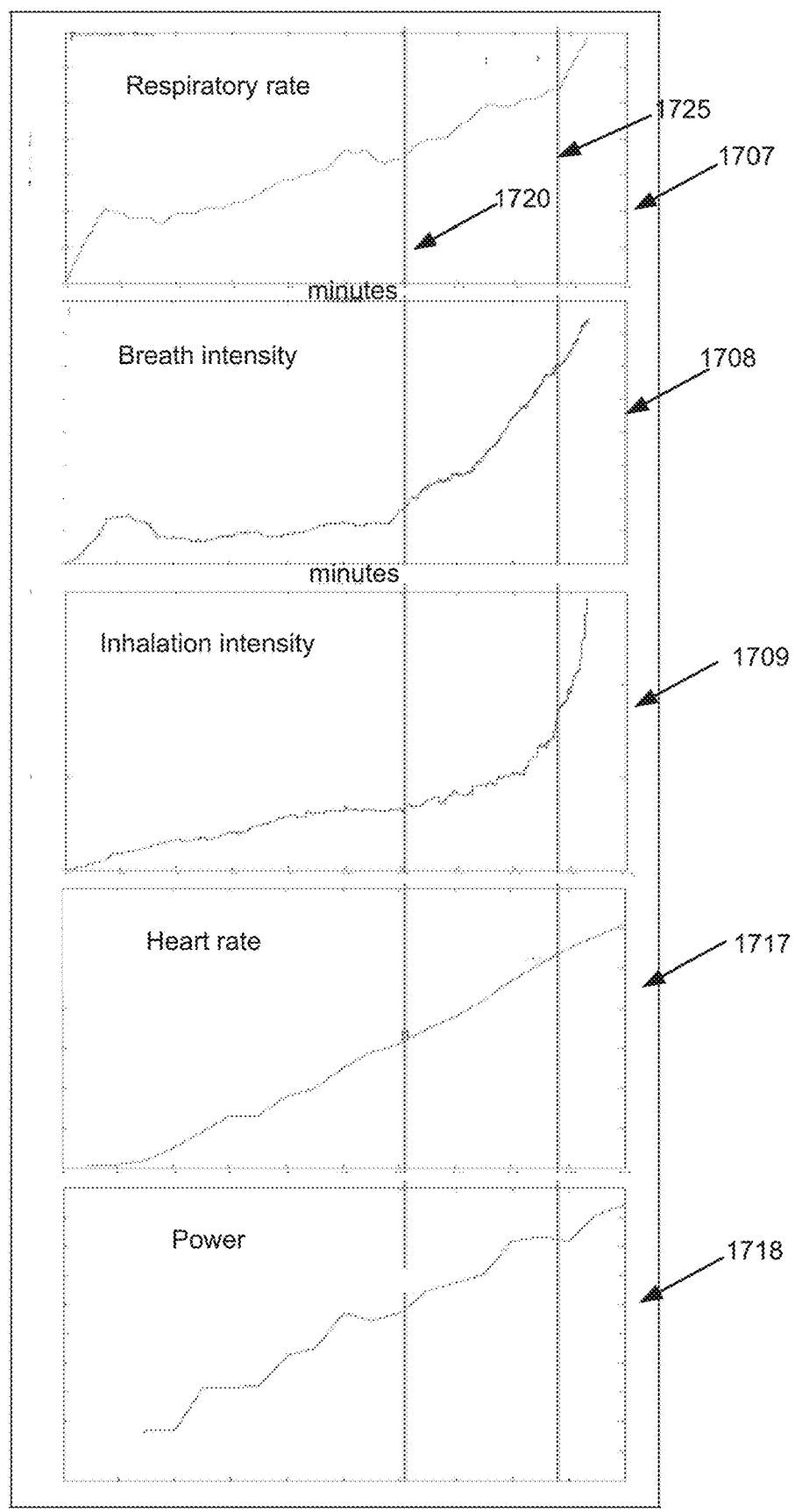
FIG. 17 depicts a graphical plot of respiratory rate, breath intensity, inhalation intensity, heart rate and effort versus time.

FIG. 17 depicts a graphical plot of respiratory rate, breath intensity, inhalation intensity, heart rate and effort versus time. The respiratory rate 1707, breath intensity 1708, inhalation intensity 1709, heart rate 1717 and power 1718 are all shown plotted against time. Time coordinates 1720 and 1725 correlate with VT and RCT because the derivative of the respiratory rate graph is highest at these coordinates and these coordinates also coincide with the greatest changes in the respiratory rate. Further, inhalation intensity as shown in graph 1709 starts to exponentially rise after coordinate 1725.

As mentioned above, embodiments of the present invention provide a framework for ventilatory threshold (VT) detection and respiratory compensation threshold (RCT) by performing digital signal processing of an audio signal of breath. Further, as described above, once the descriptors are extracted using the low level 700 of the DRCT framework, the VT and RCT points can be estimated. For example, FIG. 17 illustrates one method of estimating the threshold values using the extracted descriptors.

Additionally, as described above, the VT and RCT points are determined in the high layer 1500. The high layer is the post-processing layer (as shown in FIG. 15) after the audio has been analyzed and certain critical metrics related to the breath have been extracted. In other words, the low layer 700 extracts a set of vectors and arrays containing the results of the digital signal processing which it passes on to the high layer 1500. The low layer extracts and feeds the high-layer processes with at least three data vectors: a) breath intensity; b) breath rate; and c) heart rate. The manner in which the high layer 1500 processes the three data vectors will be discussed below in connections with FIGS. 22 and 23. These three data vectors will typically be processed, calibrated and utilized in a VT and RCT determination.

While the breath intensity and breath rate can be extracted from the respiratory audio signal, the heart rate may be extracted using an external heart rate sensor. It should also be noted that while the heart rate is not essential to the VT and RCT determination, the incorporation of the heart rate into the various algorithms and processes of the high-layer can enhance the overall accuracy of the system.

Conventional systems for determining VT and RCT require a skilled technician. For example, extracting meaningful ventilatory thresholds that occur during activity or exercise is typically done manually by a skilled exercise physiologist, pulmonologist or cardiologist. The conventional practice is to perform a cardiopulmonary test measuring respiratory gases, volumes and heart rate and filter and plot the values of VE/VO2 (VT) and VE/VCO2 (RCT) over time. Then by viewing the plots, the skilled technician manually selects specific minimum values of VE/VO2 and VE/VCO2.

VE/VO2 is the ratio of minute ventilation to oxygen uptake in the lungs and can also be referred to as an aerobic threshold or a fat burning threshold. VE/VCO2 is the ratio of minute ventilation to the rate of CO2 elimination and is also called the respiratory compensation threshold, lactate threshold, or an anaerobic threshold. Another approach to finding the most meaningful VE/VO2 threshold is to plot the respiratory exchange ratio (VO2/VCO2) and to find the crossing point at 50%. But this is only effective in steady state exercise of at least 5 minutes.

Embodiments of the present invention provide a way to automate the selection of ventilatory oxygen and carbon dioxide minimums, maximums, thresholds and slopes as a higher layer process that utilizes descriptors and metrics from the lower layer 700.

There are several challenges associated with the determination of the key thresholds like VT and RCT. For example, there are challenges associated with variations in a breathing session and false candidates. For example, a typical breathing session analyzed using the digital signal processing techniques of the present invention will contain several variations during the session. Embodiments of the present invention address problems related to variations during a breathing session by separating the sessions into categories according to their length and treating them accordingly. For example, the sessions may be categorized in multiple different categories spanning from short (approximately 15 minutes or less) to long sessions (over 20 minutes). In one embodiment, the categories may comprise a medium length session between approximately 15 to 20 minutes.

The shorter sessions can be analyzed by processing the data every minute while the longer sessions may need to be pre-processed with the data being merged into frames averaged over 2 minute increments. Accordingly, the shorter session can be used for zooming in and acquiring more details and accuracy while the longer sessions can be used to observe variation over a wider range of time. Analyzing the breathing session over longer duration allows observation of variations spanning longer periods of time without short-term fluctuations or spikes disrupting the analysis.

Further, conventional systems that are used to determine key thresholds such as VT and RCT also encounter problems related to false candidates. Issues associated with false candidates are why conventional systems require a skilled professional that has to make the determinations manually. False candidates typically occur because of pattern repetition. Further, when processing low-energy, noise-prone signals such as the breathing sounds, anomalies can be introduced to the data and distort the metrics creating or alternating existing patterns in a way that are misleading to the processes or algorithms determining the various thresholds, e.g., VT, RCT, etc.

This problem is further exacerbated by the fact that the metrics determined by embodiments of the present invention are connected to and depict changes in the actual functions of the body, which are constantly fluctuating and adapting to activity and exercise. In such cases false candidates can occur. In other words, the process is prone to errors in detection. This can happen as a result of inconsistent changes in breathing rate or intensity around key threshold points, but can also occur at arbitrary points during activity or exercise.

Embodiments of the present invention perform several procedures to address problems related to variations and false candidates. For example, embodiments of the present invention utilize, among other processes, a min-max determining process and a trimming process as will be discussed further below in connection with FIG. 23.

II.D.1 High-Layer Post Processing Overview

Figure 22:
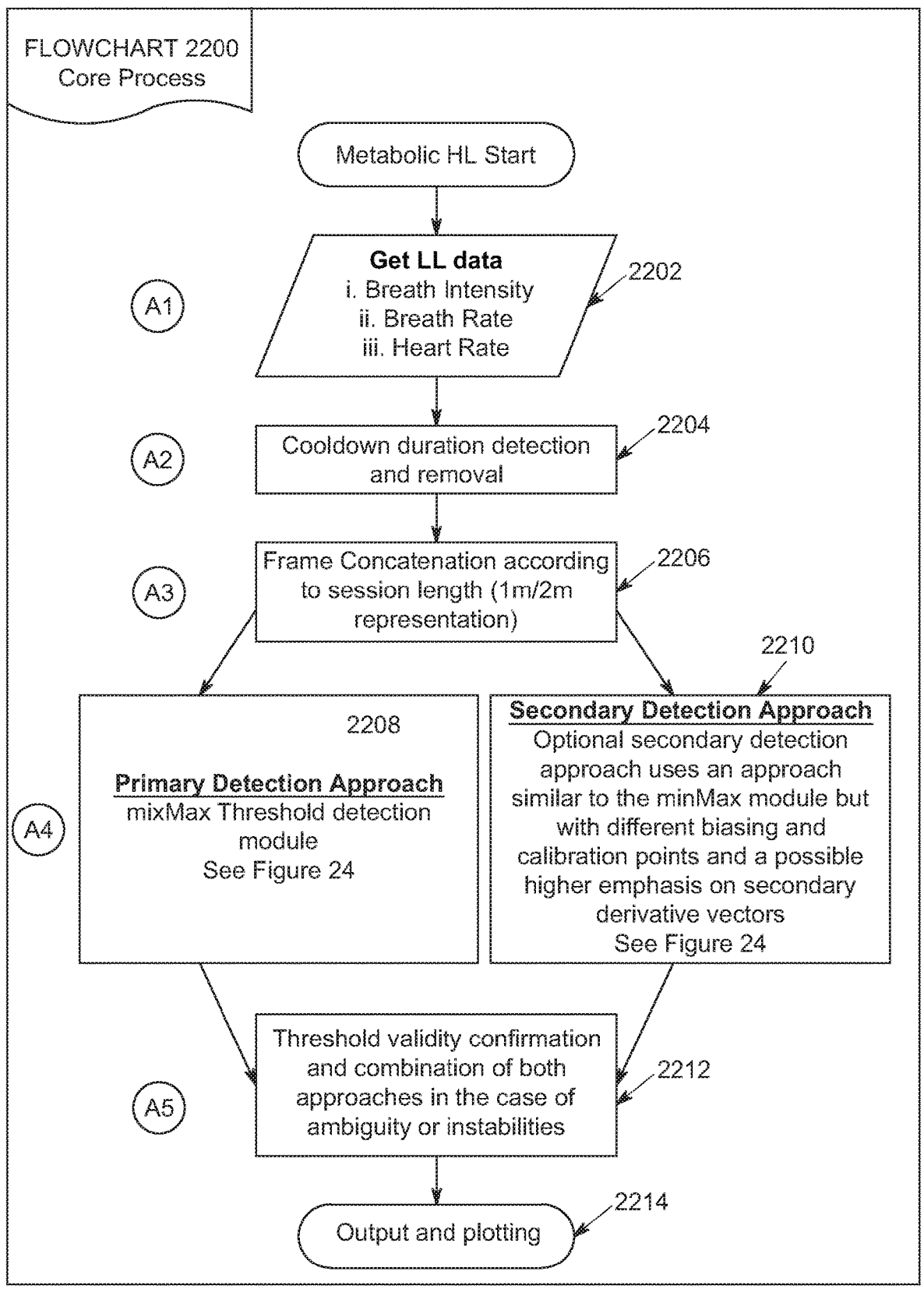
FIG. 22 illustrates a flowchart illustrating an exemplary structure of the high layer post-processing performed by the computer-implemented DRCT procedure in accordance with one embodiment of the present invention.

FIG. 22 illustrates a flowchart 2200 illustrating an exemplary structure of the high layer post-processing performed by the computer-implemented DRCT procedure in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 2200 should not be construed as limiting the scope of the invention. Rather, it will be apparent to persons skilled in the relevant art(s) from the teachings provided herein that other functional flows are within the scope and spirit of the present invention. Flowchart 2200 may be described with continued reference to exemplary embodiments described above, though the method is not limited to those embodiments.

At step 2202, the input module for the high layer post processing receives the input vectors with extracted audio information from the low layer 700. Typically, at least three vectors will be received from the low level, namely, the breath intensity, the breath rate and heart rate. Breath intensity is an acoustic measurement from the lower layer that correlates to the Ventilatory Equivalent (VE), which is the volume of respiratory gas exhaled in liters/min. As mentioned above, the heart rate will typically be extracted using a heart rate monitor and is not essential to the determination of the thresholds. The VT and RCT thresholds can be determined, for example, using purely audio analysis. The data received from the lower layer is organized in vectors that are essentially a collection of values, wherein each value corresponds to the duration of one analysis frame, for example, one point every 30 seconds. The three vectors (or two vectors if the optional heart rate vector is not available) form the basis of the threshold calculation.

At step 2204, a cool down period for the breathing session under analysis is determined and removed. The cool down section is typically not analyzed for threshold extraction and removing it reduces the set of possible candidates. Further, at step 2204, peak data points within the input vectors are examined with a cross-checking module to verify that no extreme audio anomalies exist within the data sets.

At step 2206, frame concatenation takes place, wherein the breathing session is compressed in accordance with a valid session duration. As indicated above, embodiments of the present invention address problems related to variations during a breathing session by separating the sessions into categories according to their length and treating them accordingly. In the case of shorter sessions, all the extracted information can be used to zoom in to all the areas of interest to more closely scrutinize the session. For longer sessions, however, the data is averaged over 2 minute increments allowing the characteristics of breathing session to be examined over a longer period of time. At step 2206, based on the session length, a window size is defined for the breath analysis. For example, a session under 15 minutes will have a window size of analysis of 1 minute. For longer sessions, the window size of analysis may be two minutes where the data is averaged every 1 or 2 minutes from the initial 30 second frames.

By way of example, a 20 minute session will have 2 vectors (one for breath intensity and one for respiratory rate) each of length 40 that may be received from the low layer 700 (one value for every 30 seconds) at step 2202. Since this is a longer session, the data may be averaged every 2 minutes so that defining the window size at step 2206 will result in vectors of length 10 (40/4). Each value in the final vector will correspond to 2 minutes of recorded data.

At step 2208, the primary threshold detection approach is employed. The primary detection approach comprises a min-max module that facilitates, for example, the detection of the thresholds VT and RCT. The functionality of the min-max module will be discussed in more detail in connection with FIG. 23. In one embodiment of the present invention, step 2208 performs the same functions as steps 1617 and 1619 in FIG. 16. In other words, the min-max module can determine the maximum slope set over the vectors received from the low layer (because VT and RCT usually coincide with the greatest changes in the respiratory rate and intensity, respectively) similar to step 1617. Further, the min-max module can perform a comparison with objective value ranges before the final values of VT and RCT are extracted (similar to step 1619).

Alternatively, at step 2210, in some embodiments, a secondary approach can also be employed to detect the thresholds. The secondary approach employs techniques similar to the min-max module, however, the biasing and calibration for the secondary approach is performed in a different manner and there is a higher emphasis placed on secondary derivatives. The secondary approach is optional, but can be used as an alternative fall back approach in the event that the min-max module fails to produce two valid thresholds. The secondary approach is typically more simplified than the min-max module and comprises different biasing on the weights of the metrics and a higher emphasis on the second derivative of the breath intensity and breath rate vectors. In other words, the secondary approach calibrates the vectors differently than the min-max module and can also be used as a complement to the min-max module to produce two valid threshold values.

At step 2212, subsequent to the threshold detection, a validation module is used to ensure the validity of the threshold values extracted (e.g., the VT and RCT). The validation module will take into account the thresholds, the session duration and other specific sub-metrics to ensure that the most likely and valid threshold candidates from the session are extracted. Further, in the event of ambiguity or instability, the validation module can extract thresholds from a combination of the primary detection approach 2208 and the secondary detection approach 2210.

At step 2214, the threshold values are outputted and plotted similar to the plots shown in FIG. 17.

As mentioned above, in order to determine the threshold values with the respiratory acoustic analysis system of the present invention, first the breath phases, the breath cycle, and all the descriptors that characterize breathing at rest, e.g., breath intensity, breath rate, heart rate, etc. need to be determined using the DRCT framework described above. Then the change in the relevant descriptors can be tracked as the patient begins to exercise and increases exercise intensity. Tracking the changes allows thresholds, e.g., VT and RCT to be determined because the ventilatory thresholds VE/VO2 (VT) and VE/VCO2 (RCT) exist over a time axis. Once one or more ventilatory thresholds using the acoustics has been identified, embodiments of the present invention can correlate the threshold or behavior of VE/VO2 and VEVCO2 with other sensors that are collecting data during activity and exercise, such as heart rate, blood oxygen levels, blood pressure, power output and speed.

II.D.2 the Min-Max Weighting Module and Threshold Detection

Figure 23:
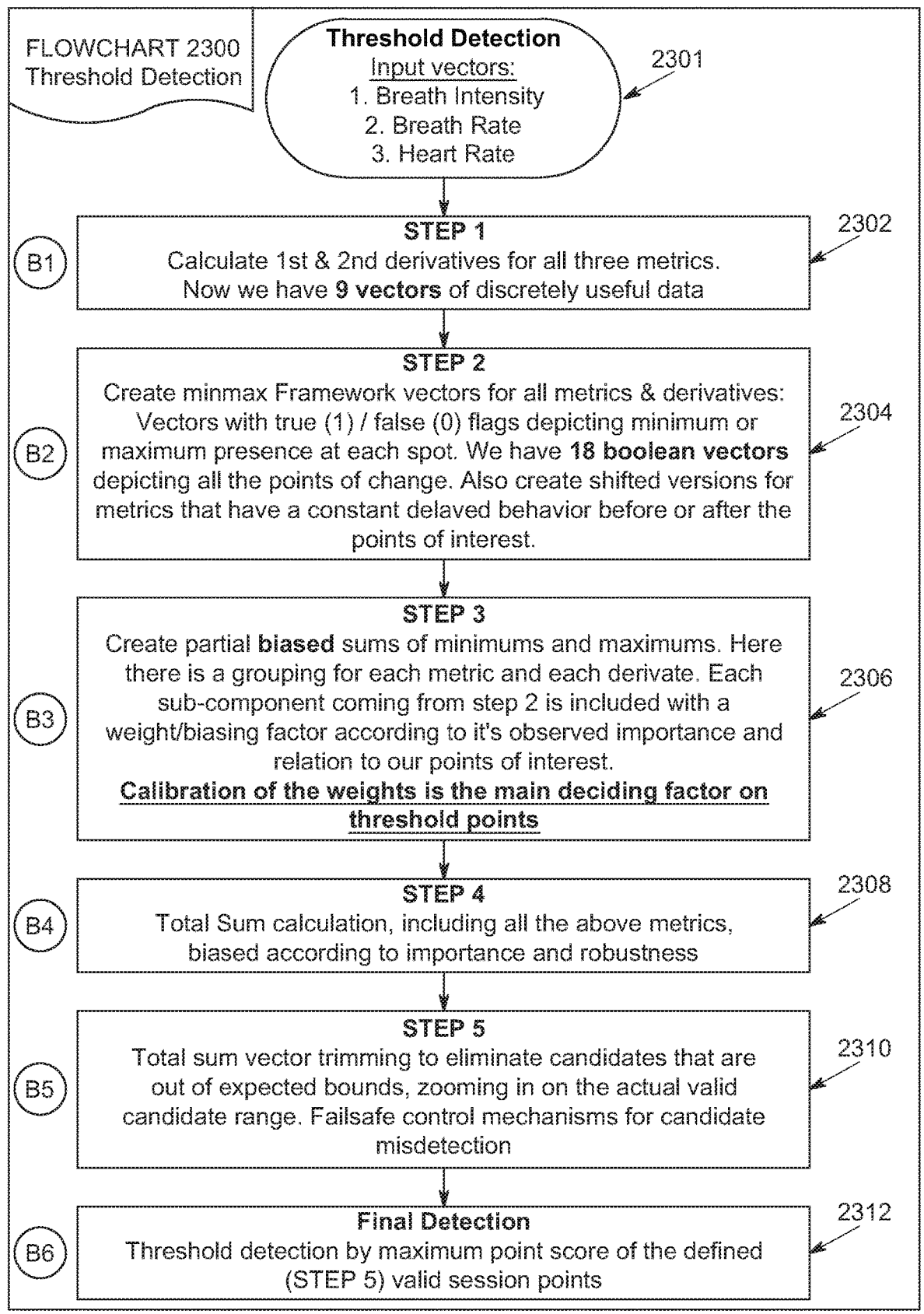
FIG. 23 illustrates a flowchart illustrating the manner in which threshold detection is performed in accordance with one embodiment of the present invention.

FIG. 23 illustrates a flowchart 2300 illustrating the manner in which threshold detection is performed in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 2300 should not be construed as limiting the scope of the invention. Rather, it will be apparent to persons skilled in the relevant art(s) from the teachings provided herein that other functional flows are within the scope and spirit of the present invention. Flowchart 2200 may be described with continued reference to exemplary embodiments described above, though the method is not limited to those embodiments.

At step 2301, the three vectors of interest (namely, breath intensity, breath rate and heart rate) are inputted to the threshold detection module. It should be noted that the heart rate metric is optional and not necessary for the threshold determination. Because the heart rate is not an acoustic metric, an extra sensor (e.g., a heart rate sensor) is required to collect the heart rate measurement. Accordingly, the heart rate measurement may not be available in all cases. As such, the heart rate is not relied upon by the threshold detection module. The threshold detection module can derive the thresholds from a purely audio analysis of the breath signal. However, if the heart rate is available, it is included in the calculations but is given a low importance bias by the min-max module. In other words, the heart rate is used mostly for high-level fine-tuning of the thresholds and cross-checking rather than as a critical metric that is necessary for threshold determination. Accordingly, the threshold detection module is capable of determining thresholds equally well without a heart rate measurement.

The threshold detection module comprises at least a min-max module (discussed, for example, in conjunction with steps 2304, 2306 and 2308) and a trimming module (discussed, for example, in conjunction with step 2310).

At step 2302, the threshold detection module uses the three vectors to derive further vectors that are also used to determine the thresholds of interest. Because the thresholds are determined by tracking changes in the relevant descriptors as the patient begins to exercise and increases exercise intensity, first and second derivatives can be calculated for each of the three extracted metrics and separate vectors can be created for each of the first and second derivatives.

For example, a first and a second derivative vector can be created from the breath intensity vector. Similarly, a first and a second derivative vector can be created from breath rate and heart rate vectors as well. Accordingly, in one embodiment, the three initial vectors can be used to derive six further vectors resulting in a total of nine vectors. In one embodiment where only the breath intensity and respiratory rate vectors are used as base metrics, then a total of six vectors are created. The first and second derivative determination is important because the rate of change of the various metrics, e.g., breath rate, intensity, heart rate, etc. also provide importation necessary to determine the thresholds. Both the first and second derivatives contain important and usable information that help to improve the accuracy and robustness of the calculations while helping address the aforementioned false candidate problem. In other words, the measured metric and each of the corresponding first and second derivative vectors provide information of different importance, quality and robustness.

At step 2304, the min-max framework vectors are created for all metrics and derivatives. The min-max module is at the core of the threshold detection process. This module advantageously tackles problems related to false candidates and repeating patterns that typically frustrate threshold determination. The min-max module examines the points of change of the base metric (e.g., intensity, respiratory rate, etc.) and their first and second derivatives. The methodology employed by the min-max module comprises measuring how rapidly the base metric and its derivatives change and examining where local minimum and maximum values occur.

In one embodiment, based on the pre-calculated 9 (or 6 depending on if heart rate is being used or not) vectors, 18 (or 12) Boolean vectors are created that indicate the presence (true) or absence (false) of minimums and maximums along all the time points of the session. These Boolean vectors contain information regarding the points of change for the base metrics (and their corresponding derivatives) and form the basis of the grading system employed by the min-max module. For each pre-calculated vector, 2 Boolean vectors are created. For example, for the breath intensity metric, 2 Boolean vectors are created corresponding to the breath intensity vector. One of the Boolean vectors comprises '1's in all spots where a minimum is detected in the breath intensity vector and '0's in all the others. The other Boolean vector comprises '1's in all the spots where a maximum is detected in the breath intensity vector and '0's in all the others. Similarly, 2 Boolean vectors are created corresponding to each of the base metrics and their first and second derivative vectors.

Further, in one embodiment, a set of time-shifted Boolean vectors corresponding to the base metric vector (one or two points before and after each point of examination) and corresponding to the first and second derivative vectors are created. In other words, time-shifted vectors corresponding to each of the base metric and its derivative values are created. Time-shifted vectors are used because the human body's response to exercise is not always constant and will show a change in breath rate and intensity a few seconds before or after a ventilatory threshold occurs.

For example, time-shifted versions of each of the base metric and its two derivative vectors can be created, wherein the time-shifted vectors contain values that are time-shifted by a single time point. In other embodiments, any number of time-shifted vectors may be created from the base metric vector and its corresponding derivatives. The time-shifted vectors are important to threshold detection because the physique of the human body and the changes it undergoes when exercising appear following a short delay, which the min-max module takes into account using the time-shifted vectors to enhance the accuracy of the results. For example, the breath rate can go up one frame after the actual threshold or the heart rate may also delay in its rise around the threshold points of interest. In this way the mix-max calculation process closely tracks the actual way in which a body functions and adjusts to changing stress levels.

At step 2306, a point system is created weighting the importance (and thus the amount of contribution) of each Boolean vector. In one embodiment, various sub-groups of all the Boolean vectors are combined into sum vectors. For example, there may be sum vectors created that comprise the minimums alone or there may sum vectors comprising the maximums. Alternatively, there may be sum vectors comprising a combination of the minimum and maximum vectors. By way of further example, a group of sub total vectors may be calculated from the Boolean vectors, e.g., a vector with all the derivative minimums, a vector with all the derivative maximums, a vector with all the second derivative minimums, and a vector with all the second derivative maximums. Determining these sub-group of Boolean vectors allows more control of the system and facilitates observation of the contribution of each metric vector (or sum of metric vectors) to the detection. As a result, the appropriate biasing and weighting of all the various vectors can be efficiently performed before adding them into a total master vector (as will be described below).

During the intermediate sum-vector creation, every value in each sum vector is biased with an "importance" coefficient. The coefficients relate to the importance of each specific value in a sum vector and also to the robustness of the behavior of the corresponding metric. For example, a sum vector may contain a value that when present directly points to a threshold but is also very prone to noise or is unstable. In such a case, this particular value may be biased lower even though it provides a clear indication of a threshold presence because it may induce instabilities to the overall system in certain cases. The calibration of the biasing weights for each of the values in a sum vector is a critical component of the threshold detection process and one of the reasons of the importance of the min-max module.

At step 2308, after the biasing is complete, the min-max module creates a total sum vector (or master vector) incorporating all the base metric and other derived vectors in specific ways. In other words, all the weighted Boolean vectors are summed, thereby, creating the final sum vector. This vector (which has the same length as the base metric vectors) has a total score for each time point it contains with the highest scores indicating the most probable threshold candidates. In one embodiment, the master sum vector is similar to a threshold-probability map of the session. The higher the value at a specific point, the more likely that there is a threshold at that point.

The min-max module considers every time point contained in the total sum vector as a possible candidate. The total sum vector incorporates a biased and combined behavior of all the metrics at every given point. This results in an "importance" graph that indicates the importance of the specific points according to a pre-defined criteria. The biasing/weighting process is typically a critical part of the threshold detection process. It typically includes a multi-layered combination of several vectors, e.g., base metric vectors, first derivative vectors, second derivative vectors, additional shifted vectors for metrics that show dramatic changes in the curve before or after the desired points.

At step 2310, the total sum vector is trimmed to eliminate candidates that are out of expected bounds. In one embodiment, a trimming module is coupled to the min-max module that allows zooming in on the actual valid candidate range. After observing the behavior of the breath intensity and rate, the redundant data can be eliminated, which allows zooming in on the data that is meaningful. Zooming in on the meaningful information while leaving out the redundant information also helps eliminate false candidates.

The trimming can comprise using a priori knowledge and expectations of a typical breathing session. For example, a typical breathing session will likely have similar repeating patterns across the session. The intensity will vary, but, for example, in a session that is 18 minutes long with a known power wattage increase per step, it is presumed that the VT cannot occur as early as minute 5. This control information can then be used to the trim the usable and valid range out of the 18 minute session and discard the rest. Accordingly, trimming enables the threshold detection process to trim out the parts of the session where it is highly unlikely that a threshold exists and permits zooming into the parts where it likely that a threshold does exist. Further, trimming enables false candidates with similar behavior to be eliminated. Trimming also directs focus to the most likely threshold candidates.

At step 2312, after the master total sum vector is trimmed, the candidate selection is processed from a maximum peak selection of the processed master vector. If the sum vectors are well-calibrated at step 2306, the thresholds can be efficiently and rapidly detected from the master vector.

The master vector has a total score for each time point it contains with the highest scores indicating the most probable candidates. In some cases only a single threshold, e.g., VT may be determined while in other cases two thresholds, e.g., VT and RCT may be detected. For example, in certain instances only a single threshold is detected where the highest scoring point (or candidate) in the master vector is selected. This may, for example, be the ventilatory threshold (also known as the aerobic threshold). In this case, a single threshold may occur when the subject ends the exercise while at middle or hard effort or intensity.

In other instances, two thresholds may be detected. A two threshold detection usually occurs when the subject ends the exercise closer to a maximum effort or intensity. The candidates are sorted by score, but the threshold detection process also takes into account some observations based on time differences and also taking into consideration possible anomalies. For example, the two candidates (for thresholds) may be selected by sweeping of the master vector from right to left (from the end of the session to the beginning of the session). This approach is used because the second threshold (the RCT or anaerobic threshold) is typically more prominent with stronger and higher values. The VT (also known as the aerobic threshold) can have more subtle values. Once the RCT candidate is identified clearly, the VT candidates can be examined by setting the RCT candidate point as the right most reference point and sweeping for possible VT candidates prior to the RCT point.

Further, step 2312 also comprises performing fail-safe checking and other error-checking to handle the more extreme and erroneous cases, e.g., cases of heavy noise presence, invalid session, and other audio problems. Also, ruling out unlikely or invalid candidates is performed at step 2312 by eliminating time points where it is unlikely to have a threshold. This works as a final filter in the event multiple points scored high in the min-max scoring system.

The meaningful thresholds and behavior of VE/VO2 (VT) and VE/CO2 (RCT) extracted using embodiments of the present invention during activity and exercise is a standard for exercise prescription and diagnostics for athletes, patients recovering from illness and surgery and patients with chronic heart, lung or metabolic disease. However, the current practice to test and determine meaningful thresholds and behavior of VE/VO2 and VE/VCO2 during exercise and activity is very costly, cumbersome and requires professional and technical staff, making this information inaccessible to most people. In addition, it is difficult to do the test more than once a year and so valuable data regarding changes in one's physiology, health and fitness is not available.

Embodiments of the present invention use a microphone during activity or exercise to record breathing and extract primary descriptors (from a low layer) such as breath intensity and breath rate. Embodiments of the present invention then further extract meaningful ventilatory thresholds and behavior (slopes) for health, fitness and performance and provide important physiological data at a low cost and without professional and technical staff. Embodiments of the present invention also advantageously provide fresh data easily and efficiently, where a technician can record meaningful ventilatory thresholds and behavior during exercise or activity more frequently (monthly, weekly, daily) and be able to track the changes in ventilatory behavior and thresholds over time. The data extracted by embodiments of the present invention will not only be useful for individuals but will also add to the field of exercise physiology and cardio-pulmonary medicine.

In addition to identifying ventilatory thresholds and behavior during activity and exercise, embodiments of the present invention also allow the previously discussed lower layer descriptors such as breath sounds like wheeze, crackles and cough to be analyzed in conjunction with and in relation to meaningful ventilatory behavior and thresholds. This allows users, trainers and health practitioners secure more meaningful information about lung and heart health and facilitates early detection for disease.

Figure 24:
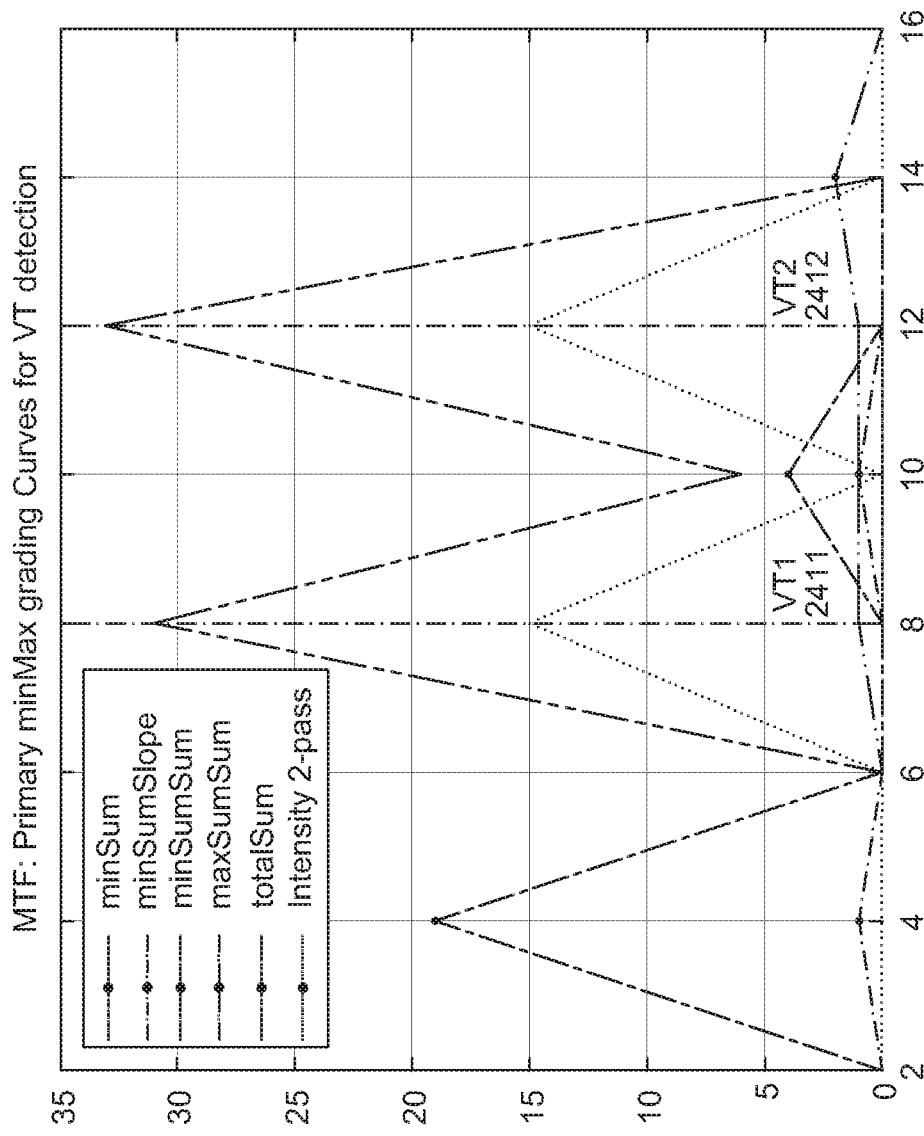
FIG. 24 illustrates an exemplary case in which VT and RCT can be detected graphically in accordance with an embodiment of the present invention.

FIG. 24 illustrates an exemplary case in which VT and RCT can be detected graphically in accordance with an embodiment of the present invention. As discussed above, once the group of sub total vectors is determined and the master vector is extracted (subsequent to biasing/calibrating), the vectors can be plotted. In the scenario shown in FIG. 24, two thresholds can be detected.

As explained above, a two threshold detection usually occurs when the subject ends the exercise closer to a maximum effort or intensity. For example, the two candidates (for thresholds) may be selected by sweeping of the master vector from right to left (from the end of the session to the beginning of the session). This approach is used because the second threshold (the RCT or anaerobic threshold) is typically more prominent with stronger and higher values. The VT (also known as the aerobic threshold) can have more subtle values. Once the RCT candidate is identified clearly, the VT candidates can be examined by setting the RCT candidate point as the right most reference point and sweeping for possible VT candidates prior to the RCT point. In FIG. 24, for example, once RCT 2412 is determined, the VT 2411 candidate can be determined by setting the RCT candidate as the right most reference point and sweeping for possible VT candidates prior to the RCT point.

II.E. Miscellaneous Parameters

Figure 18:
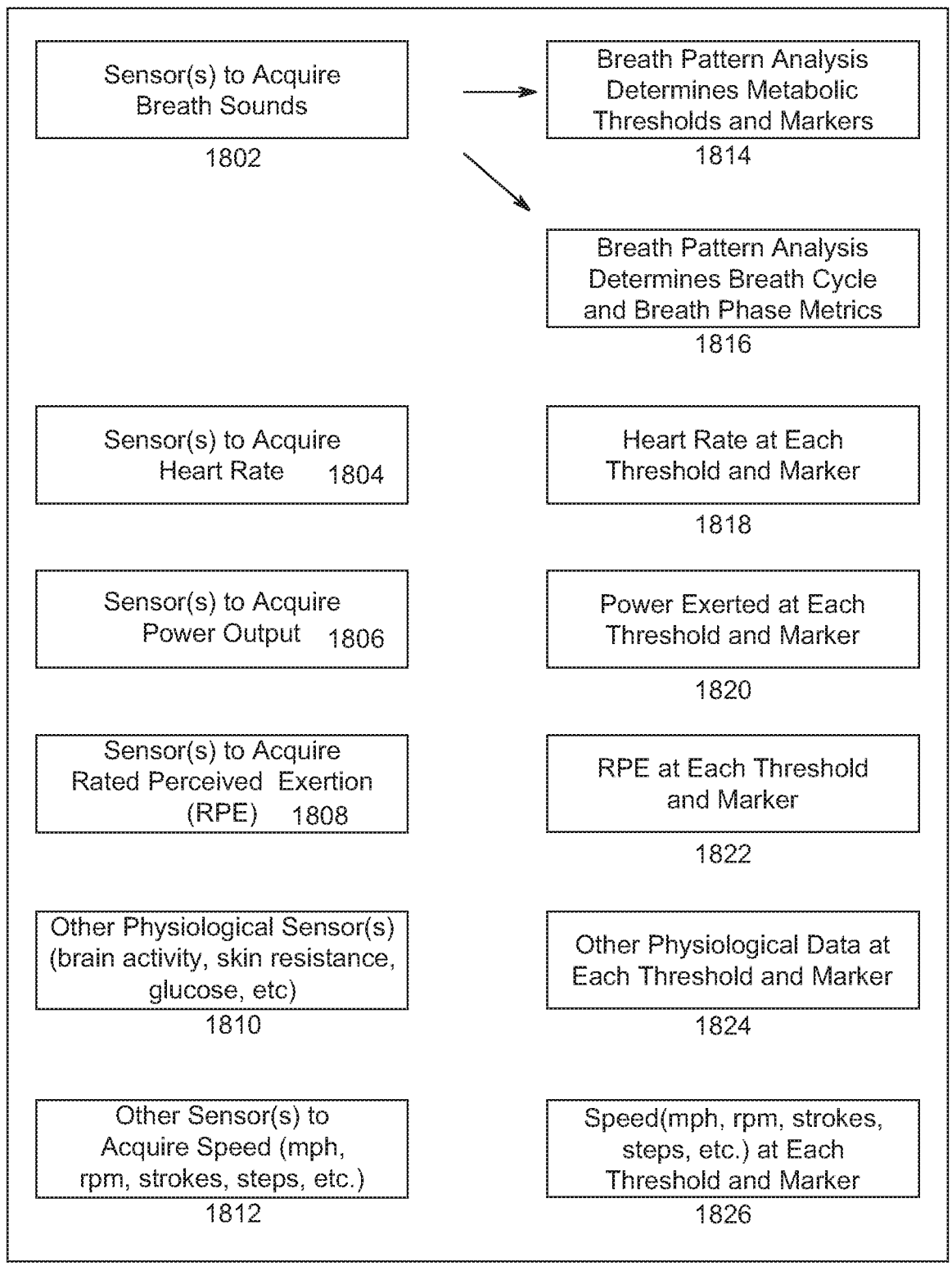
FIG. 18 illustrates additional sensors that can be connected to a subject to extract further parameters.

FIG. 18 illustrates additional sensors that can be connected to a subject to extract further parameters using the DRCT framework. Additional sensors for heart rate, power output, speed (mph, strokes, steps, etc.), brainwave activity, skin resistance, glucose, etc. are correlated to the ventilatory thresholds that are detected by the classifier core 730 to deliver a full report where several data points can be available.

Sensors to acquire breath sounds 1802 can be connected to a subject to perform breath pattern analysis and determine metabolic thresholds and markers 1814 and breath cycle and breath phase metrics 1816, as discussed above.

Further, sensors to acquire heart rate 1804 can be connected to determine heart rate at each threshold and marker 1818.

Sensors to acquire power output 1806 can be connected to the subject to extract information regarding power exerted at each threshold and marker 1820.

Sensors to acquire related perceived exertion (RPE) 1808 can be connected to derive RPE at each threshold and marker 1822.

Other physiological sensors e.g. brain activity, skin resistance, glucose, etc. can be connected to derive other physiological data at each threshold and marker 1824.

Finally, other sensors to acquire speed (mph, rpm, strokes, steps, etc.) can be used to derive speed (mph, rpm, strokes, steps, etc.) at each threshold and marker 1826.

In addition, input data regarding the user, client or patient including but not limited to gender, age, height, weight, fitness, level, nutrition, substance use (e.g. drugs, alcohol, smoking etc.), location, health info, lifestyle info, etc. can be used to determine a variety of metrics including ventilatory thresholds. The output data metrics can include, but are not limited to heart rate, power output, rated perceived exertion (RPE), speed of activity, cadence, breath cadence, calories, brain wave patterns, heart rate variability, heart training zones, respiratory training zones, resting metabolic rates, resting heart rate, resting respiratory rate, etc.

Cadence refers to the rhythm, speed, and/or rate of an activity and is frequently referred to in cycling and other sports. Breath cadence is the rhythm of breathing and can be compared to other rhythms including, but not limited to, rpm, strokes, steps, heart beat, etc.

Respiratory training zones can be calculated from the respiratory rates and other respiratory markets at the metabolic thresholds. Respiratory training zones of varying intensity could then be calculated.

The ventilatory response of a subject can be improved by optimizing the rate, depth, tension, flow, ramp, and breath phase relationships at different exercise intensities. Accordingly, the subject can produce more power, sustain exercise intensities longer (increase endurance), prolong or improve fat burning metabolism. Many techniques can be used to optimize ventilatory response including auditory, visual, kinesthetic real time and end time feedback, cueing, and coaching. Further, the ventilatory response can be optimized at different times, including, during different exercise intensities to get the most power, endurance, and speed, during recovery to get the best recovery (resting metabolic rate, resting heart rate, resting respiratory rate, and characteristics), and during any physical or mental activity to counter the negative effects of stress.

The delivery technology to allow a user to interact with the DRCT system and receive results can comprise wired sensors, wireless sensors, in-device analysis and display, cloud software in electronic portable device (e.g. mobile device, cell phone, tablet etc.), stand alone software, SaaS, embedded software into other tracking software, or embedded software on exercise, medical or health equipment.

II.F. User Interface

Figure 19:
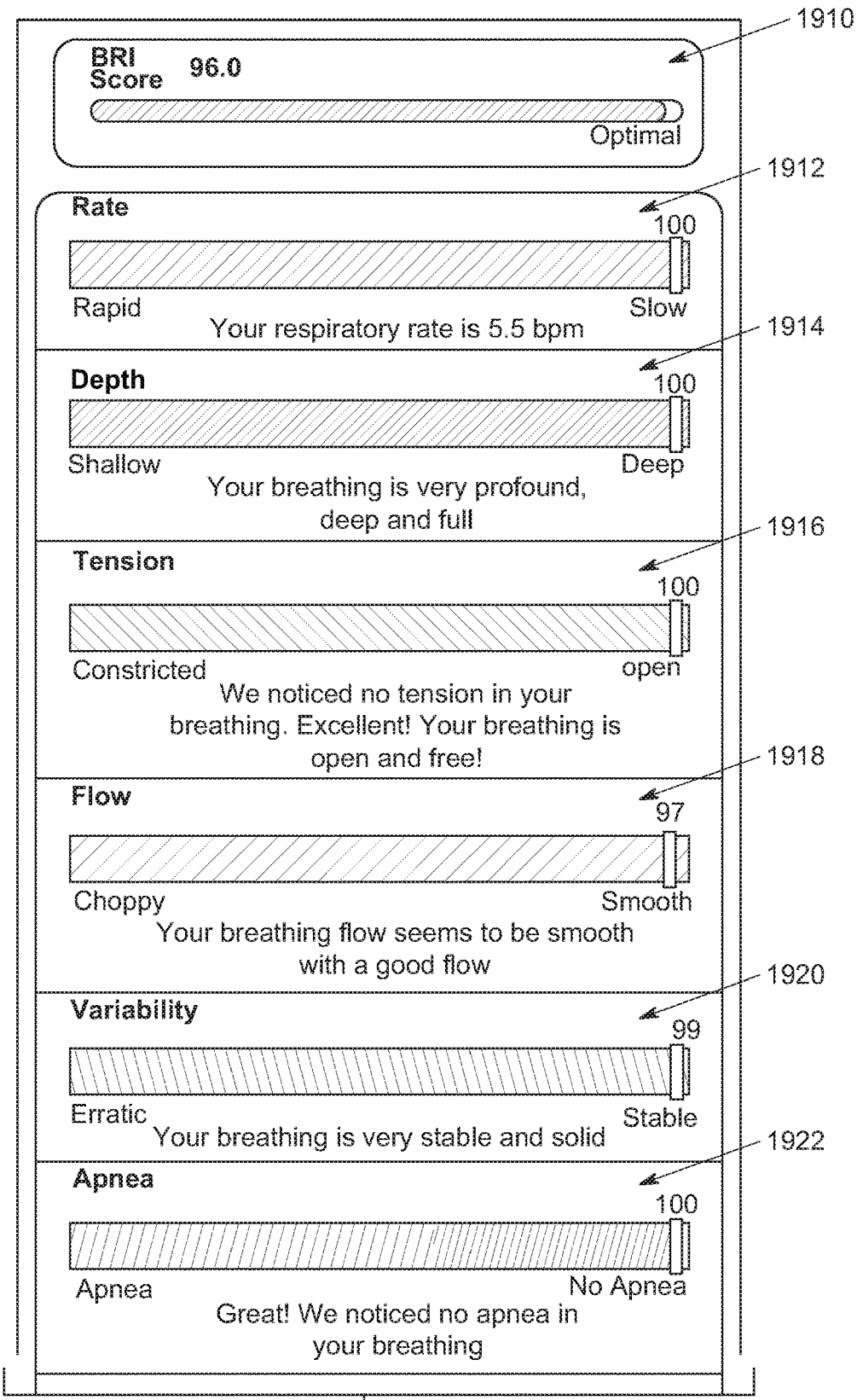
FIG. 19 shows a graphical user interface in an application supporting the DRCT framework for reporting the various metrics collected from the respiratory acoustic analysis in accordance with one embodiment of the present invention.
Figure 19A:
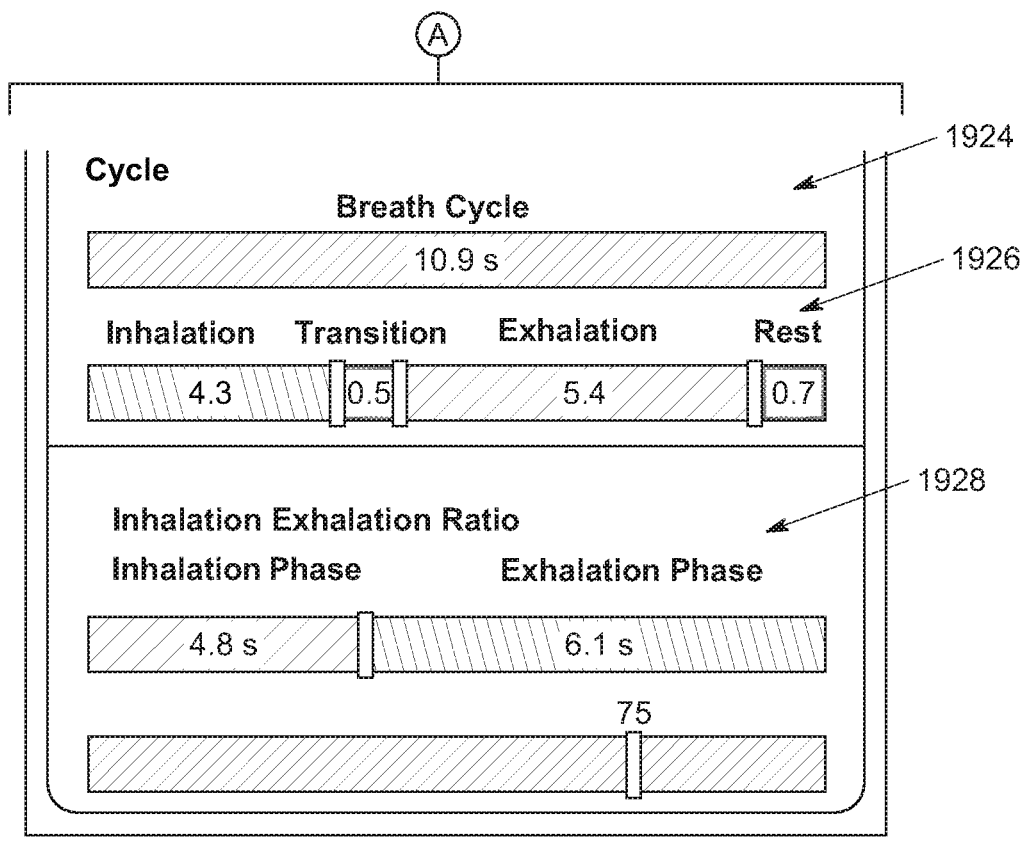

FIG. 19 shows a graphical user interface in an application supporting the high layer 1500 of the DRCT framework for reporting the various metrics collected from the respiratory acoustic analysis in accordance with one embodiment of the present invention.

The application for implementing the DRCT framework and performing the respiratory acoustic analysis of the present invention is operable to provide a user an interface for reporting the various statistics, metrics and parameters collected from the various analyses conducted using a subject's breath. This application can either be installed on a portable electronic device e.g. smart phone, tablet etc. connected to the microphone being used to capture the breathing sounds. Alternatively, it can be installed on a computing device such as a PC, notebook etc. that is either connected directly to the microphone or to a portable electronic device that is capturing the breathing sounds from the microphone.

The reporting interface of the application can assign a score 1910 to the subject's quality of breathing. It can also report other metrics and statistics, e.g., respiratory rate 1912, depth of breathing 1914, tension 1916, flow 1918, variability 1920, apnea 1922, breath cycle duration 1924, breath phase durations 1926, and inhalation/exhalation ratio (IER) 1928.

Figure 20:
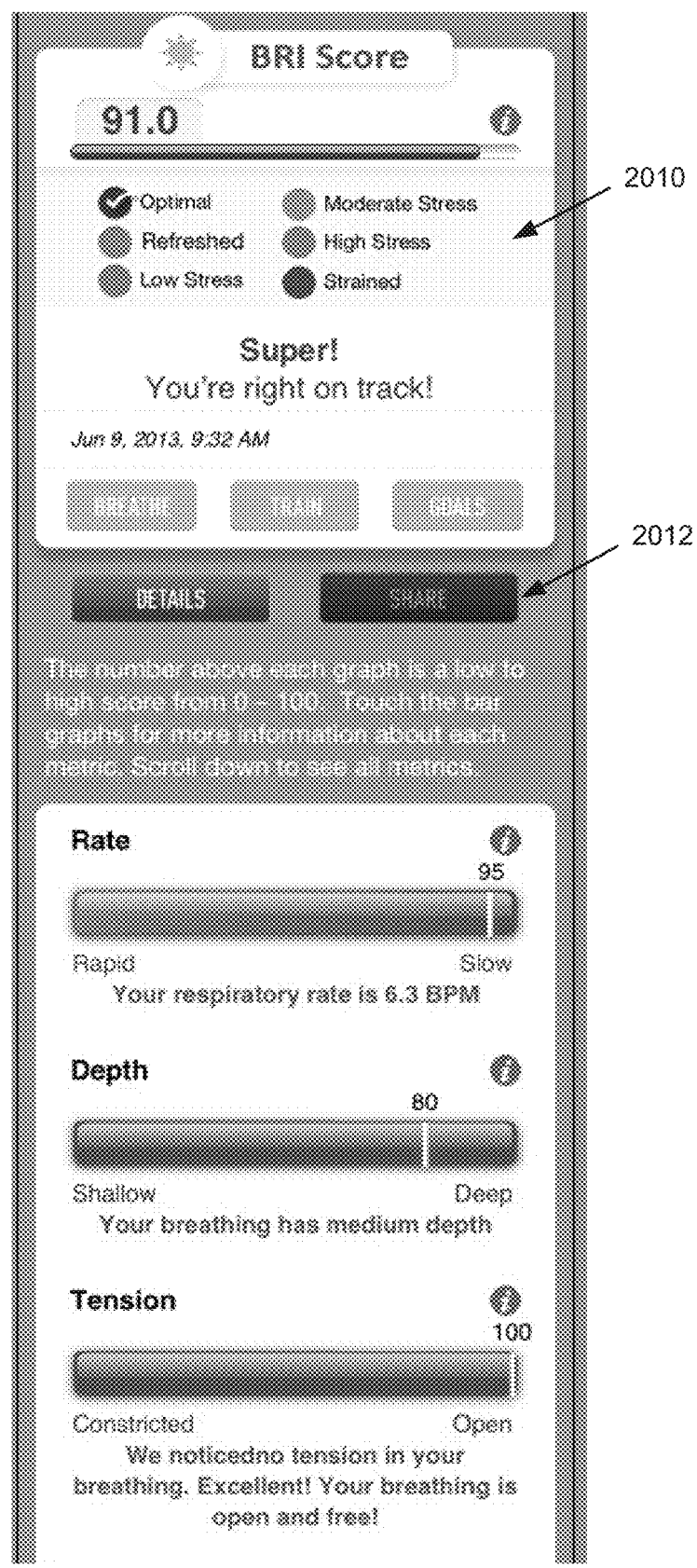
FIG. 20 illustrates a graphical user interface in an application supporting the DRCT framework for sharing the various metrics collected from the respiratory acoustic analysis in accordance with one embodiment of the present invention.

FIG. 20 illustrates a graphical user interface in an application supporting the DRCT framework for sharing the various metrics collected from the respiratory acoustic analysis in accordance with one embodiment of the present invention. In one embodiment, after the various metrics are reported, as illustrated in FIG. 19, they can be shared by the user by clicking an icon 2012 in the graphical user interface. The user, therefore, can share metrics related to the subject's breathing in addition to the score and performance level 2010 with other individuals through the user interface.

Figure 21:
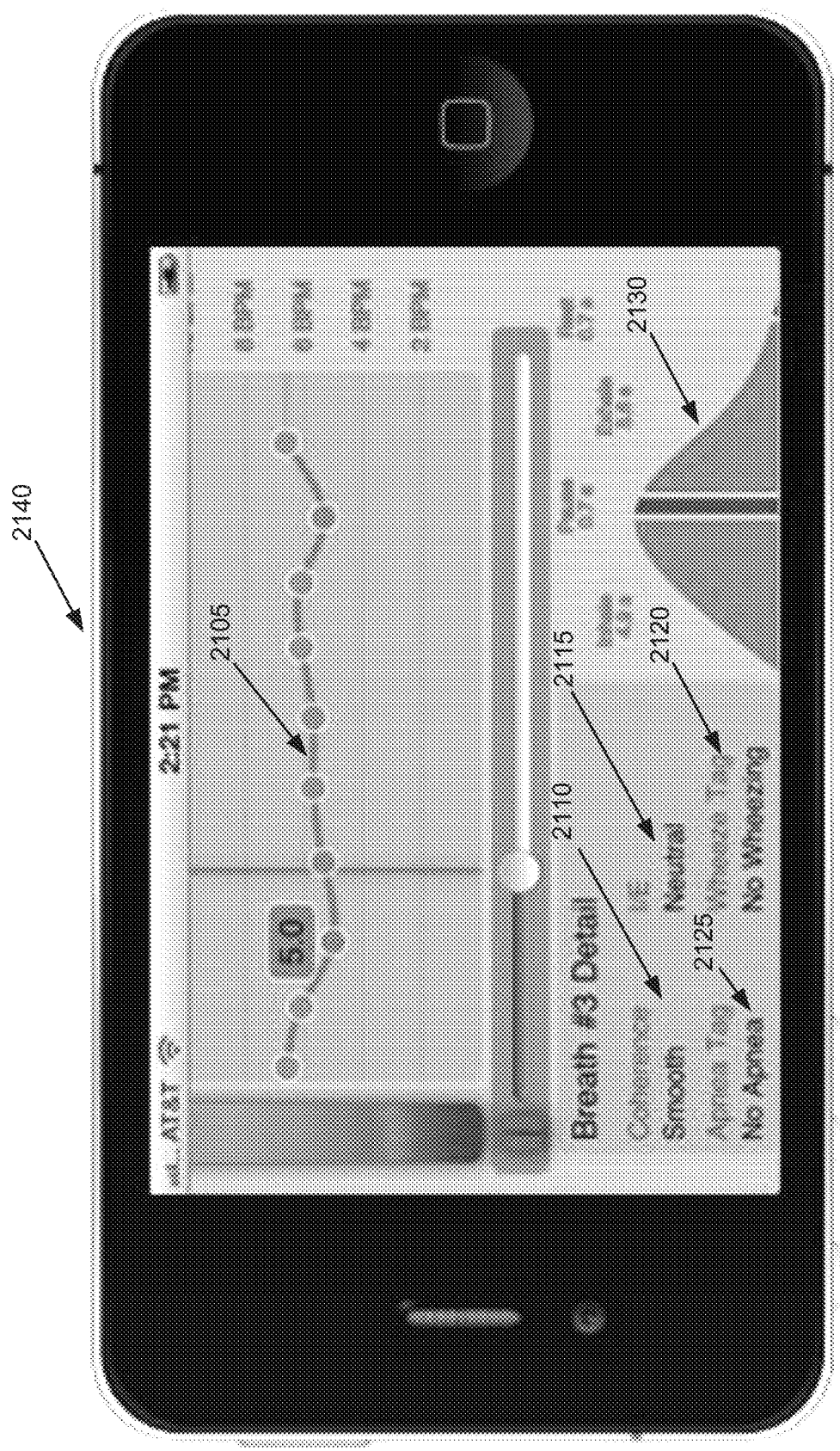
FIG. 21 illustrates an electronic apparatus running software to determine various breath related parameters in accordance with one embodiment of the present invention.

FIG. 21 illustrates an electronic apparatus running software to determine various breath related parameters in accordance with one embodiment of the present invention. The application for reporting the various metrics, as discussed above, can, in one embodiment, be installed on a portable electronic device such as a smart phone 2140. In addition to having the ability to report the various metrics and statistics discussed in connection with FIG. 19, the application can also illustrate the various metrics and statistics in graphical form, e.g., the breaths per minute (BPM) metric 2105 can be reported as a function of time as shown in FIG. 21. Further, information regarding other metrics such as coherence 2110, apnea 2125, wheezing 2120, IER 2115 can also be shown by the application. In one embodiment, a curve 2130 illustrating the durations of the various phases in a breath cycle can also be shown by the application.

III. Dynamic Respiratory Classification and Tracking of Wheeze and Crackles

Wheezing is a continuous harmonic sound made while breathing and may occur while breathing out (exhalation or cough) or breathing in (inhalation). Wheeze or wheezing sounds occur during breathing when there is obstruction, constriction or restriction in the lung airways and is often indicative of lung disease or heart disease that affects the lungs. Wheeze can be categorized as a whistling sound, a stridor (a high pitched harsh wheeze sound) or rhonchi, (a low pitched wheeze sound). Asthma and chronic obstructive pulmonary disease (COPD) are the most common cause of wheeze. Other causes of wheeze can include allergy, pneumonia, cystic fibrosis, lung cancer, congestive heart failure and anaphylaxis.

The occurrence of wheeze is a diagnostic marker for lung disease and is most commonly detected by listening to the lungs with a stethoscope. Some wheeze sounds may also be heard by the person generating the wheeze or a person nearby, and thus the occurrence of wheeze can also be a patient-reported symptom.

Most people suffering from wheeze-related symptoms have many different types of wheezes, each coming from a narrowed area in the lungs that produces frequencies simultaneously or in a sequence. The frequencies, intensities, behavior and characteristics of wheeze sounds reflect the degree of airway narrowing and the condition of the resonating airway tissue. But, unfortunately, most of it remains hidden or inaudible to the human ear. Digital devices exist that can report the occurrence of wheeze sounds, but these devices will often miss wheeze particles and other characteristics, which may be hidden or inaudible, and yet reflective of lung disease.

Crackles are discontinuous, explosive, unmelodious sounds that are caused by fluid in the airways or the popping open of collapsed airway tissue. They can occur on inhalation or exhalation. Crackles also known as rales, are often categorized as fine (soft and high pitched), medium or coarse (louder and lower in pitch), and can be caused by stiffness, infection, or collapse of the lung airways. They can also be referred to as rattling sounds. Diseases where crackles are common are pulmonary fibrosis and acute bronchitis.

Crackles are most commonly heard with a stethoscope, however the number of popping sounds (including their velocity, duration, pitch and intensity) is difficult to hear with the human ear.

Embodiments of the present invention provide an apparatus for evaluating lung pathology that may comprise a microphone or a device with a microphone such as mobile phone that includes a headset and a speaker. The apparatus may comprise one or more of the following devices for lung testing, monitoring and therapy: a mobile phone, a headset, a speaker, a Continuous Positive Airway Pressure (CPAP), a spirometer, a stethoscope, a ventilator, cardiopulmonary equipment, an inhaler, an oxygen delivery device and a biometric patch.

The apparatus may be similar to the apparatus illustrated in FIG. 4, which shows an exemplary breathing microphone set-up used in the methods and apparatus of the present invention. As discussed in connection with FIG. 4, a conventional microphone 420, available commercially, can be used to record the breathing patterns of the user. By using the microphone 420 that comes with many electronic devices (such as an iPad® or iPhone®) and the software as described here within (e.g. in connection with FIGS. 5, 19, 20, and 21), the present invention can detect wheeze and crackle related events. Moreover, the test can be self-administered without requiring special testing equipment or trained personnel.

In one embodiment, the apparatus captures respiratory sounds, and sends the respiratory recording to a computing device, which performs dynamic respiratory classification and tracking. The computing device stores the recording and the data in a computerized medium. Embodiments of the present invention provide a significant improvement over conventional methods of detecting wheeze and crackle, because as noted above, while digital devices exist that can report the occurrence of wheeze sounds, this approach will often miss wheeze particles and characteristics that are hidden or inaudible and yet reflective of lung disease. Accordingly, embodiments of the present invention allow wheeze sounds to be detected with a high level of sensitivity. Embodiments of the present invention also do not miss wheeze particles and are sensitive enough to recognize wheeze characteristics that are hidden and inaudible to traditional methods of wheeze detection.

Similarly embodiments of the present invention allow crackles to be detected—prior methods of detecting crackle involved the use of non-computerized methods, e.g., using a stethoscope. Embodiments of the present invention comprise a significant improvement to computer related technology by providing hardware and software that is able to detect wheeze sounds and crackles with a high degree of sensitivity.

Figure 25A:
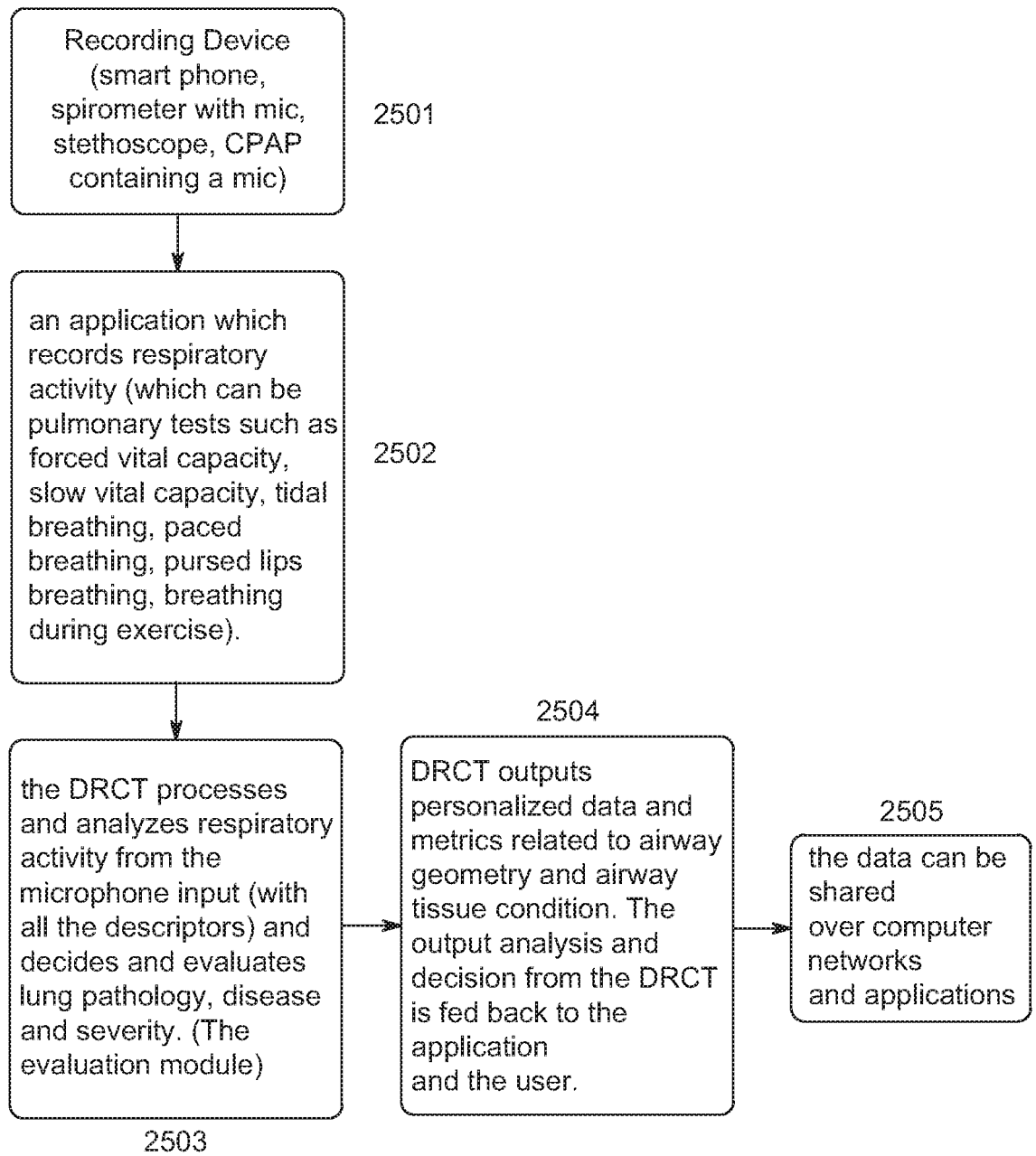
FIG. 25A illustrates an exemplary flow diagram indicating the manner in which the DRCT framework can be used in evaluating lung pathology in accordance with an embodiment of the present invention.

FIG. 25A illustrates an exemplary flow diagram indicating the manner in which the DRCT framework can be used in evaluating lung pathology in accordance with an embodiment of the present invention.

At block 2501, a recording device is used (e.g. microphone 420) is used to record breathing sounds. The recording device can, for example, be a smart phone, a spirometer with a microphone (as will be discussed further below), a stethoscope, or a CPAP machine with a microphone.

At block 2502, an application associated with the recording device (e.g. the software shown in FIG. 5) record the respiratory activity. The respiratory activity can be pulmonary testing and monitoring of forced vital capacity, slow vital capacity, tidal breathing, paced breathing, pursed lips breathing, and breathing during exercise.

At block 2503, the DRCT framework discussed above processes and analyzes respiratory activity from the microphone input. As discussed above, first the breath phases, the breath cycle, and all the descriptors that characterize breathing at rest need to be determined using the DRCT framework. Then the change in the relevant descriptors can be tracked as the patient begins to exercise and increases exercise intensity. The descriptors and the manner in which they change during activity can be used to decide and evaluate lung pathology, disease and severity. Details regarding the manner in which this is done using neural networks will be discussed further in connection with the Training and Evaluation Modules of FIGS. 34 and 35.

At block 2504, the DRCT framework outputs personalized data and metrics related to airway geometry and airway tissue condition. The output analysis and decision from the DRCT is fed back to the software application and the user (e.g., software running on the phone as shown in FIG. 5).

At block 2505, the data can be shared over computer network and with other applications as well.

Figure 25B:
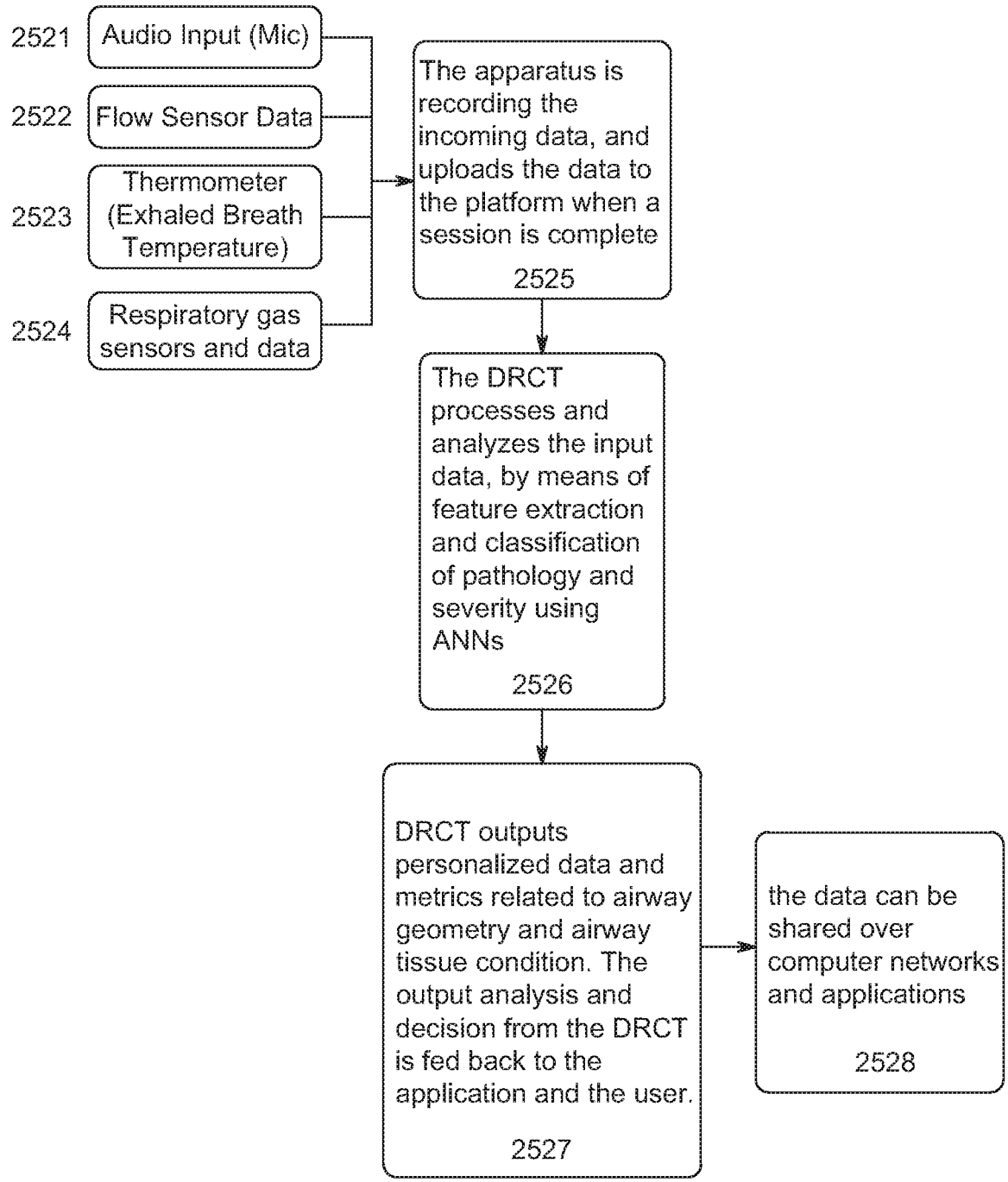
FIG. 25B illustrates an exemplary flow diagram indicating the manner in which the DRCT framework can be used in evaluating lung pathology where inputs are received from several different types of sensors in accordance with an embodiment of the present invention.

FIG. 25B illustrates an exemplary flow diagram indicating the manner in which the DRCT framework can be used in evaluating lung pathology where inputs are received from several different types of sensors in accordance with an embodiment of the present invention.

As shown in FIG. 25B, there can be different types of inputs into the DRCT procedure besides just a microphone (e.g., microphone 2521). For example, additional inputs can be received from a flow sensor 2522, a thermometer (to capture exhaled breath temperature) 2523, and additional respiratory gas sensors 2524.

At block 2525, the apparatus recording the incoming data can upload the data to the platform (e.g. software illustrated in FIGS. 5 and 21) when a session is complete.

At block 2526, the DRCT framework processes and analyzes the input data by means of feature extraction and classification of pathology and severity. In one embodiment, the feature extraction and classification is performed using artificial intelligence (AI) algorithms such as Deep Fully Convolutional Nueral Network (CNN) architectures or other artificial neural networks (ANNs).

The methodology and system that will be used to classify the recorded data according to disease pathology and severity and is based on artificial neural networks (ANNs). Artificial neural networks are widely used in science and technology. An ANN is a mathematical representation of the human neural architecture, reflecting its "learning" and "generalization" abilities. For this reason, ANNs belong to the field of artificial intelligence. ANNs are widely applied in research because they can model highly non-linear systems in which the relationship among the variables is unknown or very complex. Details regarding the manner in which this is done using neural networks will be discussed further in connection with the Training and Evaluation Modules of FIGS. 34 and 35.

At block 2527, the DRCT outputs characteristics and measurements that define a person's individualized airway geometry and morphology including the size and shape of the airways and the condition of the airway tissue. The output analysis and decision from the DRCT is fed back to the application and the user.

At block 2528, the data can be shared over computer network and with other applications as well.

As noted above, the apparatus for evaluating lung pathology may also optionally include a spirometer, a ventilator, a Continuous Positive Airway Pressure (CPAP) machine, an O2 device and a stethoscope.

Figure 26:
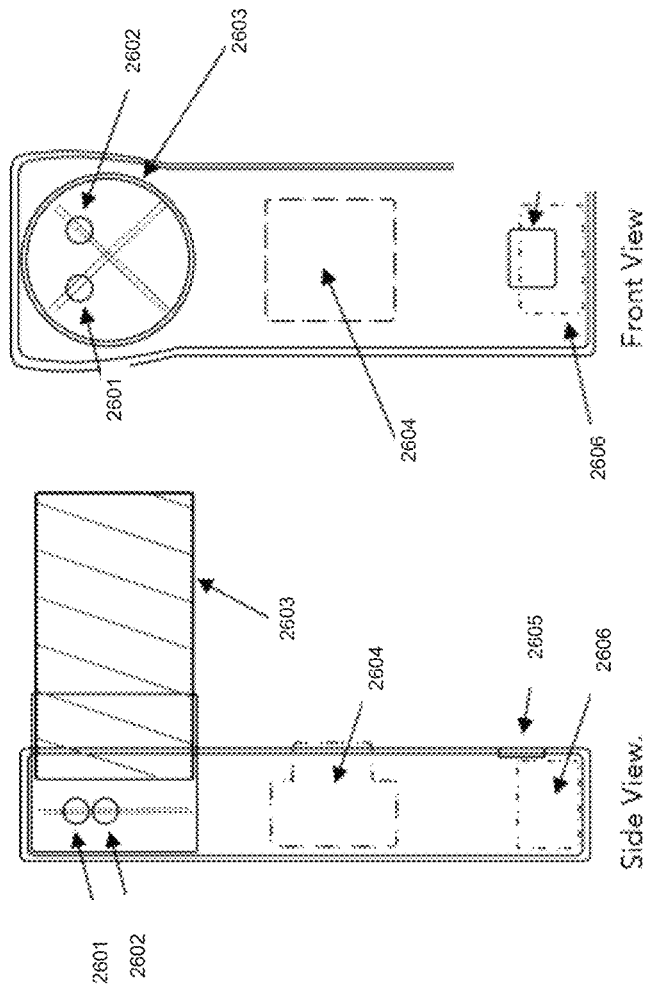
FIG. 26 illustrates a spirometer with built-in lung sound analysis in accordance with an embodiment of the present invention.

FIG. 26 illustrates a spirometer with built-in lung sound analysis in accordance with an embodiment of the present invention. The spirometer may comprise a microphone 2601, a flow sensor 2602 (e.g., a turbine, a differential pressure transducer), a disposable mouthpiece 2603, a Bluetooth controller 2604, a battery indicator 2605 and a USB connector/charger 2606. In one embodiment, the spirometer (a device with a flow sensor) comprises an added acoustic sensor or microphone 2601 and a flow sensor (or pressure transducer). The spirometer is a medical measurement device that a patient breathes into. It contains a flow sensor which measures respiratory activity and lung volumes in volumetric units. In other words, the flow sensor measures airflow volume and the speed of airflow in and out of the lungs to detect airflow limitation.

Conventional spirometers are not sensitive enough for precise diagnostics and tracking. For example, a certain percentage of people with lung disease have normal spirometry test results. Respiratory disease is heterogeneous in nature and can include both airflow limitations and lung sounds such as wheeze and crackles. Conventional spirometers, for instance, may only comprise a flow sensor (which may work to detect airflow limitation but not to recognize lung sounds such as wheeze and crackles). The flow sensor is used to measure lung volume and speed in liters per second. These measurements are used to diagnose and track lung disease, especially asthma and COPD. The problem with these measurements is that they may be too general for early detection and to predict exacerbations. Patients with lung disease or lung disease progression will get overlooked. It may also be difficult to use spirometry to differentiate asthma from COPD and to be correctly assess the severity.

Further, another challenge associated with using spirometry alone is that spirometry by itself may not be able to identify disease early, predict exacerbations, or differentiate one lung disease from another. Auscultation of the lungs for bronchial sounds such as wheeze and crackles has been used for centuries as a valuable tool for diagnosis and tracking disease, but is dependent on a doctor listening through a stethoscope or a patient reporting wheeze as a symptom. In both cases, the detection of lungs sounds will be limited to what a doctor and patient can hear.

Embodiments of the present invention add lung sound analysis to improve the sensitivity, and diagnostic and disease tracking capabilities. In other words, embodiments of the present invention add lung sound analysis to spirometry to improve diagnostic and disease tracking capabilities.

The lung sound analysis (e.g., using the DRCT framework) is added to the spirometers to provide additional diagnostic data. When a patient, for example, blows into the mouth piece, the maximum force or lung power is a sum of all of the airways as a single stream of air hits the flow sensor. Sound, however, reverberates as the air hits the airway walls. When there is obstruction, narrowing, inflammation or fluid present, it affects the pitch and characteristics of the sound. Accordingly, by adding sound analysis, embodiments of the present invention provide additional data points that can be analyzed to determine lung pathology. For example, the total amount of wheeze and the size and quality of the affected airways can be determined.

In one embodiment, the spirometer device simultaneously records airflow volumes and lung sounds. Standardized measurements of spirometry are combined with the dynamic classification of lung sounds, such as wheeze and crackles (from the DRCT framework), to improve the detection of the presence, progression and severity of lung pathology and disease.

In one embodiment, the spirometer can be connected to mobile devices or personal computers through a physical interface or by using a wireless transmission, e.g. Bluetooth. The power and recording controls may be placed physically on the device (using a digital signal processor, for example, embedded into the device) or may be located on the computer (or smart phone, tablet, laptop, etc.) that controls the device. In one embodiment, the data can also be automatically or manually uploaded and stored on a computer or other device. In one embodiment, the feature extraction and classification (related to the DRCT framework) are performed on a processor within the spirometer itself. In a different embodiment, the feature extraction and classification is performed on the computer that is connected to and controls the spirometer. For example, the spirometer may be connected to and controlled by a computer executing an application that performs feature extraction and classification of the lung sounds.

In one embodiment, the spirometer comprises a noise suppression module—the noise suppression module may have an additional microphone that may be used for recording and subtracting ambient noise. As mentioned above, conventional spirometers are not sensitive enough for precise diagnostics and tracking Embodiments of the present invention provide spirometers with higher sensitivity—one way for increasing the sensitivity is to equip the spirometers with noise suppression modules and sound analysis capabilities.

In one embodiment, there is a mouthpiece that may fit onto the microphone of a mobile phone or device with a microphone to accurately capture respiratory sounds. Embodiments of the present invention are advantageous because, in comparison with conventional methods, they also use acoustics to detect the presence, progression and severity of lung pathology and disease.

Embodiments of the present invention advantageously extract sound-based wheeze descriptors, spectrograms, spectral profiles, sound-based airflow descriptors and sound based crackle descriptors, all of which can detect and track both the audible and inaudible characteristics of wheezing and crackles that occur in breathing.

In one embodiment, as discussed in connection with FIG. 25B, the descriptors are fed into a machine learning system (e.g., Deep CNN, or other types of ANNs) that classifies a respiratory recording as healthy or unhealthy. Further, it determines the type of pathology, the disease and the severity (mild, moderate, severe). Examples of lung pathology can include infection, inflammation, and fluid. Examples of lung disease can include asthma, chronic obstructive pulmonary disease (COPD), pneumonia, whooping cough, and lung cancer. Examples of severity can include mild, moderate and severe. In addition, the machine learning system, according to embodiments of the present invention, compares respiratory recordings from the same individual to classify the onset, stability or progression of a lung pathology or disease over time.

III. A. Wheeze Descriptor Extraction

FIG. 10 above illustrates an exemplary computer-implemented process for the wheeze detection and classification module in accordance with an embodiment of the present invention. More specifically, FIG. 10 illustrates how ACF values can be calculated for each block of audio input signal and thereafter used to classify respective audio blocks as wheeze or tension.

Figure 27A:
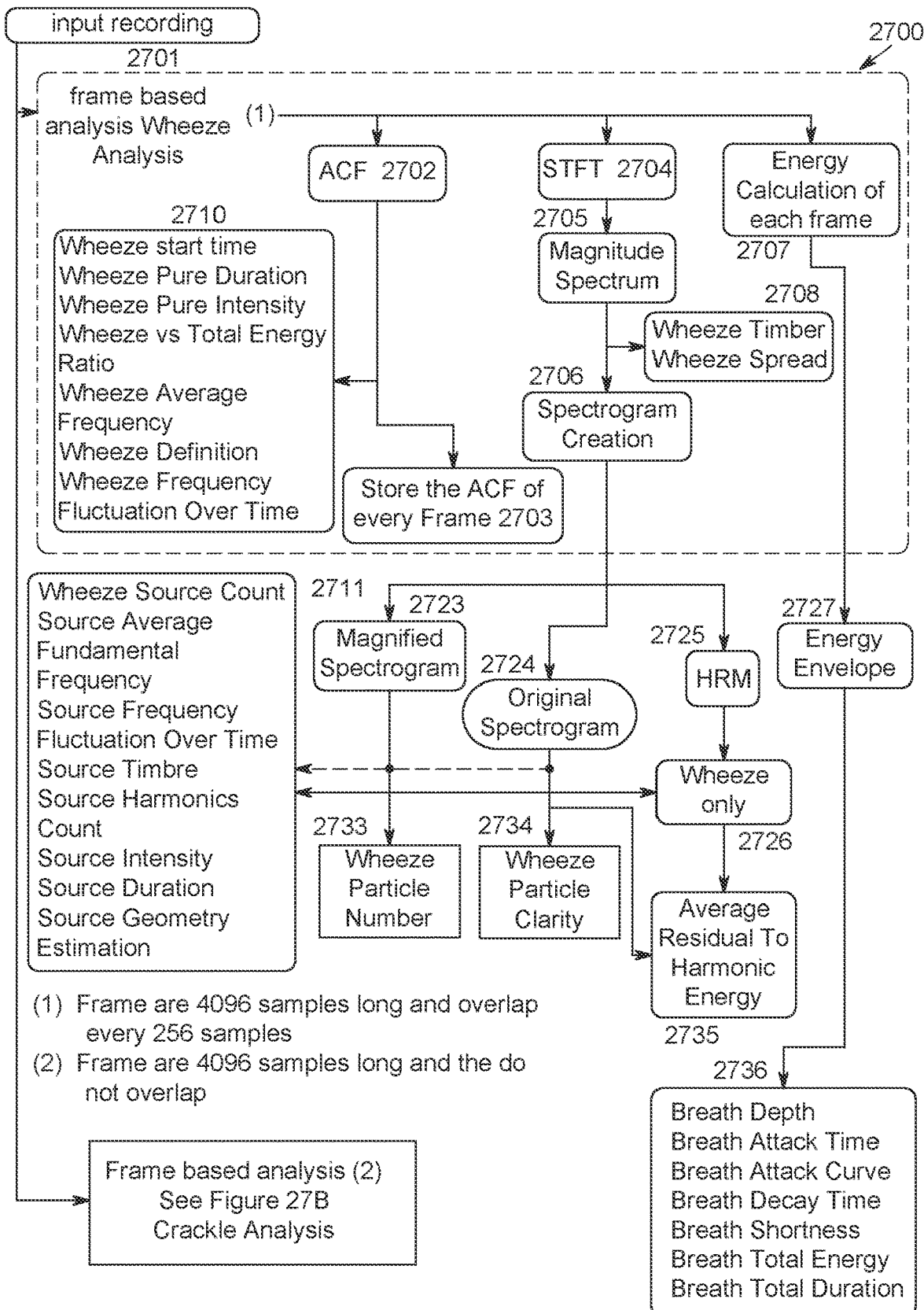
FIG. 27A illustrates a data flow diagram of a process that can be implemented to extract spectrograms and sound based descriptors pertaining to wheeze in accordance with an embodiment of the present invention.
Figure 27A:
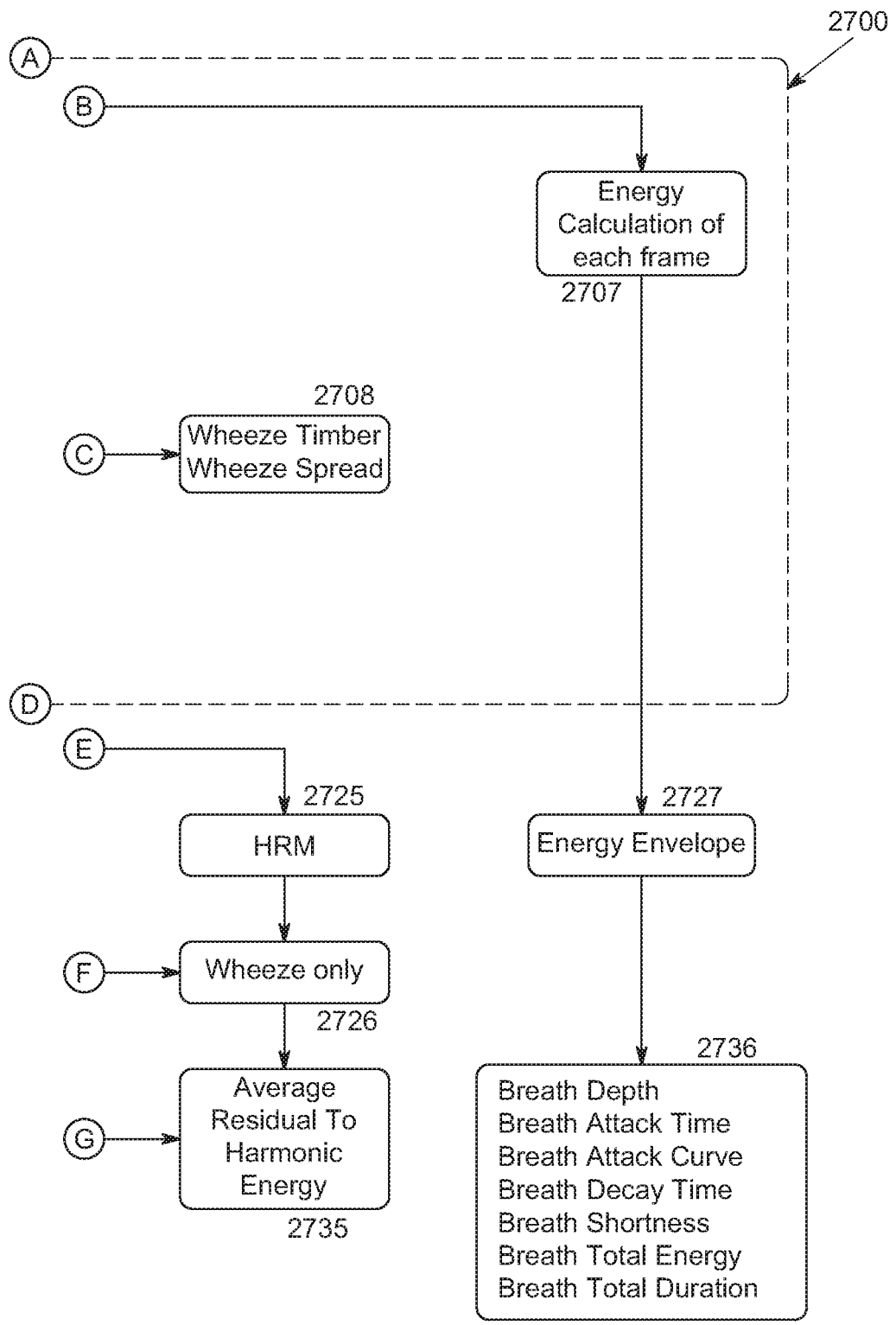

FIG. 27A illustrates a data flow diagram of a process that can be implemented to extract spectrograms and sound based descriptors pertaining to wheeze in accordance with an embodiment of the present invention. By extracting spectrograms, the method of FIG. 27A is able to provide more information than the method of FIG. 10. A spectrogram is a time-varying spectral representation that shows how the spectral density of a signal varies with time (it may also be known as a waterfall display).

A wheeze source is defined as a narrowed airway. When turbulent air hits the walls of a narrowed airway, sounds are produced that feature a fundamental frequency and its higher harmonics (or overtones). The spectrogram segments that correspond to these frequencies are called particles.

It should be noted that the difference between the spectrogram analysis illustrated in FIG. 27A from determining and analyzing the spectral patterns (as shown in FIGS. 10, 11A and 11B) is that the spectrogram analysis allows the software (running on the device or computer connected to the microphone or spirometer) to zoom in on the contents and behavior of a single wheeze or more than one wheeze. The spectrogram analysis also enables embodiments of the present invention to identify wheeze particles (fundamental frequencies and overtones that exist within a single wheeze but are not distinguishable by the human ear). By comparison, the spectral pattern analysis (discussed in connection with FIGS. 11A and B) does not provide as high a degree of resolution that the spectrograms allow.

FIG. 10 illustrates the manner in which linear predictive coding (LPC) can be used to identify wheeze. LPC works by applying filters that calculate coefficients to model the respiratory airways and anatomy. It is typically considered a 2 dimensional approach.

In the method discussed in connection with FIG. 27A (using spectrograms), embodiments of the present invention use spectrograms that comprise consecutive spectrums (e.g., 10 ms) that are produced using the Fast Fourier Transform (FFT)—this shows the output of the respiratory airways in terms of distribution of energy over frequency over time. This is typically considered a 3 dimensional approach and allows for a higher resolution than the 2 dimensional approach. In particular, it allows the software to zoom in on the contents and the behavior of the wheeze at a granular level.

Figure 30A:
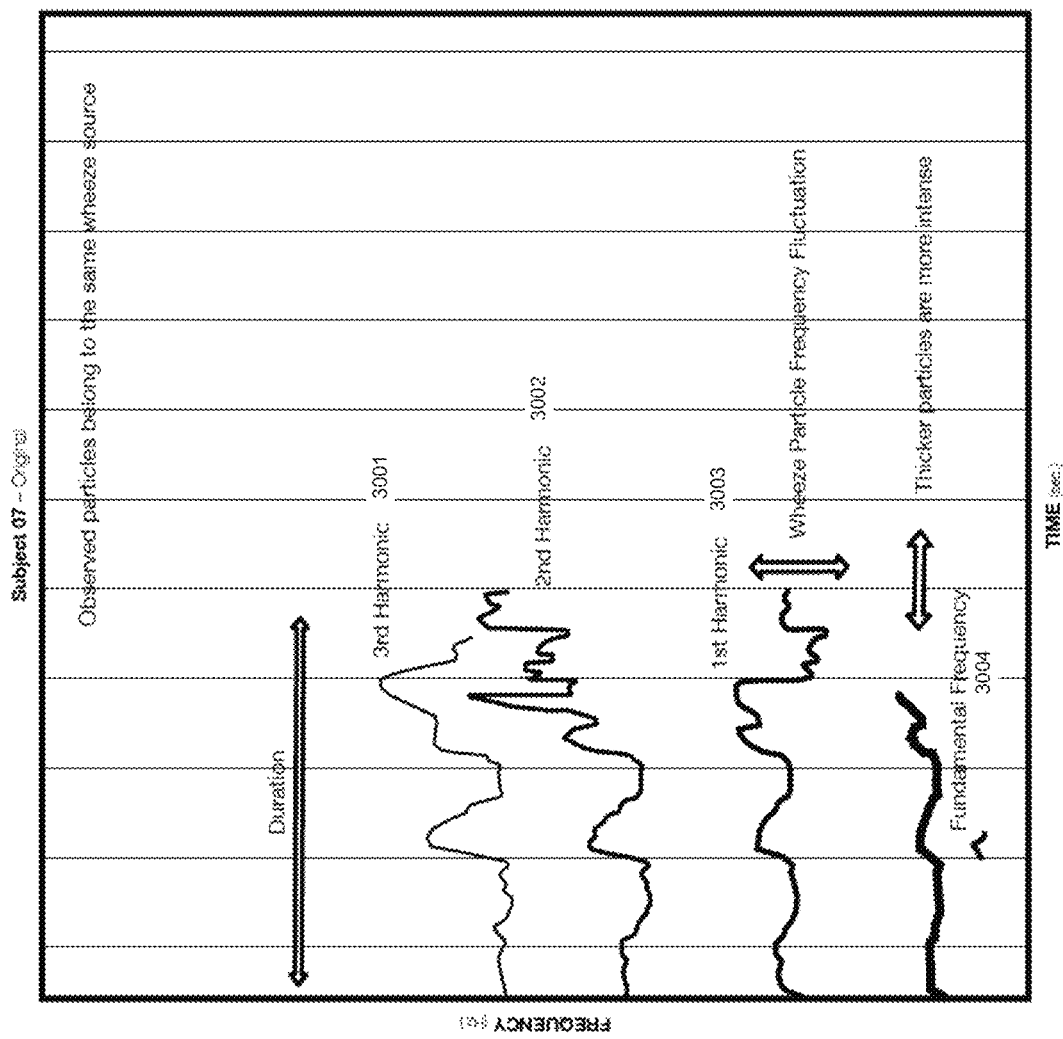
FIG. 30A is an exemplary spectrogram associated with the wheezing behavior of a hypothetical subject in accordance with an embodiment of the present invention.

FIG. 30A is an exemplary spectrogram associated with the wheezing behavior of a hypothetical subject in accordance with an embodiment of the present invention. For example, FIG. 30A is an exemplary spectrogram associated with subject "07." Each wheeze particle shown in FIG. 30A (namely 3001, 3002, and 3003) belongs to the same wheeze source and is a harmonic of the same source. Each of the wheeze particles has a separate frequency band (or harmonic). In other words, all the three harmonics shown in FIG. 30A (3001, 3002 and 3003) belong to and are extracted from the same wheeze source. The fundamental frequency of the wheeze is represented by waveform 3004—the thicker line represents more intense wheezing behavior.

As detailed earlier, sound based descriptors are extracted by first defining an area of interest. An area of interest can be a breath phase (inhalation, exhalation, cough), a breath cycle or more than one breath phases or breath cycles.

For wheeze analysis, each area of interest is analyzed using overlapping frames. Each frame is 4096 samples long and the overlap is 93% of their duration (every 256 samples). For example, if the sample rate is 44.100 Hz, each frame lasts 92 msecs and the frames overlap every 5 msecs. The values were chosen as such, in order to provide the most temporal and frequency accuracy. It should be noted however that each frame can have a varying number of samples and the overlap duration may also vary.

The sound recording 2701 from the patient is received into the wheeze analysis module 2700. For each frame, an ACF is determined at block 2702 (similar to FIG. 10). The ACF of every frame is stored at block 2703. At block 2710, several descriptors can be determined using the ACF values (without needing the spectrogram that is determined by module 2705), e.g., wheeze start time, wheeze pure duration, wheeze pure intensity, wheeze vs. total energy ratio, wheeze vs. total duration ratio, wheeze average frequency, wheeze frequency, wheeze definition and wheeze frequency fluctuation over time. It should be noted that the ACF values determined in FIG. 10 can also be used to determine the descriptors of block 2710.

It should be noted that all the descriptors extracted at blocks 2708, 2710, 2711, 2733, 2734, 2735 and 2736 are independent of one another and can be extracted at the same time.

As discussed above in connection with FIG. 10, wheezing can be identified with the ACF values calculated for each block or frame.

Wheeze Start Time

Figure 28:
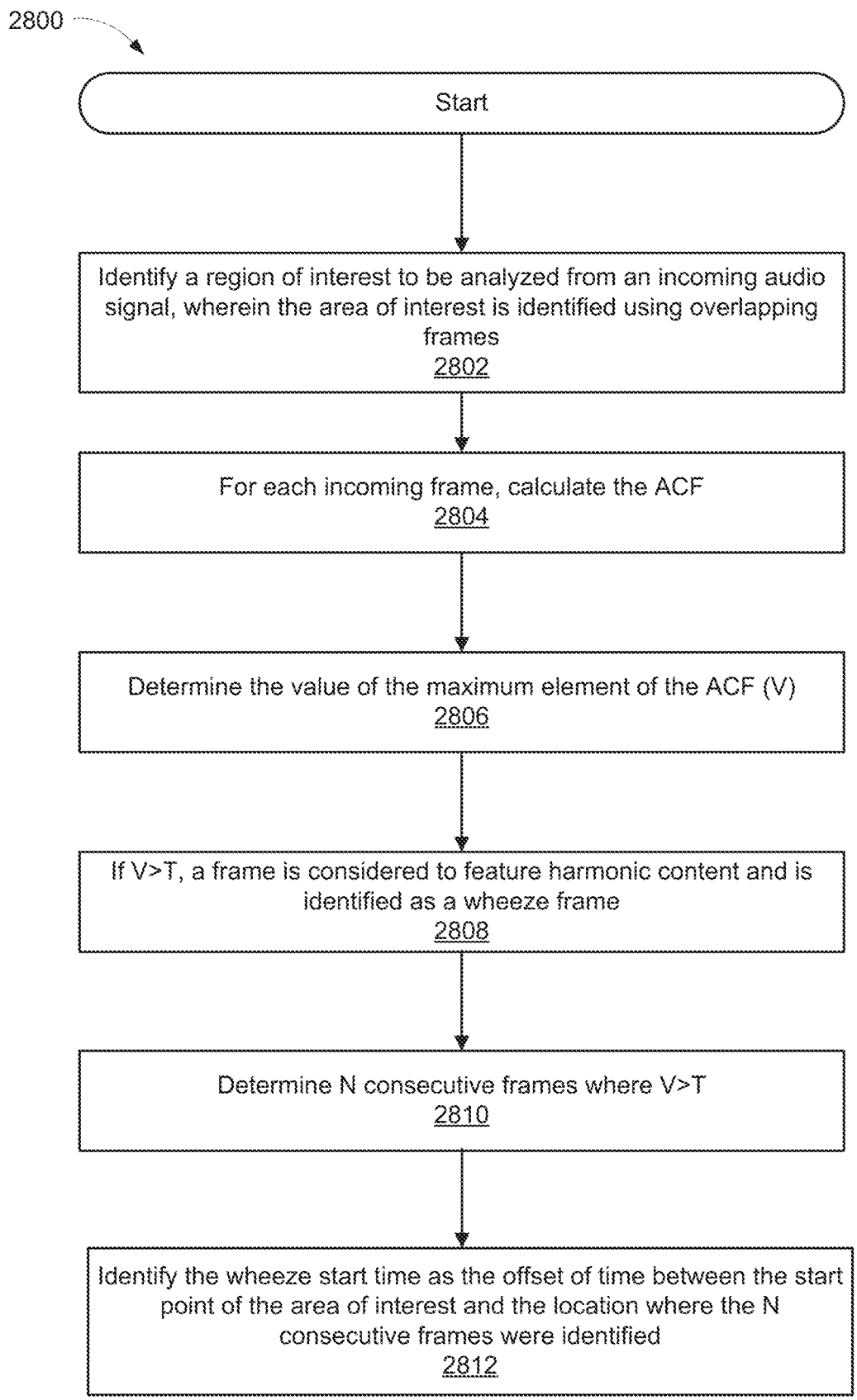
FIG. 28 depicts a flowchart 2800 illustrating an exemplary computer-implemented process for detecting the wheeze start time in accordance with one embodiment of the present invention.

FIG. 28 depicts a flowchart 2800 illustrating an exemplary computer-implemented process for detecting the wheeze start time in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 28 should not be construed as limiting the scope of the invention. Rather, it will be apparent to persons skilled in the relevant art(s) from the teachings provided herein that other functional flows are within the scope and spirit of the present invention. Flowchart 2800 may be described with continued reference to exemplary embodiments described above, though the method is not limited to those embodiments.

At step 2802, as noted above, an area or block of interest from the audio signal is identified. Each area of interest is analyzed using overlapping frames. Each frame is 4096 samples long and the overlap is 93% of their duration (every 256 samples). The sample rate is 44.100 Hz which means that each frame lasts 92 msecs and the frames overlap every 5 msecs. As noted above, the frames are not limited to being 4096 samples and similarly the overlap duration is also not limited.

At step 2804, for every incoming frame, the software calculates the autocorrelation function (ACF). In one embodiment, the ACF calculations are normalized to the first value so that the maximum value is 1.0. Further, the frequency range of the ACF values can be restricted to be between 100 Hz and 1 KHz.

At step 2806, the value of the maximum element of the ACF is determined for each frame.

At step 2808, the maximum value determined for the frame (V) is compared with a predetermined threshold value (T). In other words T is a predetermined threshold value. If the maximum ACF value determined for the frame is greater than T (V>T), the frame is considered to feature harmonic content and it is designated as a wheeze frame. In one embodiment, T is determined empirically and can be between a range of 0.3 to 0.5—if T falls between the range then the frame is considered to feature harmonic content.

At step 2810, if more than N consecutive frames share the property of V>T (where N is the number of frames such that their accumulated duration is greater than 5 milliseconds), the N frames are identified as the start of wheezing.

At step 2812, the offset of time between where the area of interest (identified at step 2802) started and where the N consecutive frames were identified is designated as the Wheeze Start Time.

As noted above, besides Wheeze Start Time, at block 2710, several other descriptors can also be determined using the ACF values, e.g., wheeze pure duration, wheeze pure intensity, wheeze vs. total energy ratio, wheeze vs. total duration ratio, wheeze average frequency, wheeze frequency, wheeze definition and wheeze frequency fluctuation over time. These parameters that are also determined at block 2710 will be discussed below.

Wheeze Pure Duration

The summation of the duration of all the events that are counted as wheeze events, based on the criteria mentioned above, results in the total Wheeze Pure Duration.

Wheeze Pure Intensity

The summation of the intensity of all the frames that have been identified as wheeze frames as described above determines the Wheeze Pure Intensity.

Wheeze Vs. Total Duration Ratio

This descriptor is the ratio of the accumulated duration of all the frames considered as wheeze to the total duration of the Area of Interest.

Wheeze Vs. Total Energy Ratio

To calculate the Wheeze vs. Total Energy Ratio, the software summarizes the energy of the frames accepted as wheeze frames and divides it by the total energy of the Area of Interest. The energy of each frame is calculated as follows:

$$E = \frac{1}{N} \sum_{i=0}^{N} x_i^2$$

where N is the frame length (4096 samples) and x is each sample in the frame.

Wheeze Average Frequency

To calculate the average frequency, the frequency of each particle is calculated. The frequency of the particle can be calculated by determining the position of the ACF where its maximum value is located.

The particle's frequency is defined as $$f_0 = \frac{fs}{N}$$

where $f_0$ is the wheeze particle's most prominent frequency and $f_s$ the sample rate of the audio recording.

The average wheeze frequency is given by the following formula:

$$f_{avg} = \frac{1}{N} \sum_{i=0}^{N} f_i.$$

Wheeze Definition

The Wheeze Definition is measured by using the maximum value of the ACF of each wheeze frame. High values indicate that the harmonic connected to wheeze pattern is more clear, whereas lower values indicate a less harmonic wheeze pattern. The wheeze definition is defined as the average of the maximum values of the ACF of the wheeze frames.

Wheeze Frequency Fluctuations Over Time

Frequency fluctuation over time is defined as the variance of the frequency of wheeze frames that comprise wheeze particles. This means that the frames should be consecutive without interruptions for more than a predefined duration.

For each incoming frame into module 2700, a Short-Time Fourier Transform (STFT) is calculated at block 2704. Alternatively, in a different embodiment, a Fast Fourier Transform (FFT) may be determined at block 2704.

At block 2705, a magnitude spectrum for each frame is determined using the information from the STFT or the FFT. The STFT (or FFT) and the magnitude spectrum are used to create the sound based descriptors and spectrograms (that could not be extracted using only the ACF values). As mentioned above the spectrograms allow the software to zoom in on the contents and behavior of the wheeze, thereby, advantageously improving the functionality of the computing device.

At block 2708, the wheeze timbre and wheeze spread descriptors are determined.

Wheeze Timbre

The wheeze timbre is calculated by averaging the spectral centroid of the wheeze frames. The spectral centroid is a measure used in digital signal processing to characterize a spectrum—it indicates where the "center of mass" of the spectrum is located. The spectral centroid of every wheeze frame is given by $$\mu = \sum_i x_i \cdot p(x_i)$$

where $x_i$ is the magnitude of the frequency bin i and p(x) the probability to observe x $$p(x) = \frac{S(x)}{\sum_x S(x)}$$

where S is the frequency spectrum and x is the bin index.

Wheeze Spread

The wheeze spread is calculated by averaging the spectral spread of the wheeze frames. The spectral spread of every wheeze frame is given by $$\sigma^2 = \sum_i (x_i - \mu) \cdot p(x_i)$$

where $x_i$ is the magnitude of the frequency bin i and $\mu$ the spectral centroid.

At block 2706, the spectrogram is created. At block 2723 a magnified spectrogram is created which is used to determine the wheeze particle number descriptor at block 2733. A magnified spectrogram is created because it can be used to identify wheeze particles more clearly than the original spectrogram created at block 2724.

Figure 30B:
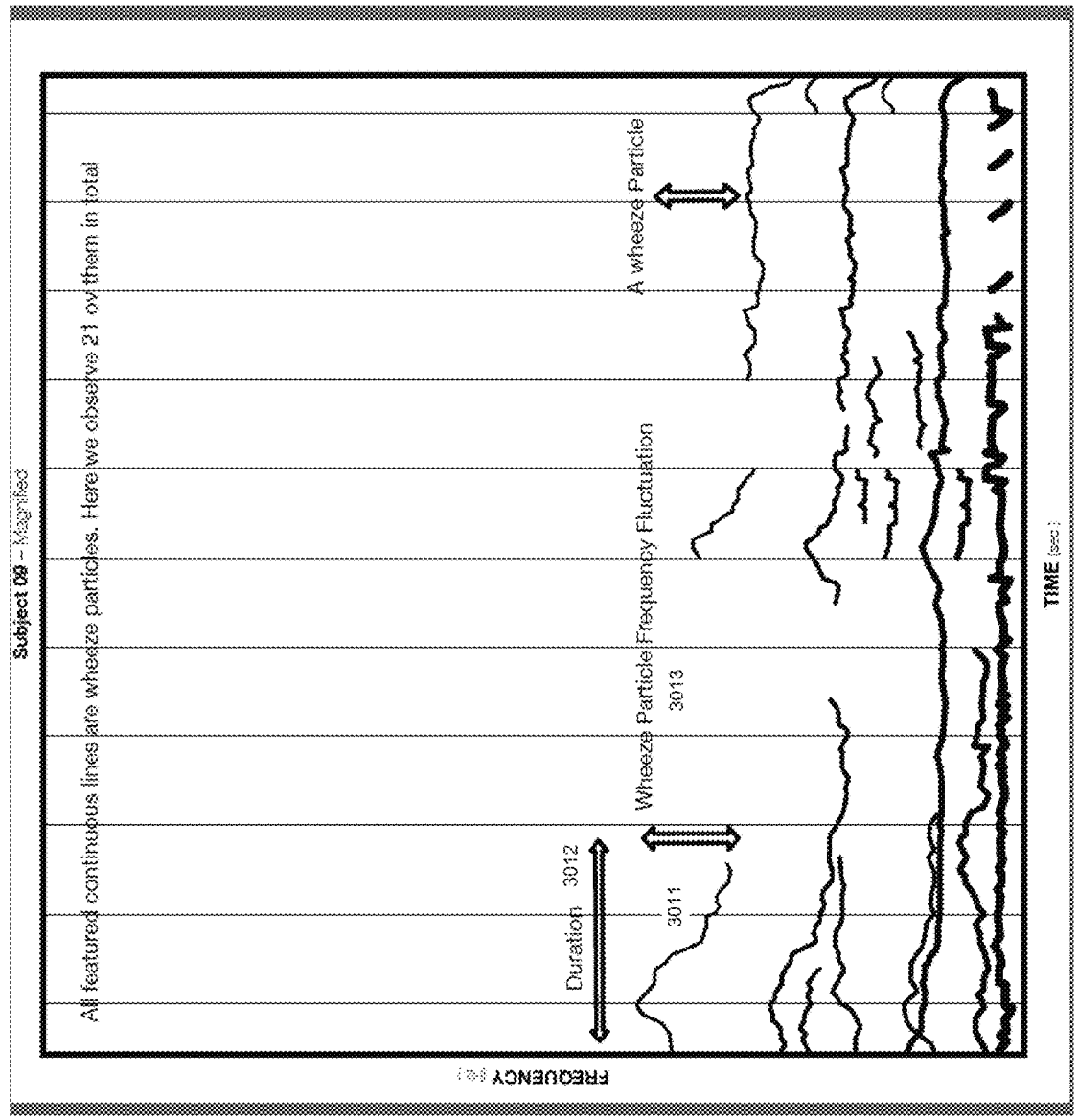
FIG. 30B illustrates an exemplary magnified spectrogram associated with the wheezing behavior of a hypothetical subject in accordance with an embodiment of the present invention.

FIG. 30A, as discussed above, illustrates a spectrogram associated with the wheezing behavior of hypothetical subject "07". FIG. 30B illustrates an exemplary magnified spectrogram associated with the wheezing behavior of a hypothetical subject in accordance with an embodiment of the present invention. For example, FIG. 30B is associated with the wheezing behavior of a hypothetical subject "09." FIG. 30B is an example of a magnified spectrogram determined at block 2723. All the continuous lines shown in FIG. 30B are associated with wheeze particles. In total, FIG. 30B contains information about 21 different wheeze particles—these wheeze particles can easily be identified visually because the spectrogram is magnified (in comparison to the original spectrogram of FIG. 30A). For example, wheeze particle 3011 has duration 3012 and a frequency fluctuation span 3013.

Figure 31A:
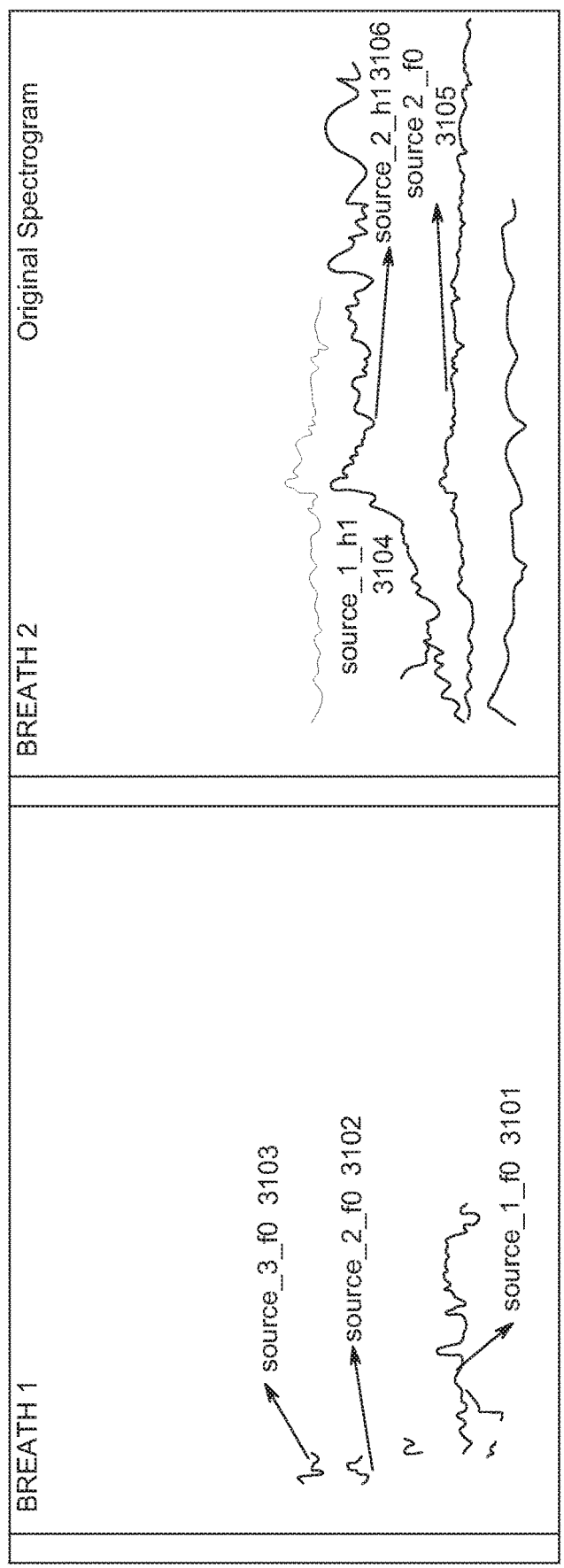
FIG. 31A illustrates an exemplary spectrogram associated with the wheezing behavior of a hypothetical subject in accordance with an embodiment of the present invention.
Figure 31B:
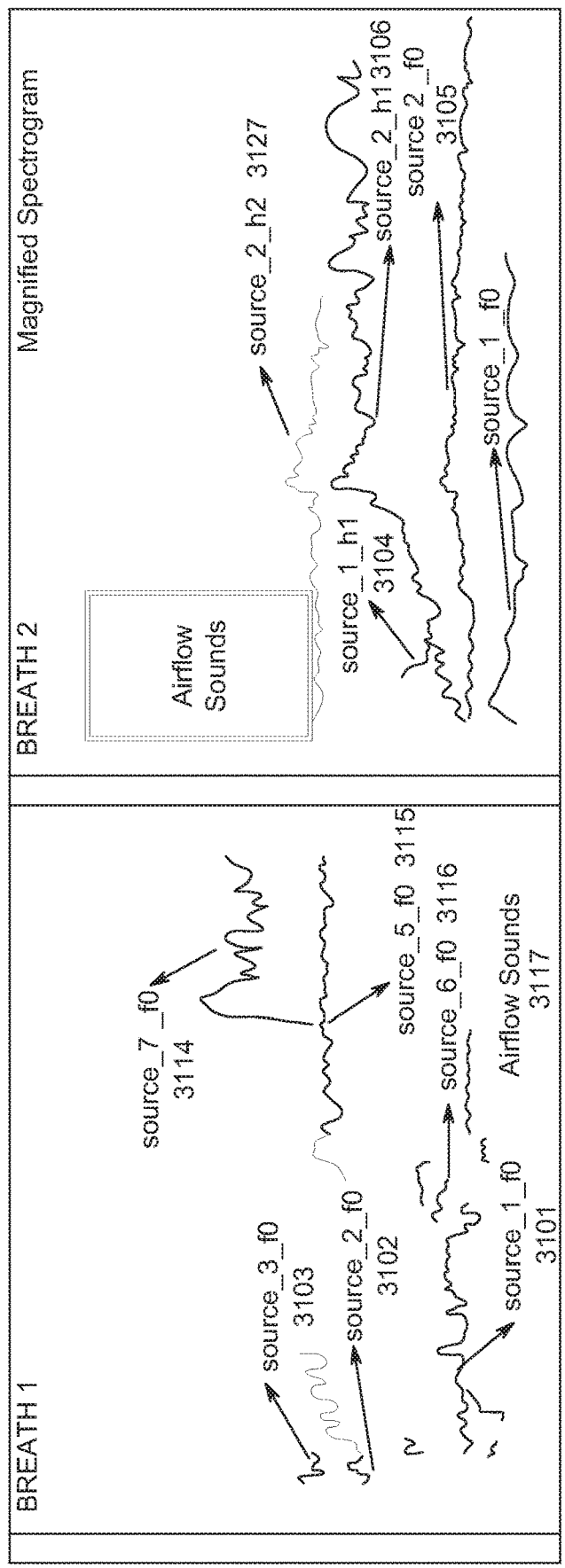
FIG. 31B illustrates an exemplary magnified spectrogram which is a magnified version of the spectrogram shown in FIG. 31A in accordance with an embodiment of the present invention.
Figure 31C:
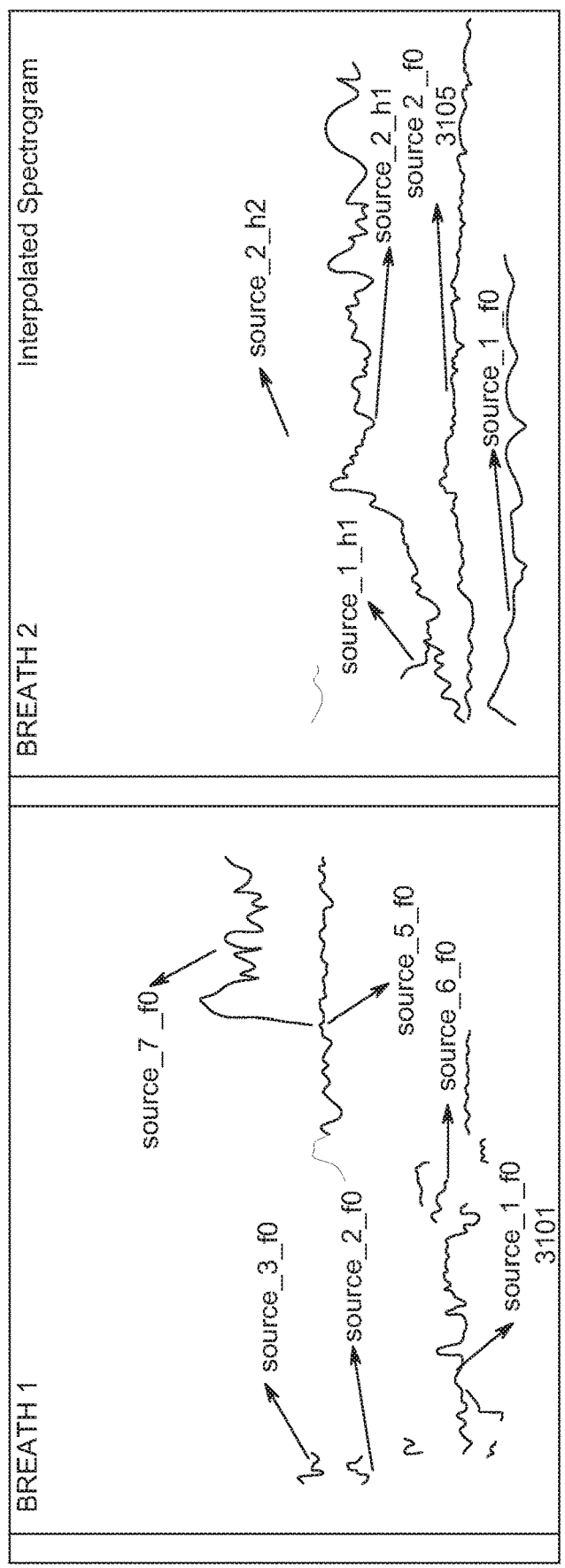
FIG. 31C illustrates a wheeze-only spectrogram associated with the wheezing behavior of a hypothetical subject shown in FIG. 30A in accordance with an embodiment of the present invention.

It should be noted that spectrograms illustrated in both FIGS. 30A and 30B are exemplary and have been used for purposes of illustration. FIGS. 31A-31C, by comparison (discussed further below) comprise examples of actual spectrograms extracted from a breathing sound recording of a patient.

Wheeze Particle Number

To calculate the number of wheeze particles, the magnified spectrogram is used where each contributing magnitude spectrum is normalized to each frame's maximum value, making all possible wheeze particles visible. Normalizing to each frame's maximum value magnifies the wheeze particles making each wheeze particle visible.

In one embodiment, an edge detection algorithm may be used (e.g. Sobel with vertical direction), or any other high pass filter operating column-wise on the magnified spectrogram image. The abrupt color changes that happen when wheeze frames occur produce a high value output. This operation is similar to "image equalization." The spectrograms are treated as images here. Images comprise rows and columns. The normalization is carried out for every column in the spectrogram by dividing the elements of that column with the maximum value of the same column. So, even if the elements of a specific column have small values, when divided by the maximum element, the range of the values for this column is normalized within [0,1] (where 0 is the white color and 1 is the black color). The same process is repeated even if the values within a spectrogram column are high. The result is that all the columns of the spectrogram have the same range [0,1]. This way even particles that are weak in energy show up on the same spectrogram as the high energy ones.

As shown in FIG. 30B, a continuous line is considered a wheeze particle if it crosses over a certain threshold duration. For example, if a continuous line on a magnified spectrogram lasts more than, for example, 5 msecs, the particle count augments by one.

At block 2724, the original spectrogram that was created at block 2706 is used to determine wheeze particle clarity descriptor at block 2734.

Wheeze Particle Clarity

To calculate wheeze particle clarity, the original spectrogram determined at block 2706 is used. The result is the accumulation of the output of a high pass filter that processes the spectrogram image column-wise. After the accumulation takes place, the results are divided by the total number of pixels in the spectrogram image. Clear and intense particles usually occurring with more severe wheeze are characterized by a rapid change in color from light to dark. In other words, the wheeze particles associated with more severe pathologies will appear as darker continuous lines on the spectrograms.

FIGS. 31A-31C illustrate the manner in which spectrograms can illustrate wheeze particle clarity in accordance with an embodiment of the present invention.

FIG. 31A illustrates an exemplary spectrogram associated with the wheezing behavior of a hypothetical subject in accordance with an embodiment of the present invention. FIG. 31A comprises spectrograms extracted from two breath cycles, breath 1 and breath 2. Breath 1 comprises three separate wheeze sources, source_1 3101, source 2 3102 and source 3 3103. The fundamental frequency, f0, for each of the wheeze sources is visible on the spectrogram. With respect to breath 2, the first harmonic of wheeze source_1 3104 and the first harmonic of wheeze source_2 3106 are visible. Further, the fundamental frequency of source_2 3105 is also visible on the spectrogram.

As mentioned above, clear and intense particles usually occurring with more severe wheeze are characterized by a rapid change in color from light to dark. As shown in FIG. 31A, during breath 1, source_1 3101 varies in color from light to dark indicating a more severe wheeze. Similarly, during breath 2, source_2 3105 transitions from a lighter color to a darker color also indicating severe wheezing behavior.

FIG. 31B illustrates an exemplary magnified spectrogram which is a magnified version of the spectrogram shown in FIG. 31A in accordance with an embodiment of the present invention. As seen in FIG. 31B, several more wheeze particles are visible because of the magnification. In addition to the wheeze particles that were already visible in FIG. 31A, additional wheeze particles can also be seen in FIG. 31B. For example, the fundamental frequency of source_5 3115, the fundamental frequency of source_6 3116 and the fundamental frequency of source_7 3114 are visible in breath 1 of FIG. 31B. Furthermore, residual airflow sounds 3117 may also be visible on the magnified spectrogram. Similarly, in breath 2, the second harmonic of source_2 3127 is visible (which was not perceptible in the original spectrogram of FIG. 31A).

Another method to determine wheeze particle clarity is the following:

$$WPC = \frac{\sum_i \sum_j S(i,j)}{M \cdot N}$$

where S the spectrogram image, M the image width in pixels, N the image height in pixels, and WPC the wheeze particle clarity.

Average Residual to Harmonic Energy

At block 2725, the Harmonic+Residual Model (HRM) is determined.

Subsequently, at block 2726, the wheeze-only spectrogram is determined. This is used to determine the Average Residual to Harmonic Energy descriptor at block 2735 as will be explained further below. Note that the Average Residual to Harmonic Energy descriptor is the result of the calculation of the HRM.

The HRM is a modeling of the spectrum and, by extension, a modeling of the spectrogram. The modeling process receives a spectrum or spectrogram as an input. The HRM block 2725 may receive either the magnified spectrogram 2723 or the original spectrogram 2724 as an input. A peak detection algorithm is employed to detect the locations and the values of the magnitude spectrum peaks. The peaks that are above a threshold (e.g., the threshold can be set at −12 dB) are interpolated with a Blackman-Harris window. The interpolated spectrogram is the harmonic part of the model. In other words, the interpolated spectrogram comprising the harmonic part of the spectrum is the wheeze-only spectrogram. The residual part is obtained by subtracting the interpolated spectrum from the original one. The residual part comprises the residual airflow energies—subtracting out the residual part from the original spectrogram yields the wheeze-only or interpolated spectrogram.

The wheeze-only spectrogram may be better suited for viewing (and analyzing by the ANN) than the magnitude spectrogram because without the noise added in by the residual airflow energies, the wheeze particles can be clearly viewed on the spectrogram.

FIG. 31C illustrates a wheeze-only spectrogram associated with the wheezing behavior of a hypothetical subject shown in FIG. 31A in accordance with an embodiment of the present invention. As seen in FIG. 31C, with the residual airflow energies filtered out, the wheeze particles can be identified more clearly than in the original or magnified spectrograms of FIGS. 31A and 31B. For example, the wheeze particles for both source_1 3101 and source_2 3105 can be identified more clearly in FIG. 31C as compared to its counterparts FIGS. 31A and 31B.

As noted above, the purpose of the Average Residual to Harmonic Energy descriptor determined at block 2735 is to isolate harmonic wheeze sounds and separate them from the simultaneously occurring airflow sounds (or the residual sounds). In other words, the residual refers to the simultaneous airflow sounds that are underneath the wheeze sounds, or occurring at the same time as the wheezing sounds.

To calculate the average residual to harmonic energy, the software extracts an original spectrogram (or magnitude spectrogram), where all of the magnitude spectrum frames are normalized to the maximum intensity value of the entire area of interest.

Using this normalized spectrogram, the software then creates a wheeze-only spectrogram. When a frame is considered to feature harmonic content that is inherent in wheeze sounds, it is normalized and stored into a new spectrogram table. If a frame is not considered as harmonic, then the corresponding table position is filled with zeros.

Subsequently, each magnitude frame that is considered harmonic goes through a peak detection process to detect peaks that lie within the range of (0-12 dB) but at the same time the column-wise Original Spectrum Derivative exceeds a predefined threshold. The locations of these peaks are interpolated with a Blackman-Harris Window that is weighted with the detected peak magnitude value each time.

The resulting spectrogram is then subtracted from the original one, thus the result will not contain the detected wheeze frames (but will contain the residual spectrogram). To calculate the residual airflow energy within the wheeze frames, the software accumulates the values of the residual spectrogram at the indexes that correspond to wheeze frames.

Descriptors Related to Wheeze Source

At block 2711, using the wheeze spectrogram from block 2726, several descriptors pertaining to the wheeze source are determined including source duration threshold, maximum number of harmonics, source frequency search range, wheeze source count, source average fundamental frequency, source frequency fluctuation over time, source timbre, source harmonics count, source intensity, source duration, source significance, and source geometry estimation. Each of these descriptors will be discussed further below.

As mentioned earlier, a wheeze source is defined as a narrowed airway. When turbulent air hits the walls of a narrowed airway, sounds are produced that feature a fundamental frequency and its higher harmonics (or overtones). The spectrogram segments that correspond to these frequencies are called particles. The fundamental frequency or pitch of the source is strongly connected to its geometry and how it changes over time. The number and intensity of the harmonics are connected to the force of the airflow and the tissue characteristics of the airway sources. For example, airway tissue that is more firm will produce more harmonics, while airway tissue that is softer and inflamed may produce fewer harmonics. Airways that contain fluid will dampen and reduce the harmonics. For example, as seen in FIG. 30A, the wheeze source comprises a fundamental frequency 3004 and three associated harmonics (3001, 3002 and 3003). The wheeze source for the wheeze particles shown in FIG. 30A may be an airway tissue that is firm—accordingly, it produces multiple harmonics.

Sometimes different sources have almost identical frequency characteristics in terms of pitch, number of harmonics and harmonic intensity, thus they overlap. In this case, in one embodiment, the software may define a frequency range around a detected particle of a few hertz that is connected to the first detected particle. This means that there will not be further searching for more particles within this range.

Figure 29:
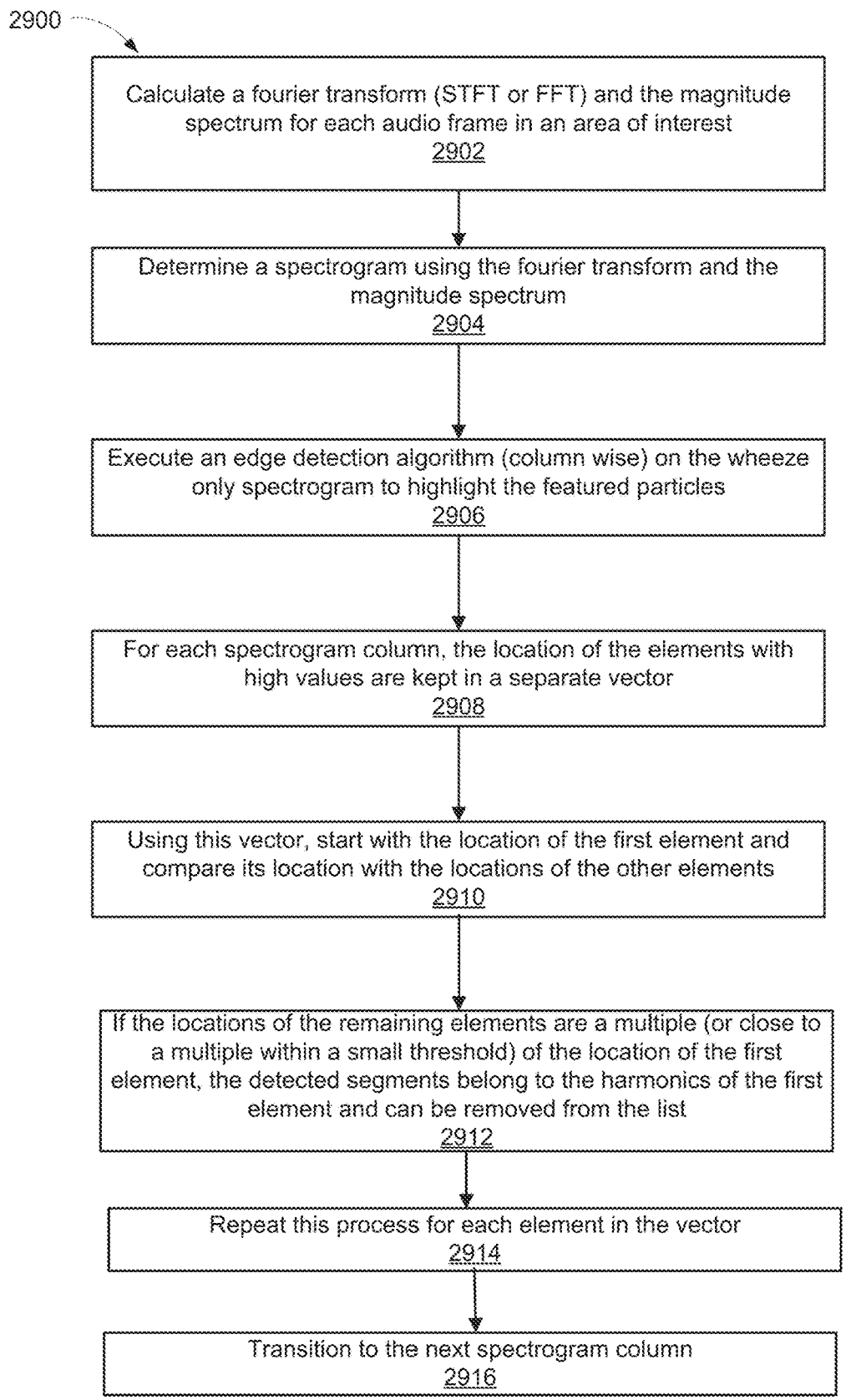
FIG. 29 depicts a flowchart 2900 illustrating an exemplary computer-implemented process for determining wheeze source in accordance with one embodiment of the present invention.

FIG. 29 depicts a flowchart 2900 illustrating an exemplary computer-implemented process for determining wheeze source in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 29 should not be construed as limiting the scope of the invention. Rather, it will be apparent to persons skilled in the relevant art(s) from the teachings provided herein that other functional flows are within the scope and spirit of the present invention. Flowchart 2900 may be described with continued reference to exemplary embodiments described above, though the method is not limited to those embodiments.

At step 2902, a STFT or FFT and the magnitude spectrum for each audio frame in an area of interest is determined as indicated above (in connection with blocks 2704 and 2705 of FIG. 27A).

At step 2904, a spectrogram is created (as discussed in connection with block 2706 of FIG. 27A).

At step 2906, the software executes an edge detection algorithm (column wise) on the spectrogram (e.g., the wheeze only spectrogram created at block 2726) to highlight the featured particles.

At step 2908, for each spectrogram column, the locations of the elements with high values are stored in a separate vector.

At step 2910, using this vector, the software starts with the location of the first element and compares its location with the locations of the remaining ones.

At step 2912, if the locations of the remaining elements in the vector are a multiple (or within a small range of the multiple) of the location of the first element, the detected segments belong to the harmonics of the first element, and they are removed from the list.

At step 2914, this process is repeated for all the elements in the vector until there are no remaining elements in the vector.

At step 2916, the vector is created for the next spectrogram column and the process is repeated.

It should be noted that if the continuity of the lowest in frequency particle breaks before a duration threshold has been reached, nothing gets assigned to that source. In other words, if a particle duration is less than the duration threshold, nothing gets assigned to that source.

As mentioned above, there are several descriptors pertaining to the wheeze source, which are also determined at block 2711.

Source duration threshold: The particles associated with the fundamental frequency of a wheeze source should exceed a duration threshold in order to be assigned to a possible source. In one embodiment, this duration threshold is set to 5 milliseconds.

Maximum Number Of Harmonics: In one embodiment, the software can be programmed to search for 5 harmonics per wheeze source (or fewer). In different embodiments, this can be set higher than 5 harmonics.

Source frequency search range: The frequency range of the occurring particles that may be considered as source fundamentals is defined to start at 100 Hz going up to 1 KHz.

Wheeze Source Count: The number of the featured wheeze sources.

Source Average Fundamental Frequency: The average source fundamental frequency. This may also be referred to as the average pitch of the featured sources.

Source Frequency Fluctuation Over Time: The average of the frequency fluctuation over time of a fundamental frequency for each source.

Source Timbre: The source timbre is a measure of the brightness of the source. Each source features a fundamental frequency and a number of harmonics. The location of the fundamental frequency, the number of harmonics and the intensity of the harmonics define the timbre of the source as follows:

$$\tau = \sum_k \sum_i^N x_i \cdot p(x_i)$$

where $x_i$ is the magnitude of the frequency bin i and p(x) the probability to observe x:

$$p(x) = \frac{S(x)}{\sum_x S(x)}$$

and S(x) represents each column of the wheeze spectrogram.

Source Harmonics Count: This descriptor is related to the average number of harmonics that each source has.

Source Intensity: The average intensity of the featured sources.

Source Duration: The overall duration of the featured sources.

Source Significance: This descriptor is a combination of a few different source characteristics. Specifically, it is the product of the average intensity, duration and pitch.

Source Geometry Estimation: This descriptor provides the dimensions of the resonating wheeze source. This is associated with the source pitch.

Sound Based Airflow Descriptor Extraction

In addition to descriptors pertaining to wheezes, module 2700 also determines descriptors pertaining to the airflow recorded as part of the incoming audio recording 2701, e.g., at block 2736 the software determines breath depth, breath attack time, breath attack curve, breath decay time, breath shortness, breath total energy and breath total duration.

The process to extract the descriptors at block 2736 is similar to the other descriptors. For example, the overlapping block based scheme discussed above is used and for every block, the software extracts the associated descriptors.

At block 2707, the energy value for each frame is calculated and at block 2727 the energy envelope for each frame is determined.

The energy envelope of the input signal is extracted as follows:

For every frame(i), the software calculates $$e_i = \sum_k |x_k|, \ i = 0, 1, \ldots N,$$

where $x_k$ is the $k_{th}$ sample within the frame and e(i) is the energy of the frame.

The descriptors determined at block 2736 are as follows:

Breath Area of Interest (A.O.I.) Depth: The value of this descriptor is calculated as follows:

$$BD = \frac{\sum_i e_x}{\sum_i m}$$

where m the maximum value of $e_x$ and $e_x$ the envelope of the A.O.I

Breath A.O.I Attack Time: The time in seconds it takes from the A.O.I start until it reaches the 80% of its maximum energy.

Breath A.O.I Attack Curve: The value of this descriptor is calculated as follows:

$$c = \sum \frac{d^2 e_x}{dx},$$

in other words the sum of the second derivative of the envelope of the A.O.I at this stage.

Breath A.O.I Decay Time: The time it takes for the A.O.I to drop down to 10% of the peak of its energy or intensity.

Breath A.O.I Shortness: The time difference Total A.O.I Duration−Decay Time−Attack Time.

Breath A.O.I Total Energy: The total energy of the A.O.I defined as $$E = \frac{1}{N}\sum_i^N x_i^2.$$

Breath A.O.I Total Duration: The total duration of the A.O.I

III. B. Crackle Descriptor Extraction

Crackles are impulse like short periodic sounds that repeat rapidly during a defined area of interest. The frequency range of each occurring crackle lies within 100 to 300 Hz.

The frames in the frame based analysis pertaining to crackles can be 4096 samples long but they are not required to overlap.

Figure 27B:
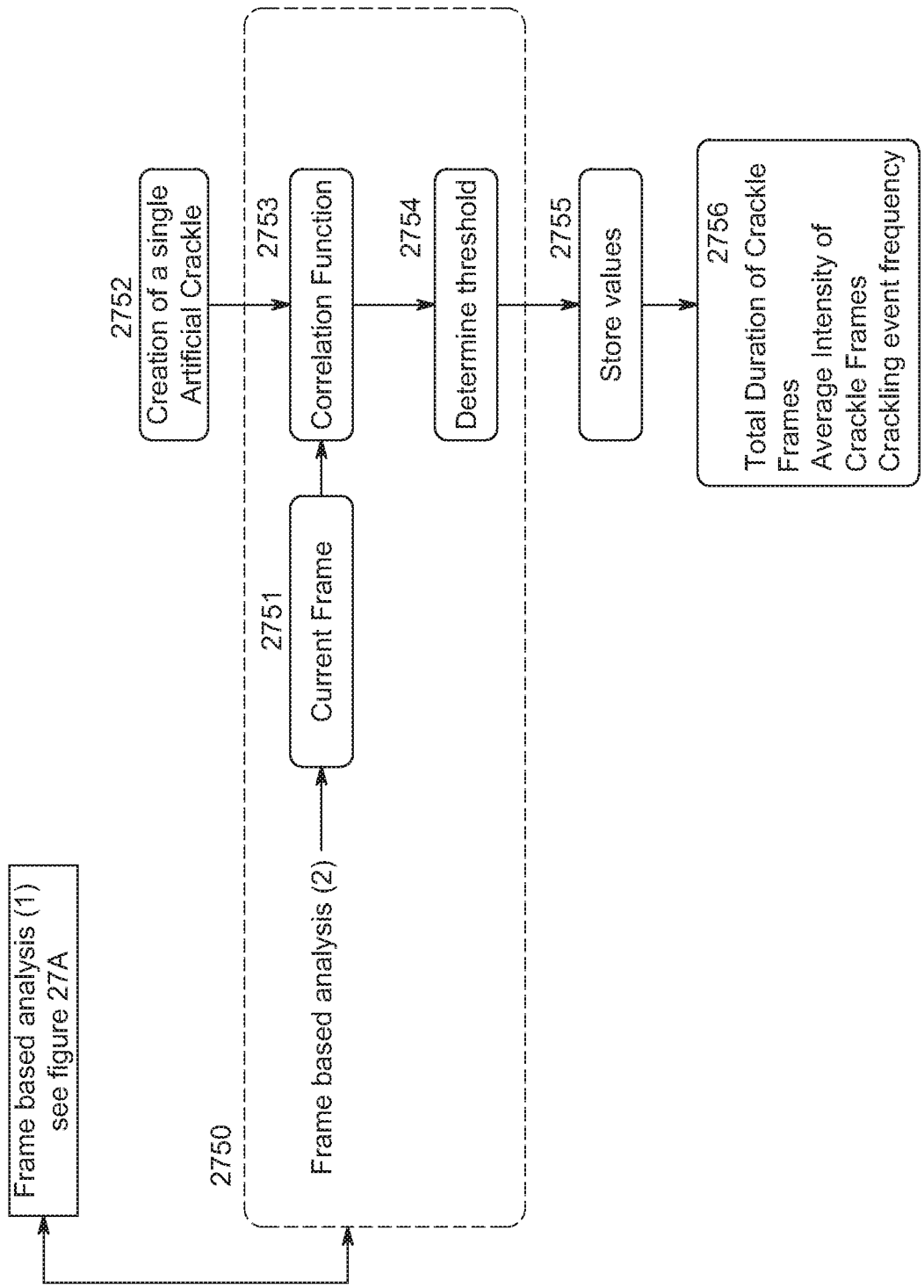
FIG. 27B illustrates a data flow diagram of a process that can be implemented to extract sound based descriptors pertaining to crackling in accordance with an embodiment of the present invention.

FIG. 27B illustrates a data flow diagram of a process that can be implemented to extract sound based descriptors pertaining to crackling in accordance with an embodiment of the present invention.

When a current frame 2751 is received into the crackle module 2750, at step 2752 a single artificial crackle is created—a filtered impulse response frame is created by filtering a delta function.

| | | |
|---|---|---|
| δ(n) = 1 | n = 0 | with a band pass filter with |
| δ(n) = 0 | n > 0 | range (100-300 Hz). |

Figure 32:
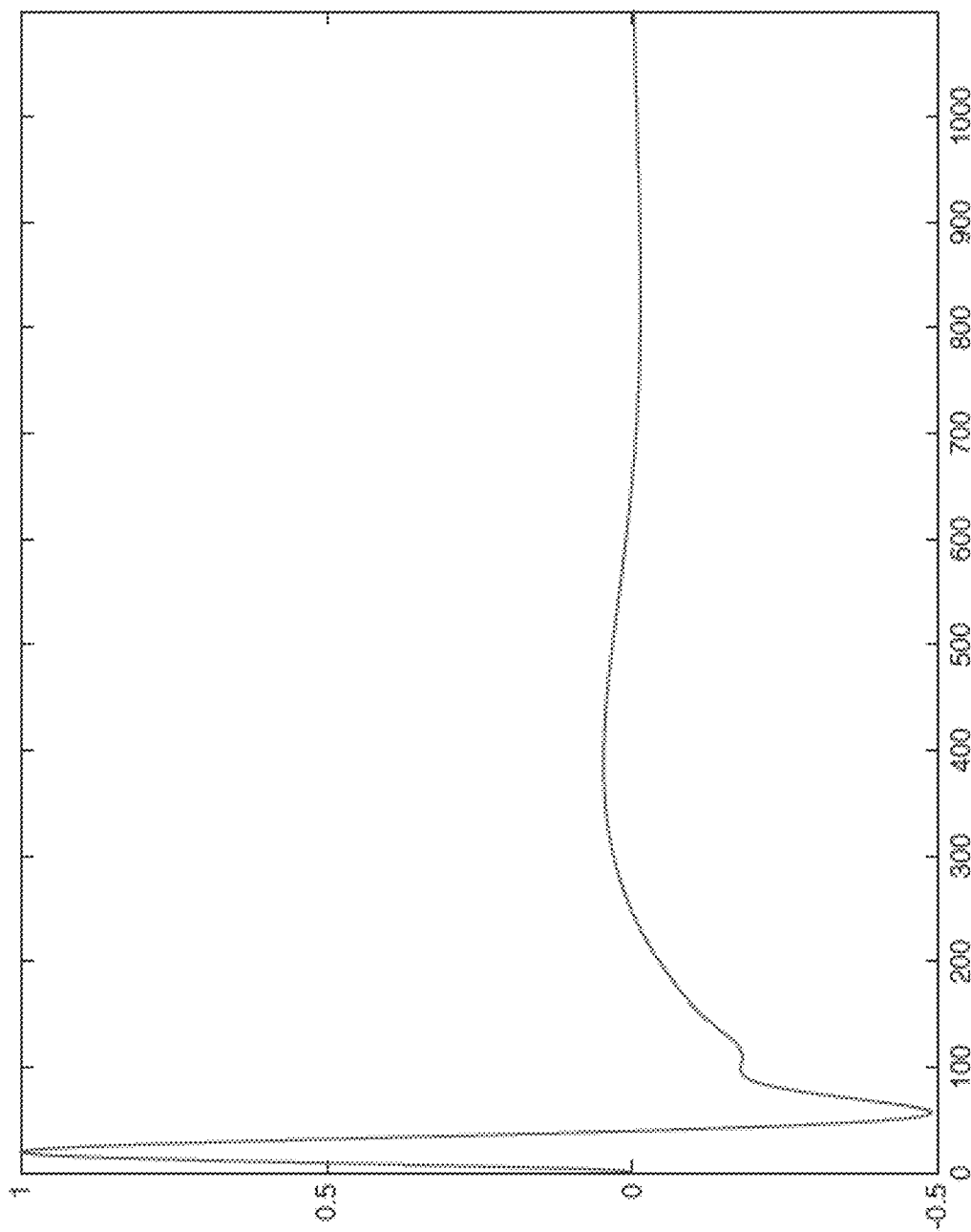
FIG. 32 illustrates the manner in which the filtered impulse response is created by filtering a delta function to create an artificial crackle in accordance with an embodiment of the present invention.

FIG. 32 illustrates the manner in which the filtered impulse response is created by filtering a delta function to create an artificial crackle in accordance with an embodiment of the present invention. The artificial crackle sound is formed by filtering a delta function with a narrow IIR band-pass filter. The filtered frame is the artificial crackle.

Figure 33:
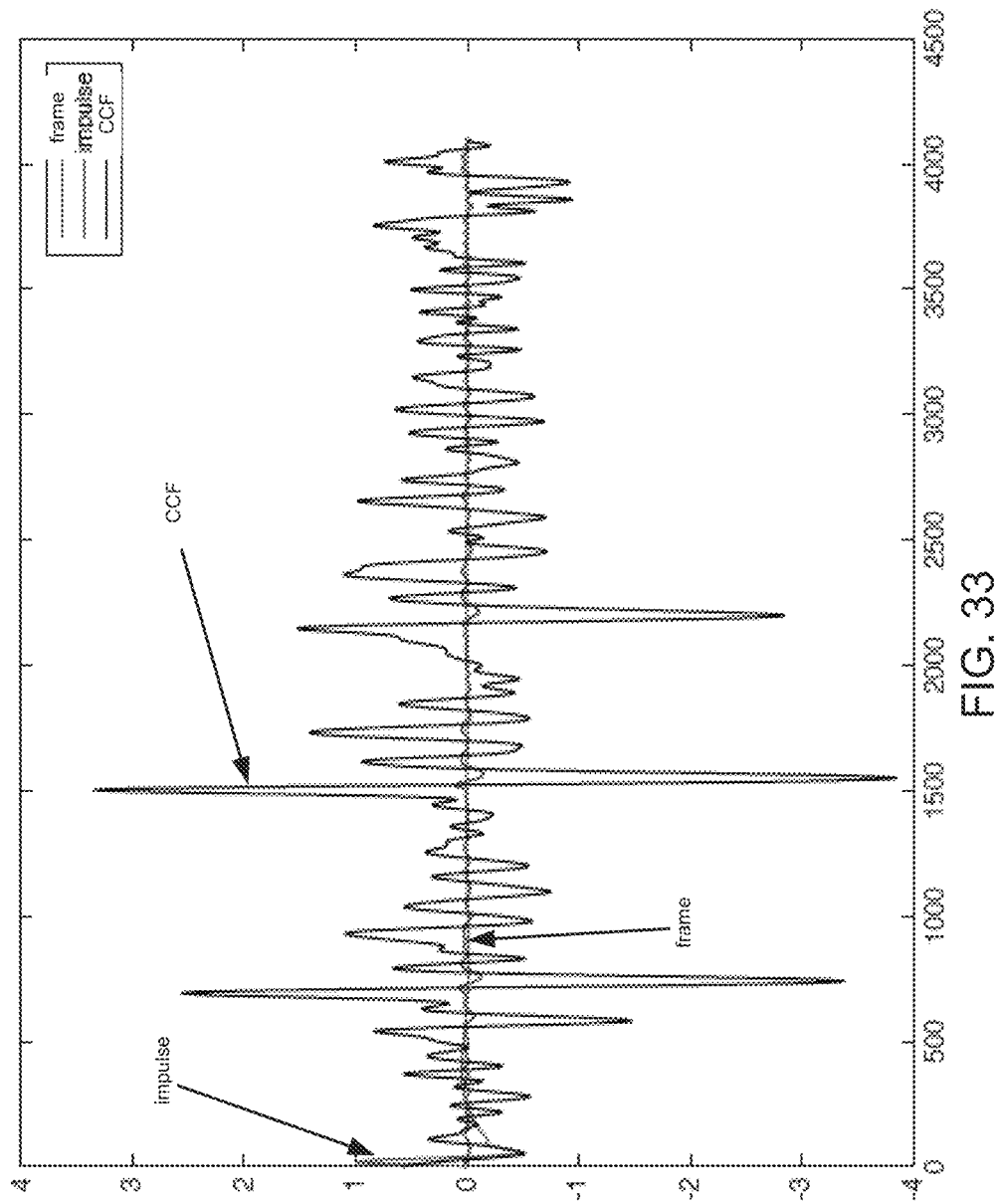
FIG. 33 illustrates the cross correlation function determined using the frame and the normalized filtered response in accordance with an embodiment of the present invention.

At step 2753, a cross correlation function is determined between every frame and the normalized filtered response. FIG. 33 illustrates the cross correlation function determined using the frame and the normalized filtered response in accordance with an embodiment of the present invention. At shown in FIG. 33, the cross correlation function exceed 1 at certain points—if the cross correlation function exceeds unity at least once, the frame is considered a crackling frame.

Accordingly, at step 2754, the thresholds for the cross correlation function (CCF) are determined and, subsequently, at step 2755, for every crackling frame, the software stores its time-stamp and its intensity for the feature and descriptor extraction.

At block 2756, at least three descriptors pertaining to crackling are determined:

Total duration of crackling frames—The total duration of crackling events.

Average Intensity of crackling frames—The intensity of the frames that feature crackling.

Crackling event frequency—How often crackles happen.

IV. Training and Evaluating an Artificial Neural Network (ANN) for Identifying Lung Pathology, Disease and Severity of Disease In one embodiment of the present invention, an artificial neural network (ANN) can be trained and evaluated to determine lung pathology, disease type and severity. The ANN system for determining lung pathology comprises a training module (shown in FIG. 34) and an evaluation module (shown in FIG. 35).

Figure 34:
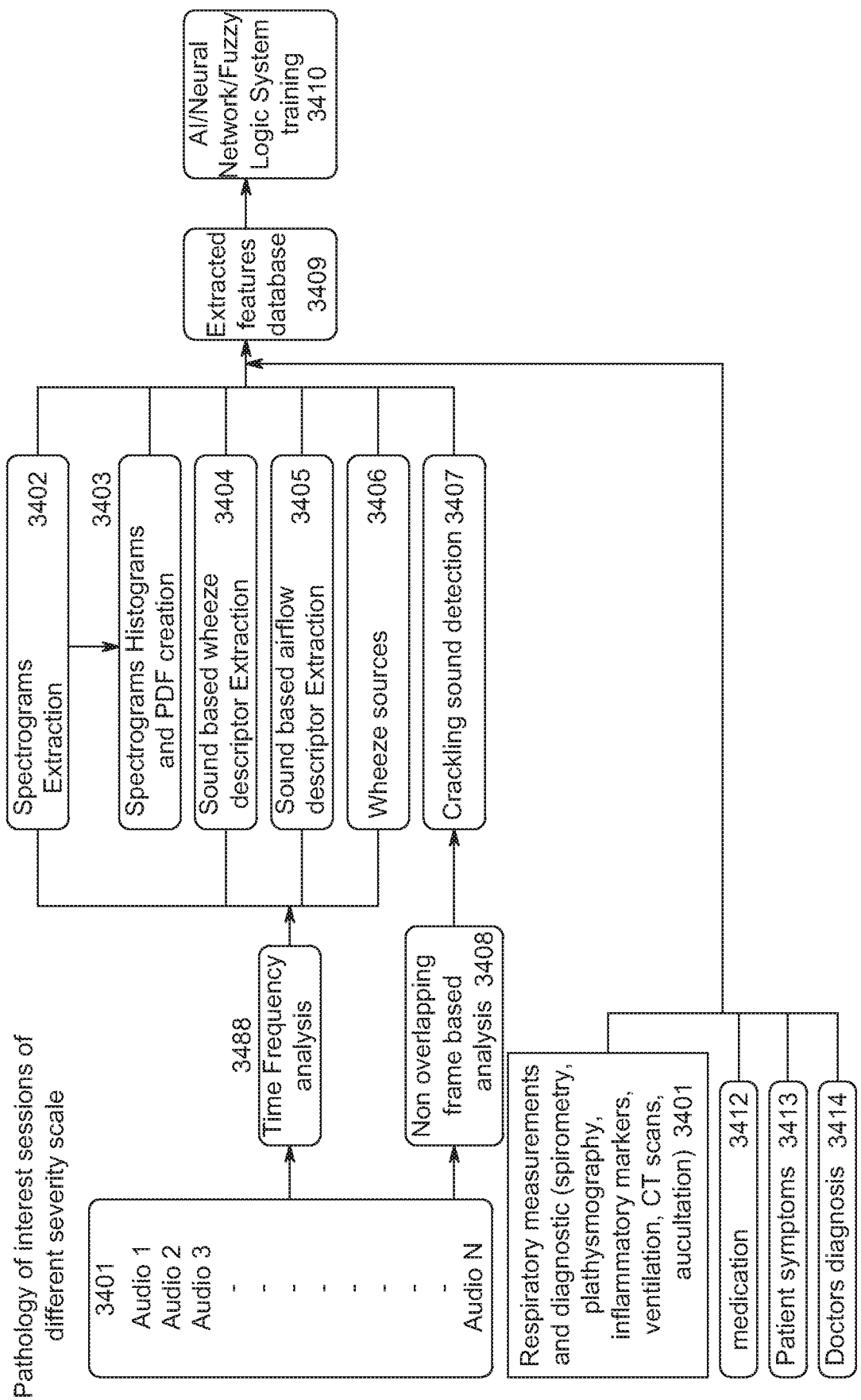
FIG. 34 illustrates a block diagram providing an overview of the manner in which an artificial neural network can be trained to ascertain lung pathologies in accordance with an embodiment of the present invention.

FIG. 34 illustrates a block diagram providing an overview of the manner in which an artificial neural network can be trained to ascertain lung pathologies in accordance with an embodiment of the present invention.

At block 3401 multiple audio files are inputted into the ANN training software—the audio files may comprise sessions with patients exhibiting symptoms of varying degrees of severity (mild, moderate, severe). Further, the symptoms may relate to a pathology of interest, e.g., asthma.

The audio frames are analyzed both using time frequency analysis (used for analyzing wheezes as discussed above) at block 3488 and using non-overlapping frame based analysis (used for analyzing crackles) at block 3408.

Additionally, the set of respiratory recordings at block 3401 that the training system uses may be annotated by specialists regarding health status, disease, pathology and severity and can include references from other diagnostic tests such auscultation, spirometry, CT scans, blood and sputum inflammatory and genetic markers, etc. The metadata used to annotate the respiratory recordings at block 3401 may comprise respiratory measurements and diagnostics 3411 (spirometry, plethysmography, inflammatory markers, ventilation, CT scans, auscultation, etc.), medication 3412, patient symptoms 3413, and doctor's diagnoses 3414.

Other physiological measurements and diagnostics, including pulmonary function testing (spirometry), blood oxygen levels (pulse oximetry), respiratory gas analysis ($O_2$, $CO_2$, VOCs, FeNO), body temperature, and blood and sputum inflammatory and genetic markers can be fed into the ANN algorithms. In addition, medication usage and tracking, users' symptoms, exercise and diet habits, and a doctor's diagnosis, can also be fed into the ANN algorithm.

These recordings together with the annotated metadata comprise the "training set." The ANN algorithms initially analyze the recordings contained in the training set by employing the frame-based analysis of wheeze module 2700 and crackle module 2750 in order to tune the ANN algorithms that will later evaluate new incoming recordings to determine whether they are associated with healthy lungs, and if not, then to determine lung pathology and disease type (e.g., asthma, COPD, etc.) and severity (mild, moderate, severe).

Each recording in the training set is analyzed using overlapping frames (as discussed in connection with wheeze module 2700 above) at block 3488. These frames are 4096 samples long and the overlap by 93% of their duration (every 256 samples). For example, if the used sample rate is 44.100 Hz, each frame lasts 92 msecs and the frames overlap every 5 msecs. The exemplary values were chosen to provide temporal and frequency accuracy. It should be noted that both the frame lengths and the overlap duration can vary.

Subsequently, the recordings are used to extract the various descriptors and images discussed above. For example, the spectrogram images are extracted at block 3402. Original spectrograms are created for each respiratory recording. These spectrograms are used to create probability density functions (PDFs) at block 3403. The PDFs that correspond to a specific health status (healthy lungs, mild asthma, moderate asthma, severe asthma, etc.) are averaged. FIG. 36 illustrates exemplary original spectrogram PDFs aggregated over pathology and severity in accordance with an embodiment of the present invention. As will be discussed further below, the PDFs are used in the evaluation module (discussed in connection with FIG. 35) to decide if a new respiratory recording inputted into the ANN belongs to a healthy category or to a category indicating disease by employing a Binary Hypothesis Likelihood Ratio Test.

At block 3404 sound based wheeze descriptors are extracted (e.g. the descriptors extracted at block 2710, 2733, 2734, 2708, and 2735). At block 3406, wheeze source and the associated descriptors are determined (e.g., descriptors determined at block 2711). Additionally, at block 3405, descriptors associated with sound based airflow are extracted (e.g. descriptors extracted at block 2736).

Using the non-overlapping frame based analysis at block 3408, the descriptors pertaining to crackle are also extracted at block 3407 (e.g., the descriptors from block 2756).

The next step is to store all the extracted spectrograms and descriptor, wherein the values for each of the respiratory recordings are stored separately in the extracted features database at block 3409. The descriptors are also aggregated over pathology and severity to tune the neural network layers and coefficients at block 3410.

Figure 35:
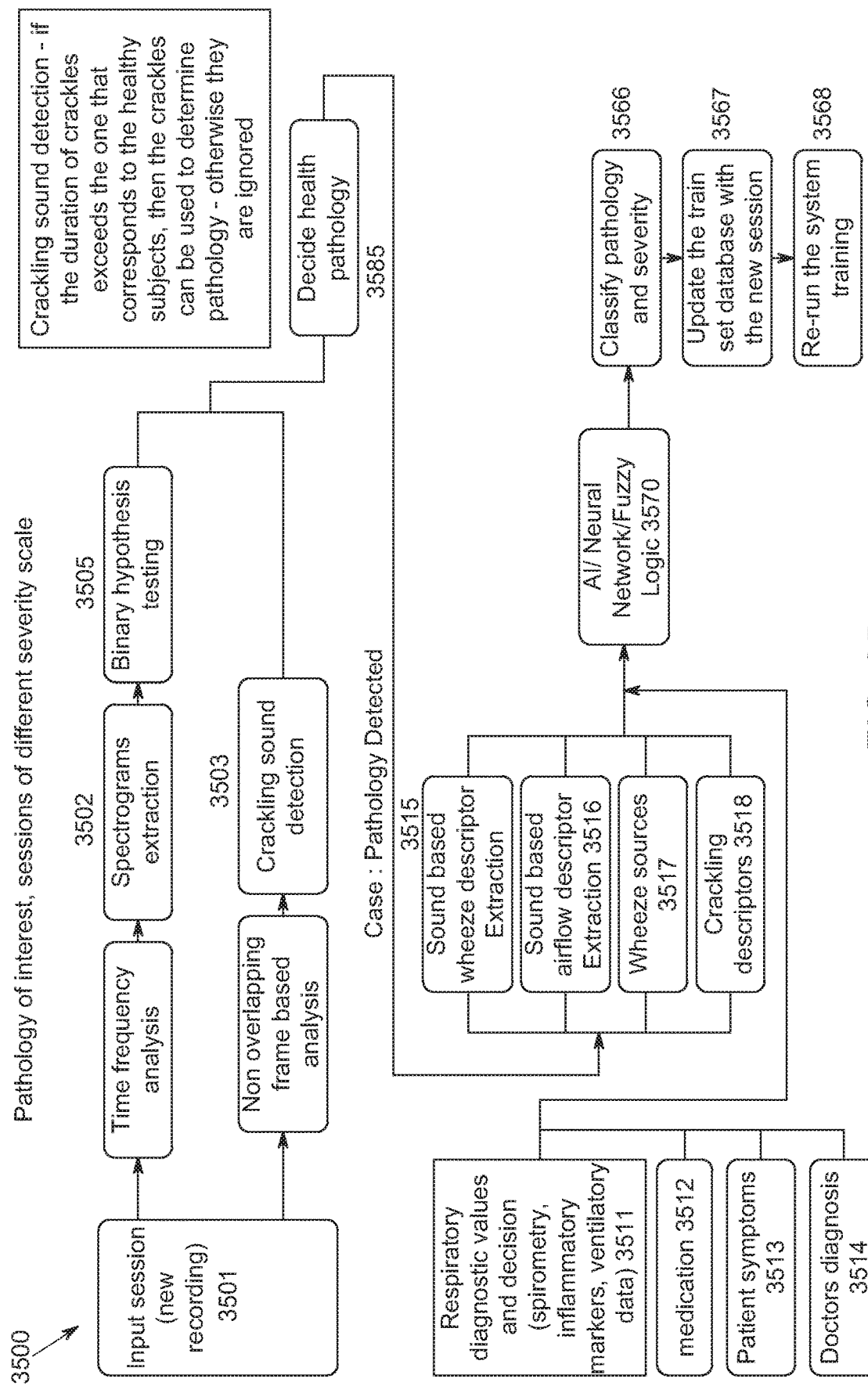
FIG. 35 illustrates a block diagram providing an overview of the manner in which an artificial neural network can be used to evaluate a respiratory recording associated with a patient to determine lung pathologies and severity in accordance with an embodiment of the present invention.
Figure 36:
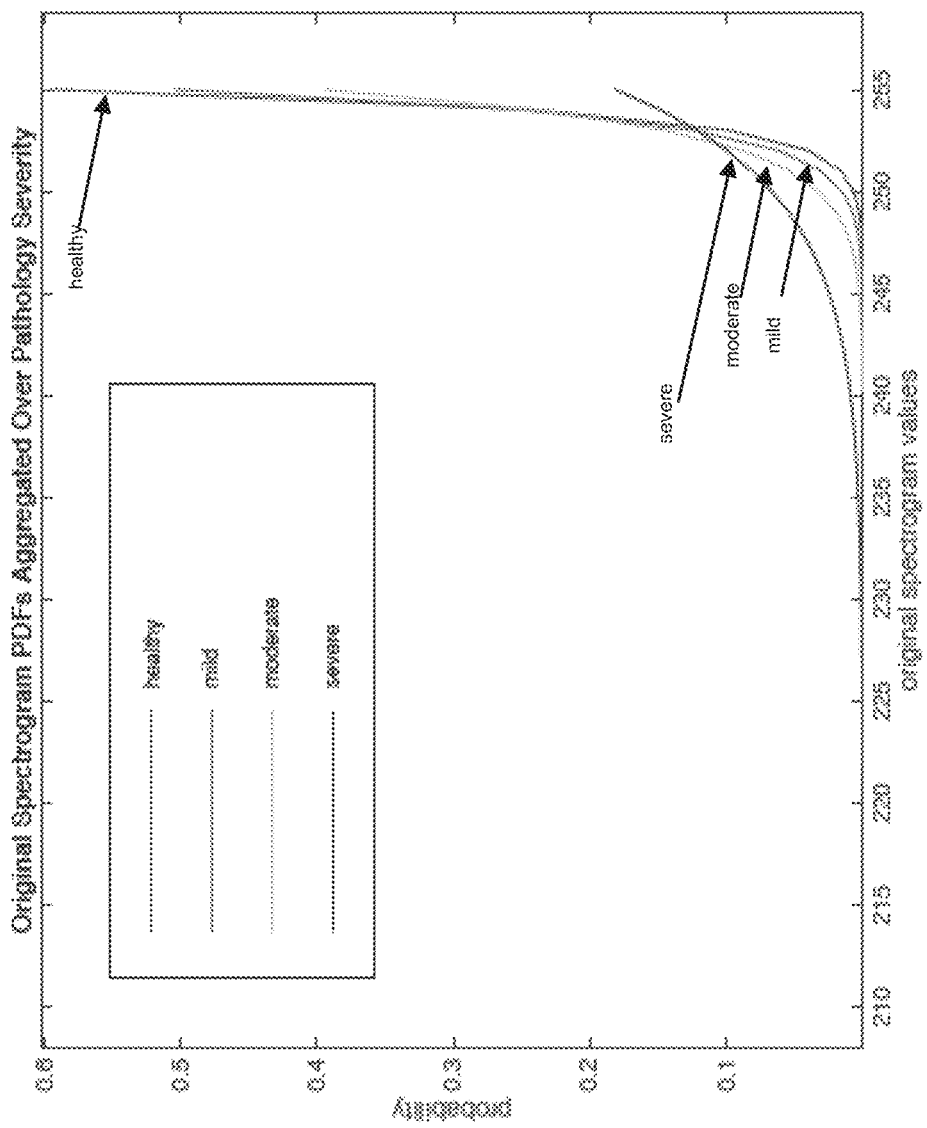
FIG. 36 illustrates exemplary original spectrogram PDFs aggregated over pathology and severity in accordance with an embodiment of the present invention.

FIG. 35 illustrates a block diagram providing an overview of the manner in which an artificial neural network can be used to evaluate a respiratory recording associated with a patient to determine lung pathologies and severity in accordance with an embodiment of the present invention.

The evaluation or decision-making module 3500 shown in FIG. 35 receives as an input a new recording at block 3501. The evaluation module then applies time frequency analysis and extracts a spectrogram (and associated PDF) at block 3502. This is similar to the way in which spectrograms and PDFs are extracted at blocks 3402 and 3403 in the training process shown in FIG. 34. Further, at block 3502, a histogram of the extracted spectrogram (either original spectrogram or a magnified spectrogram) is calculated. This histogram can be used to obtain the session's PDF.

The PDF can be obtained as follows:

$$P_i = \frac{H_i}{\sum_i H_i}$$

where: $H_i$ the histogram elements.

The decision-making module also applies non-overlapping frame based analysis and extracts sound descriptors pertaining to crackling at block 3503. Accordingly, the evaluation module analyzed both the wheeze-based spectrograms and descriptors to determine pathology as well as the crackle-based descriptors.

At block 3505, for the wheeze-based analysis, a binary hypothesis test is performed at block 3505 to determine if the recording is associated with a healthy patient or if the patient is showing characteristics of disease or pathology, which may need further investigation. The binary hypothesis test may provide a binary (true/false) response when evaluating a patient's condition. This binary decision can be carried out after the PDFs in the training set are averaged and the resulting PDFs are correlated with a pathology pattern (mild to severe as shown in FIG. 36). The PDF of the session with the new patient during evaluation can then be compared to the averaged PDFs developed during the training session. In other words, the PDF of the new recording from the patient at block 3501 can be mapped onto the averaged PDFs determined during the training session to determine if there is a match between the PDF from the new session and any of the pathology patterns as determined during the training session.

The Binary Hypothesis Test performed at block 3505 has the following form:

$$\Lambda = \sum_{n=1}^{N} \phi(x_n) \begin{matrix} H_0 \\ \geq \\ < \\ H_1 \end{matrix} 0$$

where:

$$\phi(x) = \log\left(\frac{f_H(x)}{f_A(x)}\right) \quad f_H(x): \text{healthy}, f_P(x): \text{pathology } PDF\text{'s}$$

Figure 37:
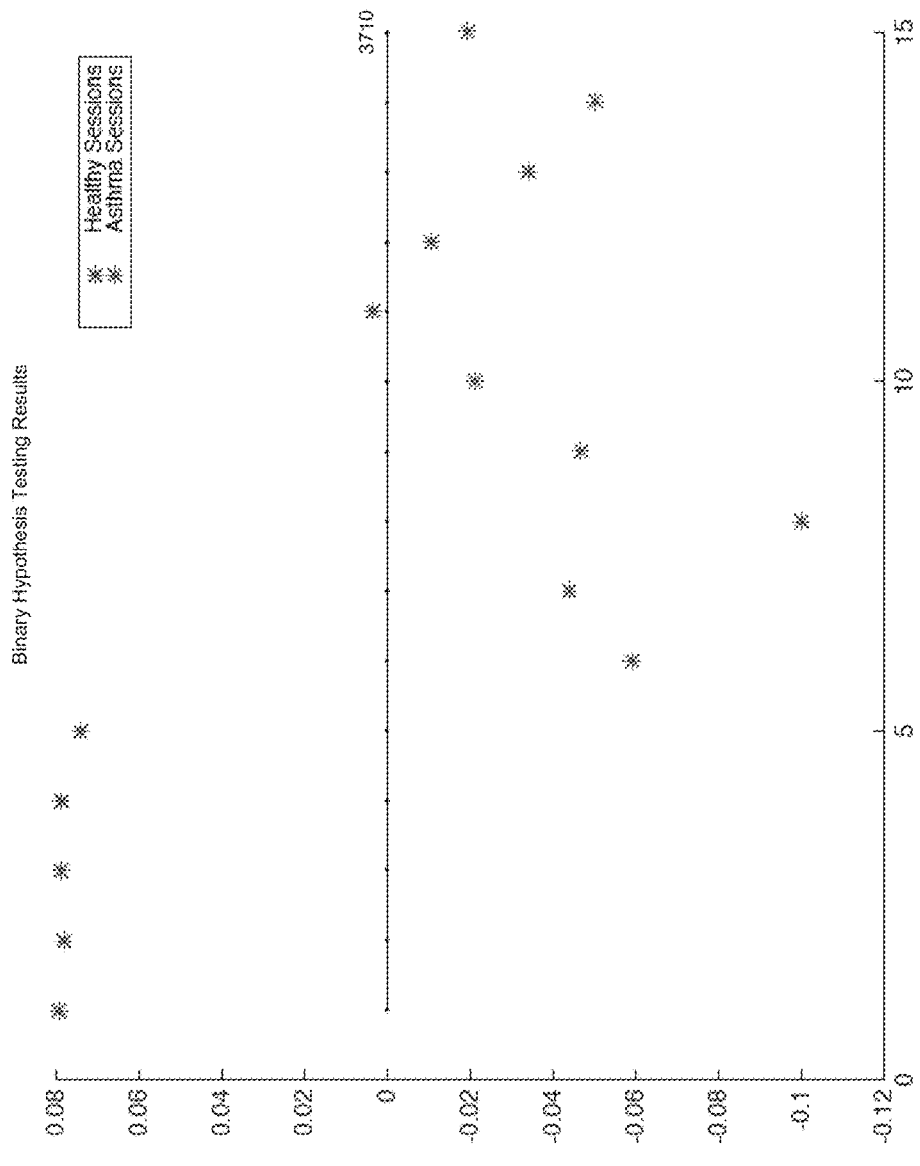
FIG. 37 illustrates exemplary results from the binary hypothesis testing conducted at block 3505 in accordance with an embodiment of the present invention.

$\Lambda > 0$ decide healthy $\Lambda < 0$ decide pathology $\Lambda = 0$ decide randomly FIG. 37 illustrates exemplary results from the binary hypothesis testing conducted at block 3505 in accordance with an embodiment of the present invention. The binary hypothesis testing on incoming new sessions is conducted after the ANN has been trained with a prior data set. As seen in FIG. 37, the sessions associated with points above line 3710 are estimated as healthy, whereas the sessions associated with points below the line 3710 are estimated as related to lung pathology.

Subsequent to the binary hypothesis testing, a recording that has been identified as healthy (or containing no indicia of pathology) may not need to be analyzed further—it is stored as part of the user or patient profile in an associated database for future reference. Each subject's complete data is stored in the database. Each time a new respiratory recording related to the patient is fed into the system, the test is repeated taking into account the stored data in order to detect a possible statistical change that could mean that early stages of pathology or lung disease are present.

In one embodiment, if neither the binary hypothesis testing performed at block 3505 and the crackling sound detection at block 3503 show any indications of a pathology (in other words, if both methods of analyzing the new input session or recording from the patient indicate that the patient's lungs are healthy), then the analysis can optionally be stopped at block 3585. In other words, only if a pathology is detected does the analysis progress further. Alternatively, in a different embodiment, the analysis can continue by extracting descriptors at blocks 3515-3518 even if the patient has healthy lungs.

When the respiratory recording is characterized as a pathology at block 3585, the descriptor extraction modules (sound based wheeze descriptors at block 3515, sound based airflow descriptors at block 3516, wheeze source descriptors at block 3517, crackling descriptors at 3503) are employed to extract the pathology and disease related features. The descriptor extraction modules are similar to the blocks 3402, 3403, 3404, 3405, 3406 and 3407 discussed in connection with FIG. 34. The descriptors and all the metadata information from blocks 3511, 3512, 3513 and 3514 are fed into the ANN module 3570. The ANN module 3570 then determines the pathology, disease and severity at block 3566 using the information learned from the processing of the training sets.

As mentioned above, the metadata may include other physiological measurements and diagnostics, including pulmonary function testing (spirometry), blood oxygen levels (pulse oximetry), respiratory gas analysis (O2, CO2, VOCs, FeNO), body temperature, plethsmography, CT scans, and blood and sputum inflammatory and genetic markers can be fed into the ANN algorithms. Medication usage and tracking, a users' symptoms, exercise and diet, and a doctor's diagnosis, can also be fed into the ANN algorithm.

The classified session 3501 is stored to the training database at block 3567 in order to augment the training set. Subsequently, the algorithm re-runs the training to update its state at block 3568. The extracted features may also be stored to the user profile database in order to compare the new user data to the previous user data for tracking purposes. If a new recording shows characteristics of pathology or disease progression, its characteristics can be compared to the data that has been extracted from older recordings in order to estimate the rate of pathology or disease progression.

Figure 38:
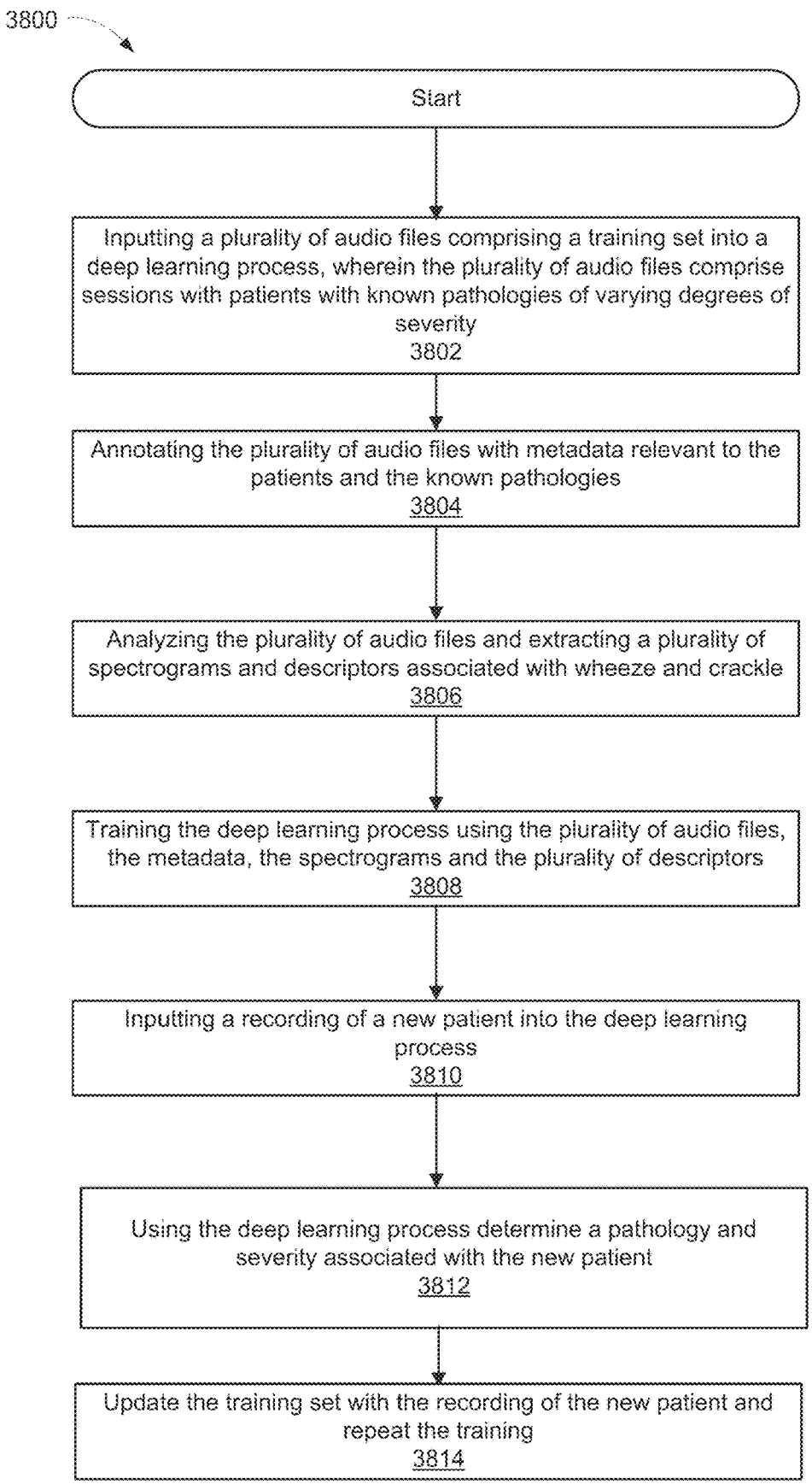
FIG. 38 depicts a flowchart illustrating an exemplary computer-implemented process for determining lung pathologies and severity from a respiratory recording using an artificial neural network in accordance with one embodiment of the present invention.

FIG. 38 depicts a flowchart 3800 illustrating an exemplary computer-implemented process for determining lung pathologies and severity from a respiratory recording using an artificial neural network in accordance with one embodiment of the present invention. While the various steps in this flowchart are presented and described sequentially, one of ordinary skill will appreciate that some or all of the steps can be executed in different orders and some or all of the steps can be executed in parallel. Further, in one or more embodiments of the invention, one or more of the steps described below can be omitted, repeated, and/or performed in a different order. Accordingly, the specific arrangement of steps shown in FIG. 38 should not be construed as limiting the scope of the invention. Rather, it will be apparent to persons skilled in the relevant art(s) from the teachings provided herein that other functional flows are within the scope and spirit of the present invention. Flowchart 3800 may be described with continued reference to exemplary embodiments described above, though the method is not limited to those embodiments.

At step 3802, a plurality of audio files comprising a training set are inputted into a artificial neural network (ANN) or deep learning process. The plurality of audio files comprise sessions with patients with known pathologies of varying degrees of severity.

At step 3804, the plurality of audio files are annotated with metadata relevant to the patients and the known pathologies. For example, the metadata used to annotate the respiratory recordings at block 3401 may comprise respiratory measurements and diagnostics 3411 (spirometry, plethysmography, inflammatory markers, ventilation, CT scans, auscultation, etc.), medication 3412, patient symptoms 3413, and doctor's diagnoses 3414. Other physiological measurements and diagnostics, including pulmonary function testing (spirometry), blood oxygen levels (pulse oximetry), respiratory gas analysis (O2, CO2, VOCs, FeNO), body temperature, and blood and sputum inflammatory and genetic markers can be fed into the ANN algorithms. In addition, medication usage and tracking, users' symptoms, exercise and diet habits, and a doctor's diagnosis, can also be fed into the ANN algorithm.

At step 3806, the plurality of audio files are analyzed and a respective spectrogram is extracted for each of the audio files. Further, a plurality of descriptors associated with wheeze and crackle are determined from the plurality of audio files.

At step 3808, the deep learning process is trained using the plurality of audio files, the spectrograms, the descriptors, and the metadata (e.g. as shown at block 3410).

At step 3810, a new recording from a new patient is inputted into the deep learning process. At step 3812, using the deep learning process a pathology is determined with an associated severity for the new patient. As mentioned above, the pathology determination is made using a binary hypothesis testing process. Further, the pathology determination is made using both crackle sound descriptors and analyzing spectrograms for wheeze-related symptoms.

At step 3814, the training set of audio files is updated with the recording of the new patient and the training process is repeated with the additional new recording. Subsequent new recordings are analyzed with the updated deep learning process.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered as examples because many other architectures can be implemented to achieve the same functionality.

The process parameters and sequence of steps described and/or illustrated herein are given by way of example only. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. These software modules may configure a computing system to perform one or more of the example embodiments disclosed herein. One or more of the software modules disclosed herein may be implemented in a cloud computing environment. Cloud computing environments may provide various services and applications via the Internet. These cloud-based services (e.g., software as a service, platform as a service, infrastructure as a service, etc.) may be accessible through a Web browser or other remote interface. Various functions described herein may be provided through a remote desktop environment or any other cloud-based computing environment.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as may be suited to the particular use contemplated.

Embodiments according to the invention are thus described. While the present disclosure has been described in particular embodiments, it should be appreciated that the invention should not be construed as limited by such embodiments, but rather construed according to the below claims.

What is claimed is:

1. A method for analyzing an audio respiratory signal, the method comprising:
    capturing the audio respiratory signal from a subject using a microphone;
    partitioning the audio respiratory signal into a plurality of overlapping frames and a plurality of non-overlapping frames;
    calculating a fourier transform for each frame;
    determining a magnitude spectrum using the fourier transform of the plurality of overlapping frames;
    extracting a spectrogram using the magnitude spectrum;
    analyzing the spectrogram to determine characteristics pertaining to wheeze sounds in the audio respiratory signal;
    creating an artificial crackle comprising a filtered impulse response frame created by filtering a delta function;
    calculating a cross correlation function between each of the non-overlapping frames and the artificial crackle;
    determining if the cross correlation function exceeds a predetermined threshold; and
    responsive to a determination that the cross correlation function exceeds the predetermined threshold, identifying a respective frame for which the cross correlation function exceeds the predetermined threshold as associated with crackling.

2. The method of claim 1, wherein the artificial crackle is created by filtering the delta function in the filtered impulse response frame with a narrow IIR bandpass filter.

3. The method of claim 1, further comprising:
    storing a timestamp and intensity corresponding to each frame identified as associated with crackling; and
    extracting a plurality of characteristics pertaining to crackling using frames identified as associated with crackling.

4. The method of claim 1, further comprising:
    extracting a magnified spectrogram using the spectrogram, wherein the magnified spectrogram is operable to determine a number of wheeze particles.

5. The method of claim 1, further comprising:
    extracting an interpolated spectrogram using the spectrogram, wherein the interpolated spectrogram is operable to provide a clearer view of wheeze particles by subtracting out residual airflow energies from the spectrogram.

6. The method of claim 1, wherein the analyzing further comprises:
    executing an edge-detection procedure on the spectrogram to highlight wheeze particles in the spectrogram.

7. The method of claim 6, wherein the analyzing further comprises:
    for each column in the spectrogram, performing the following:
        (a) store locations of elements with high values resulting from the edge-detection procedure into a vector;
        (b) compare a location of the first element in the vector with locations of remaining elements in the vector;
        (c) designate any of the remaining elements where a respective location is a multiple of the location of the first element as a harmonic of the first element; and
        (d) repeat steps a), b) and c) for each element in the vector.

8. A non-transitory computer-readable storage medium having stored thereon, computer executable instructions that, if executed by a computer system cause the computer system to perform a method for analyzing an audio respiratory signal, the method comprising:
    capturing the audio respiratory signal from a subject using a microphone;
    partitioning the audio respiratory signal into a plurality of overlapping frames and a plurality of non-overlapping frames;
    calculating a fourier transform for each frame;
    extracting a spectrogram using the fourier transform of the plurality of overlapping frames;
    analyzing the spectrogram to determine characteristics pertaining to wheeze sounds in the audio respiratory signal;
    creating an artificial crackle comprising a filtered impulse response frame created by filtering a delta function;
    calculating a cross correlation function between each of the non-overlapping frames and the artificial crackle;
    determining if the cross correlation function exceeds a predetermined threshold; and
    responsive to a determination that the cross correlation function exceeds the predetermined threshold, identifying a respective frame for which the cross correlation function exceeds the predetermined threshold as associated with crackling.

9. The non-transitory computer-readable storage medium of claim 8, wherein the artificial crackle is created by filtering the delta function in the filtered impulse response frame with a narrow IIR bandpass filter.

10. The non-transitory computer-readable storage medium of claim 8, wherein the method further comprises:
    storing a timestamp and intensity corresponding to each frame identified as associated with crackling; and
    extracting a plurality of characteristics pertaining to crackling using frames identified as associated with crackling.

11. The non-transitory computer-readable storage medium of claim 8, wherein the method further comprises:
    extracting a magnified spectrogram using the spectrogram, wherein the magnified spectrogram is operable to determine a number of wheeze particles.

12. The non-transitory computer-readable storage medium of claim 8, wherein the method further comprises:
    extracting an interpolated spectrogram using the spectrogram, wherein the interpolated spectrogram is operable to provide a clearer view of wheeze particles by subtracting out residual airflow energies from the spectrogram.

13. A system for detecting wheeze and crackle from an audio respiratory signal, the system comprising:
    a spirometer comprising a first microphone, wherein the first microphone is operable to capture the audio respiratory signal from a subject;
    a memory coupled to the spirometer and operable to store the audio respiratory signal, wherein the memory further comprises an application for detecting wheeze and crackle from a breathing session stored therein; and
    a processor coupled to said memory and said spirometer, the processor being configured to operate in accordance with said application to:
        capture the audio respiratory signal from a subject using a microphone;

partition the audio respiratory signal into a plurality of overlapping frames and a plurality of non-overlapping frames;

calculate a fourier transform for each frame;

determine a magnitude spectrum using the fourier transform of the plurality of overlapping frames;

extract a spectrogram using the magnitude spectrum;

analyze the spectrogram to determine characteristics pertaining to wheeze sounds in the audio respiratory signal;

create an artificial crackle comprising a filtered impulse response frame created by filtering a delta function;

calculate a cross correlation function between each of the non-overlapping frames and the artificial crackle;

determine if the cross correlation function exceeds a predetermined threshold; and responsive to a determination that the cross correlation function exceeds the predetermined threshold, identify a respective frame for which the cross correlation function exceeds the predetermined threshold as associated with crackling.

14. The system of claim 13, wherein the artificial crackle is created by filtering the delta function in the filtered impulse response frame with a narrow IIR bandpass filter.

15. The system of claim 13, wherein the processor is further configured to:

store a timestamp and intensity corresponding to each frame identified as associated with crackling; and extract a plurality of characteristics pertaining to crackling using frames identified as associated with crackling.

16. The system of claim 13, wherein the processor is further configured to:

extract a magnified spectrogram using the spectrogram, wherein the magnified spectrogram is operable to determine a number of wheeze particles.

17. The system of claim 13, wherein the processor is further configured to:

extract an interpolated spectrogram using the spectrogram, wherein the interpolated spectrogram is operable to provide a clearer view of wheeze particles by subtracting out residual airflow energies from the spectrogram.

* * * * *